(12) United States Patent
Bae et al.

(10) Patent No.: US 11,180,538 B2
(45) Date of Patent: Nov. 23, 2021

(54) COMBINATORIAL GENE CONSTRUCT AND NON-VIRAL DELIVERY FOR ANTI-OBESITY

(71) Applicant: UNIVERSITY OF UTAH RESEARCH FOUNDATION, Salt Lake City, UT (US)

(72) Inventors: You Han Bae, Salt Lake City, UT (US); Hongsuk Park, Salt Lake City, UT (US); Sungpil Cho, Salt Lake City, UT (US)

(73) Assignee: UNIVERSITY OF UTAH RESEARCH FOUNDATION, Salt Lake City, UT (US)

( * ) Notice: Subject to any disclaimer, the term of this patent is extended or adjusted under 35 U.S.C. 154(b) by 732 days.

(21) Appl. No.: 15/776,067

(22) PCT Filed: Mar. 25, 2016

(86) PCT No.: PCT/US2016/024185
§ 371 (c)(1),
(2) Date: May 14, 2018

(87) PCT Pub. No.: WO2017/082946
PCT Pub. Date: May 18, 2017

(65) Prior Publication Data
US 2020/0247864 A1 Aug. 6, 2020

Related U.S. Application Data

(60) Provisional application No. 62/254,745, filed on Nov. 13, 2015.

(51) Int. Cl.
*C07K 14/575* (2006.01)
*C07K 14/78* (2006.01)
(Continued)

(52) U.S. Cl.
CPC .......... *C07K 14/5759* (2013.01); *A61K 48/00* (2013.01); *C07K 14/575* (2013.01);
(Continued)

(58) Field of Classification Search
CPC .. C07K 14/5759; C07K 14/575; C07K 14/78; A61K 48/00; A61K 38/00;
(Continued)

(56) References Cited

U.S. PATENT DOCUMENTS 4,863,457 A 9/1989 Lee
5,378,475 A 1/1995 Smith et al.
(Continued)

FOREIGN PATENT DOCUMENTS

| WO | WO 94/16737 A1 | 8/1994 | |
| WO | WO-2007055728 A1 * | 5/2007 | ......... A61K 38/2278 |
| WO | WO-2009064298 A1 * | 5/2009 | ......... A61K 38/2264 |

OTHER PUBLICATIONS

Underhill, M. F., Smales, C. M., Naylor, L. H., Birch, J. R., & James, D. C. (2007). Transient gene expression levels from multigene expression vectors. Biotechnology progress, 23(2), 435-443. (Year: 2007).*

(Continued)

*Primary Examiner* — Kevin K Hill
*Assistant Examiner* — Anjeanette Roberts
(74) *Attorney, Agent, or Firm* — Michael Best & Friedrich LLP

(57) ABSTRACT

The invention provides a plasmid comprising two or more anti-obesity genes. Also provided by the invention are compositions and host cells comprising the plasmid and methods of increasing the metabolic activity in a mammal. The invention provides a plasmid comprising two or more of (a) a nucleic acid sequence encoding islet amyloid polypeptide (IAPP), (b) a nucleic acid sequence encoding leptin (Continued)

(LEP), and (c) a nucleic acid sequence encoding fibronectin type III domain containing 5 (FNDC5).

16 Claims, 35 Drawing Sheets

Specification includes a Sequence Listing.

(51) Int. Cl.
| | |
|---|---|
| *C12N 5/071* | (2010.01) |
| *C12N 9/64* | (2006.01) |
| *A61K 48/00* | (2006.01) |
| *A61K 38/00* | (2006.01) |

(52) U.S. Cl.
CPC ............ *C07K 14/78* (2013.01); *C12N 5/0602* (2013.01); *C12N 9/6454* (2013.01); *C12Y 304/21075* (2013.01); *A61K 38/00* (2013.01); *A61K 48/0041* (2013.01); *A61K 48/0075* (2013.01)

(58) Field of Classification Search
CPC ............ A61K 48/0041; A61K 48/0075; C12N 5/0602; C12N 9/6454; C12Y 304/21075
See application file for complete search history.

(56) References Cited

U.S. PATENT DOCUMENTS

| | | | |
|---|---|---|---|
| 5,443,505 A | 8/1995 | Wong et al. | |
| 5,593,972 A | 1/1997 | Weiner et al. | |
| 5,962,428 A | 10/1999 | Carrano et al. | |
| 2011/0171276 A1* | 7/2011 | Cheung | A61P 3/00 424/400 |
| 2013/0074199 A1* | 3/2013 | Spiegelman | C07K 19/00 800/9 |

OTHER PUBLICATIONS

Chng, J., Wang, T., Nian, R., Lau, A., Hoi, K. M., Ho, S. C., et al. (2015, March). Cleavage efficient 2A peptides for high level monoclonal antibody expression in CHO cells. MAbs (vol. 7, No. 2, pp. 403-412). (Year: 2015).*
Altschul et al., "Basic local alignment search tool.," J. Molecular Biol., 215(3): 403-410 (1990).
Altschul et al., "Gapped BLAST and PSI-BLAST: a new generation of protein database search programs," Nucleic Acids Res., 25(17): 3389-3402 (1997).
Beigert et al., "Sequence context-specific profiles for homology searching," Proc. Natl. Acad. Sci. USA, 106(10): 3770-3775 (2009).
Bonnet et al., "Systemic delivery of DNA or siRNA mediated by linear polyethylenimine (L-PEI) does not induce an inflammatory response," Pharm. Res. 25, 2972-2982 (2008).
Boström et al., "A PGC1-α-dependent myokine that drives brown-fat-like development of white fat and thermogenesis," Nature 481, 463-468 (2012).
Carey et al., "Reprogramming of murine and human somatic cells using a single polycistronic vector," Proc. Natl. Acad. Sci. U.S.A. 106, 157-162 (2009).
Chiu et al., "Tumor-targeted gene delivery via anti-HER2 antibody (trastuzumab, Herceptin) conjugated polyethylenimine," J. Control Release 97, 357-369 (2004).
Contreras et al., "The brain and brown fat,". Ann. Med. 47, 150-168 (2015).
Cooke et al., "The obesity pipeline: current strategies in the development of anti-obesity drugs," Nat. Rev. Drug Discovery 5, 919-931 (2006).
Daskalopoulou et al., "Plasma irisin levels progressively increase in response to increasing exercise workloads in young, healthy, active subjects," Eur. J. Endocrinol. 171(3): 343-52 (2014).
Deng et al., "Use of the 2A peptide for generation of multi-transgenic pigs through a single round of nuclear transfer," PLoS One 6, e19986 (2011).
Depaoli, "20 Years of Leptin: Leptin in common obesity and associated disorders of metabolism," J. Endocrinol. 223, T71-T81 (2014).
Dube et al., "Central Leptin Gene Therapy Blocks High-Fat Diet-Induced Weight Gain, Hyperleptinemia, and Hyperinsulinemia," Diabetes, Jun. 1, 2002, vol. 51, No. 6, pp. 1729-1736.
Fang et al., "Stable antibody expression at therapeutic levels using the 2A peptide," Nature Biotechnol. 23, 584-590 (2005).
Ferrari et al., "ExGen 500 is an efficient vector for gene delivery to lung epithelial cells in vitro and in vivo," Gene Ther. 4, 1100-1106 (1997).
Ferrari et al., "Polyethylenimine shows properties of interest for cystic fibrosis gene therapy," Biochim. Biophys. Acta 1447, 219-225 (1999).
Gao et al. "Gene Therapy for Obesity: Progress and Prospects," Discovery Medicine, Jun. 1, 2014, vol. 17, No. 96, pp. 319-328.
Geisbert et al., "Postexposure protection of guinea pigs against a lethal ebola virus challenge is conferred by RNA interference," J. Infect. Dis. 193, 1650-1657 (2006).
Harms et al., "Brown and beige fat: development, function and therapeutic potential," Nat. Med. 19, 1252-1263 (2013).
Haslam et al., "Obesity," Lancet 366, 1197-1209 (2005).
Huh et al., "Optimization of 25 kDa linear polyethylenimine for efficient gene delivery," Biologicals 35, 165-171 (2007).
International Search Report and Written Opinion for Application No. PCT/US2016/024185 dated Jul. 1, 2016 (11 pages).
Intra et al., "Characterization of the transgene expression generated by branched and linear polyethylenimine-plasmid DNA nanoparticles in vitro and after intraperitoneal injection in vivo," J. Control. Release 130, 129-138 (2008).
Itaka et al., "In situ single cell observation by fluorescence resonance energy transfer reveals fast intra-cytoplasmic delivery and easy release of plasmid DNA complexed with linear polyethylenimine," J. Gene Med. 6, 76-84 (2004).
Kanasaki et al., "Biology of Obesity: Lessons from Animal Models of Obesity," Journal of Biomedicine and Biotechnology, 2011: 197636 (2011).
Kasturi et al., "Covalent conjugation of polyethyleneimine on biodegradable microparticles for delivery of plasmid DNA vaccines," Biomaterials, 26(32): 6375-6385 (2005).
Kawakami et al., "Evaluation of proinflammatory cytokine production induced by linear and branched polyethylenimine/plasmid DNA complexes in mice," J. Pharmacol. Exp. Ther. 317, 1382-1390 (2006).
Kawakami et al., "Nonviral approaches for targeted delivery of plasmid DNA and oligonucleotide," J. Pharm. Sci., 97(2): 726-745 (2008).
Kim et al., "High cleavage efficiency of a 2A peptide derived from porcine teschovirus-1 in human cell lines, zebrafish and mice," PLoS One 6, e18556 (2011).
Kim et al., "In vivo evaluation of doxorubicin-loaded polymeric micelles targeting folate receptors and early endosomal pH in drug-resistant ovarian cancer," Mol. Pharmaceutics 6, 1353-1362 (2009).
Kuninger et al., "Pro-protein convertases control the maturation and processing of the iron-regulatory protein, RGMc/hemojuvelin," BMC Biochemistry, 9: 9 (2008).
Kuo et al., "BMP-9 as a potent brown adipogenic inducer with anti-obesity capacity," Biomaterials 35, 3172-3179 (2014).
Kwoh et al., "Stabilization of poly-L-lysine/DNA polyplexes for in vivo gene delivery to the liver," Biochim. Biophys. Acta 1444, 171-190 (1999).
Levine et al., "Role of nonexercise activity thermogenesis in resistance to fat gain in humans," Science 283, 212-214 (1999).
Lin et al., "Soluble hemojuvelin is released by proprotein convertase-mediated cleavage at a conserved polybasic RNRR site," Blood Cells, 40(1):122-31 (2008).
Louis et al., "Intraperitoneal linear polyethylenimine (L-PEI)-mediated gene delivery to ovarian carcinoma nodes in mice," Cancer Gene Ther. 13, 367-374 (2006).

(56) References Cited

OTHER PUBLICATIONS

Luten et al., "Biodegradable polymers as non-viral carriers for plasmid DNA delivery," J. Controlled Release, 126(2): 97-110 (2008).
Ohno et al., "PPARγ agonists induce a white-to-brown fat conversion through stabilization of PRDM16 protein," Cell Metab. 15, 395-404 (2012).
Park et al., "Bioreducible polyspermine as less toxic and efficient gene carrier," Polym. Adv. Technol. 25, 545-551 (2014).
Park et al., "Combinatorial gene construct and non-viral delivery for anti-obesity in diet-induced obese mice," J. Control. Release 207, 154-162 (2015).
Puigserver et al., "A cold-inducible coactivator of nuclear receptors linked to adaptive thermogenesis," Cell 92, 829-839 (1998).
Pyrzak et al., "Brown Adipose Tissue and Browning Agents: Irisin and FGF21 in the Development of Obesity in Children and Adolescents," Adv. Exp. Med. Biol., 866: 25-34 (2015).
Radcliffe et al., "Multiple gene products from a single vector: 'Self-cleaving' 2A peptides," Gene Therapy, 11: 1673-1674 (2004).
Ravussin et al., "Enhanced weight loss with pramlintide/metreleptin: an integrated neurohormonal approach to obesity pharmacotherapy," Obesity 17, 1736-1743 (2009).
Rivera et al., "Human-IAPP disrupts the autophagy/lysosomal pathway in pancreatic b-cells: protective role of p62-positive cytoplasmic inclusions," Cell Death and Differentiation, Sep. 3, 2010, vol. 18, pp. 415-426.
Roth et al., "Leptin responsiveness restored by amylin agonism in diet-induced obesity: evidence from nonclinical and clinical studies," Proc. Natl. Acad. Sci. U.S.A. 105, 7257-7262 (2008).
Roujeau et al., "New pharmacological perspectives for the leptin receptor in the treatment of obesity," Front. Endocrinol. 5, (2014).
Sadry et al., "Emerging combinatorial hormone therapies for the treatment of obesity and T2DM," Nat. Rev. Endocrinol. 9, 425-433 (2013).
Seale et al., "Prdm16 determines the thermogenic program of subcutaneous white adipose tissue in mice," J. Clin. Invest. 121, 96-105 (2011).
Shiryaev et al., "Targeting host cell furin proprotein convertases as a therapeutic strategy against bacterial toxins and viral pathogens," The Journal of Biological Chemistry, 282(29): 20847-53 (2007).
Soding, "Protein homology detection by HMM-HMM comparison," Bioinformatics, 21(7): 951-960 (2005).
Song et al., "A solid-phase PEGylation strategy for protein therapeutics using a potent FGF21 analog," Biomaterials 35, 5206-5215 (2014).
Szymczak et al., "Development of 2A peptide-based strategies in the design of multicistronic vectors," Expert Opin. Biol. Ther. 5, 627-638 (2005).
Thomas, "Furin at the cutting edge: from protein traffic to embryogenesis and disease," Nature Reviews Molecular Cell Biology, 3(10): 753-66 (2002).
Trayhurn et al., "Physiological role of adipose tissue: white adipose tissue as an endocrine and secretory organ," Proc. Nutr. Soc. 60(3): 329-39 (2001).
Trevaskis et al., "Interaction of leptin and amylin in the long-term maintenance of weight loss in diet-induced obese rats," Obesity 18, 21-26 (2010).
Uldry et al., "Complementary action of the PGC-1 coactivators in mitochondrial biogenesis and brown fat differentiation," Cell Metab. 3, 333-341 (2006).
Urban-Klein et al., "RNAi-mediated gene-targeting through systemic application of polyethylenimine (PEI)-complexed siRNA in vivo," Gene Ther. 12, 461-466 (2005).
Wang et al. "2A self-cleaving peptide-based multi-gene expression system in the silkworm Bombyxmori," Scientific Reports. Nov. 5, 2015, vol. 5, No. 16273, pp. 1-10.
Wu et al., "Thermogenic Capacity Is Antagonistically Regulated in Classical Brown and White Subcutaneous Fat Depots by High Fat Diet and Endurance Training in Rats," J. Biol. Chem. 5,289(49): 34129-40 (2014).
Xu et al., "Pentablock copolymers of poly(ethylene glycol), poly((2-dimethyl amino)ethyl methacrylate) and poly(2-hydroxyethyl methacrylate) from consecutive atom transfer radical polymerizations for non-viral gene delivery," Biomaterials 29, 3023-3033 (2008).
Yin et al., "Non-viral vectors for gene-based therapy," Nature Rev. Genet. 15, 541-555 (2014).
Zhang et al., "Neuronal receptor activity-modifying protein 1 promotes energy expenditure in mice," Diabetes 60, 1063-1071 (2011).
Zhu et al., "In-fusion assembly: seamless engineering of multidomain fusion proteins, modular vectors, and mutations," Biotechniques 43, 354-359 (2007).

* cited by examiner

C

D

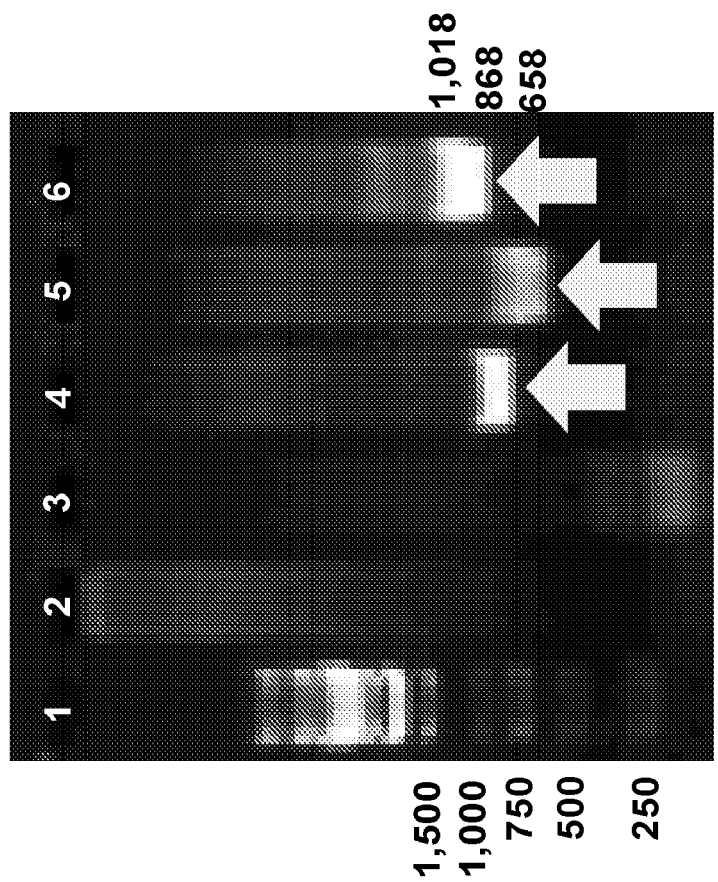

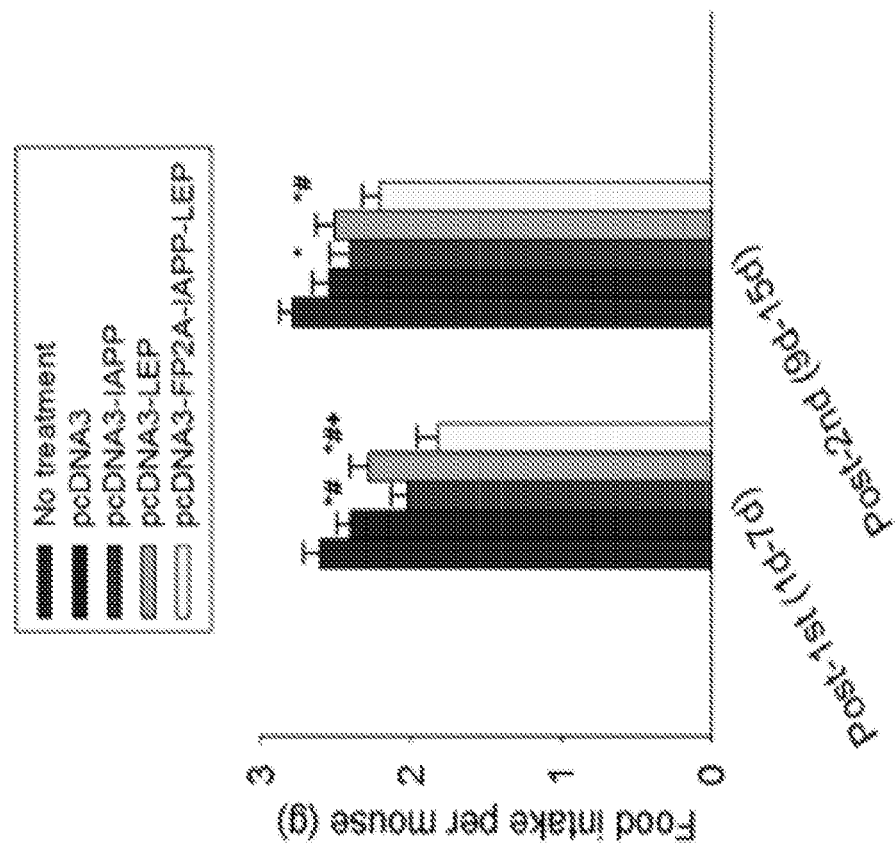

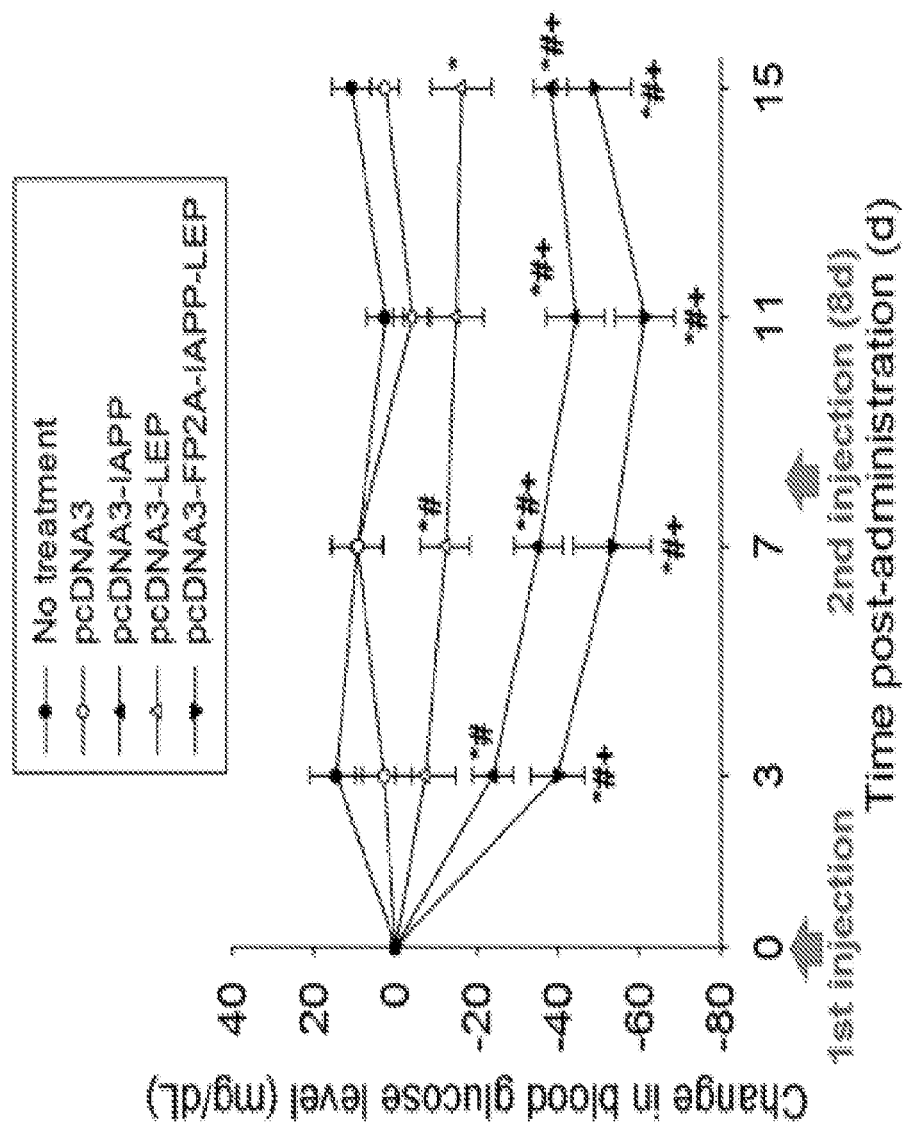

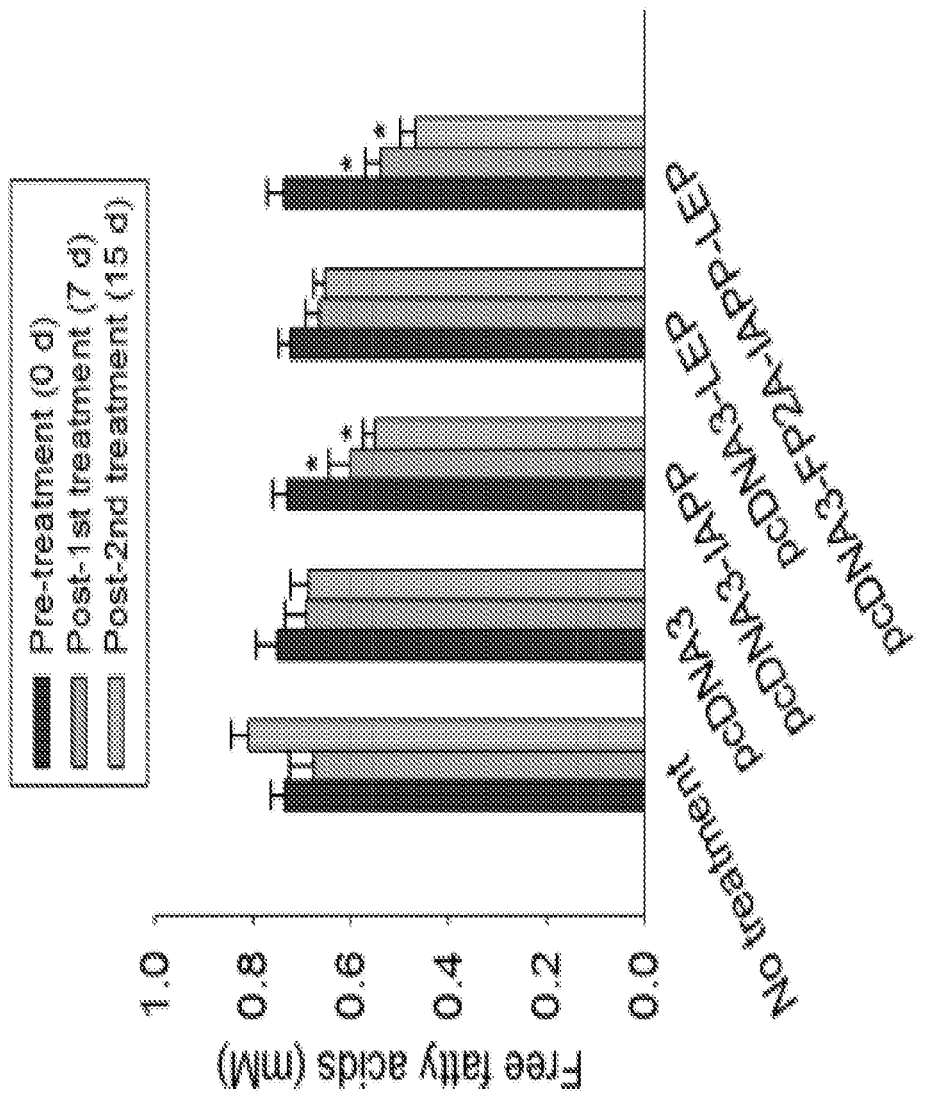

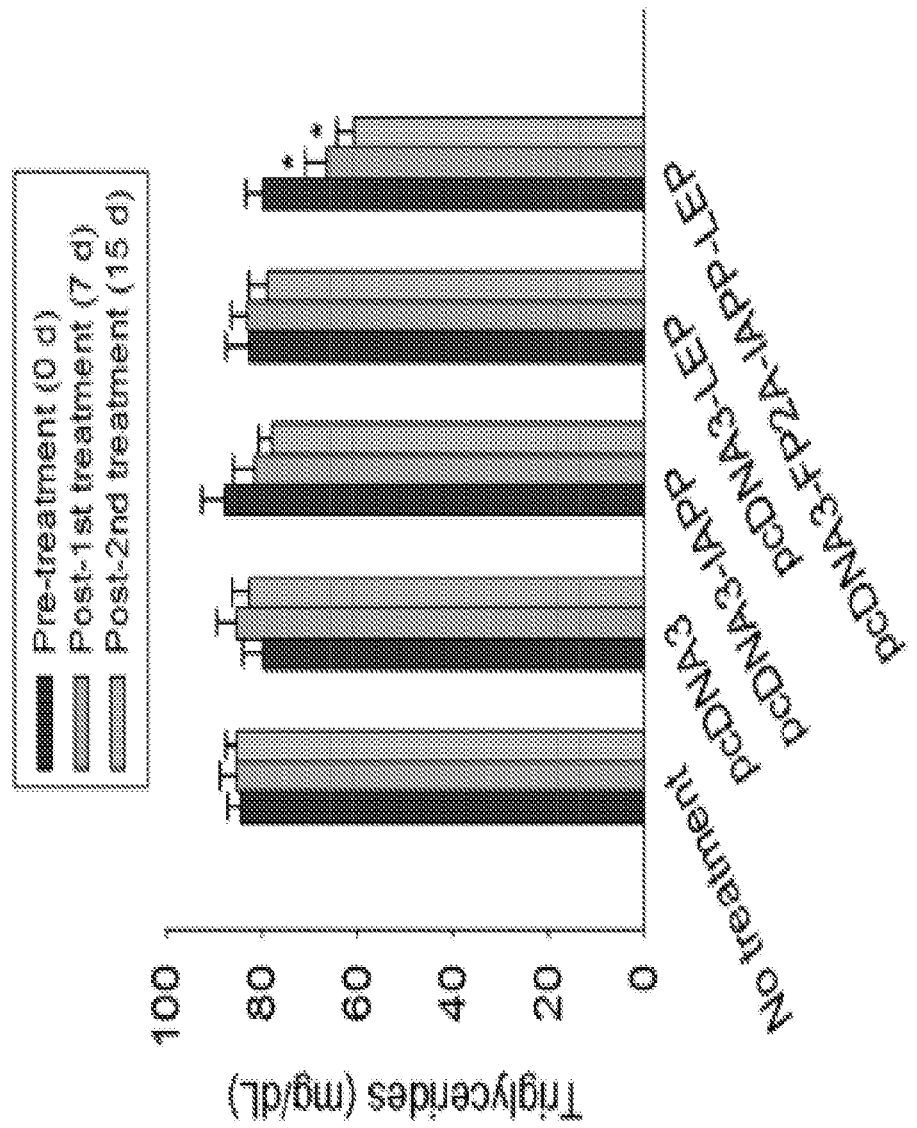

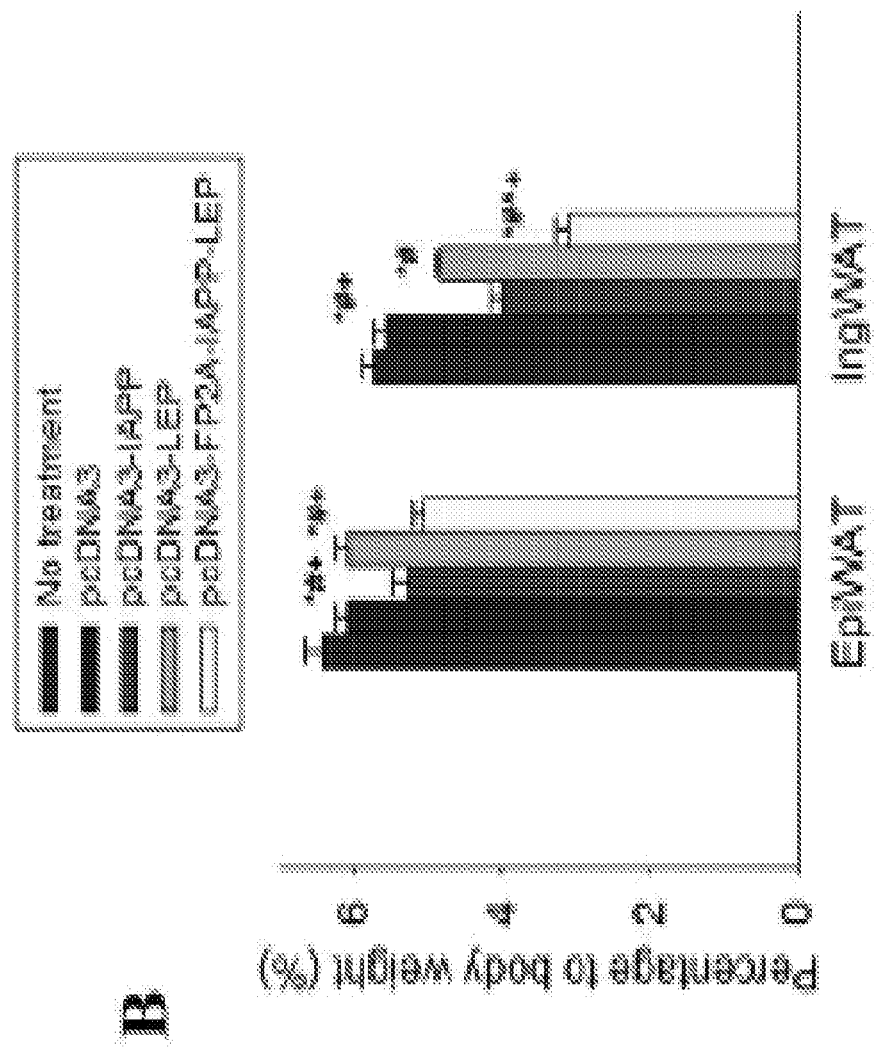

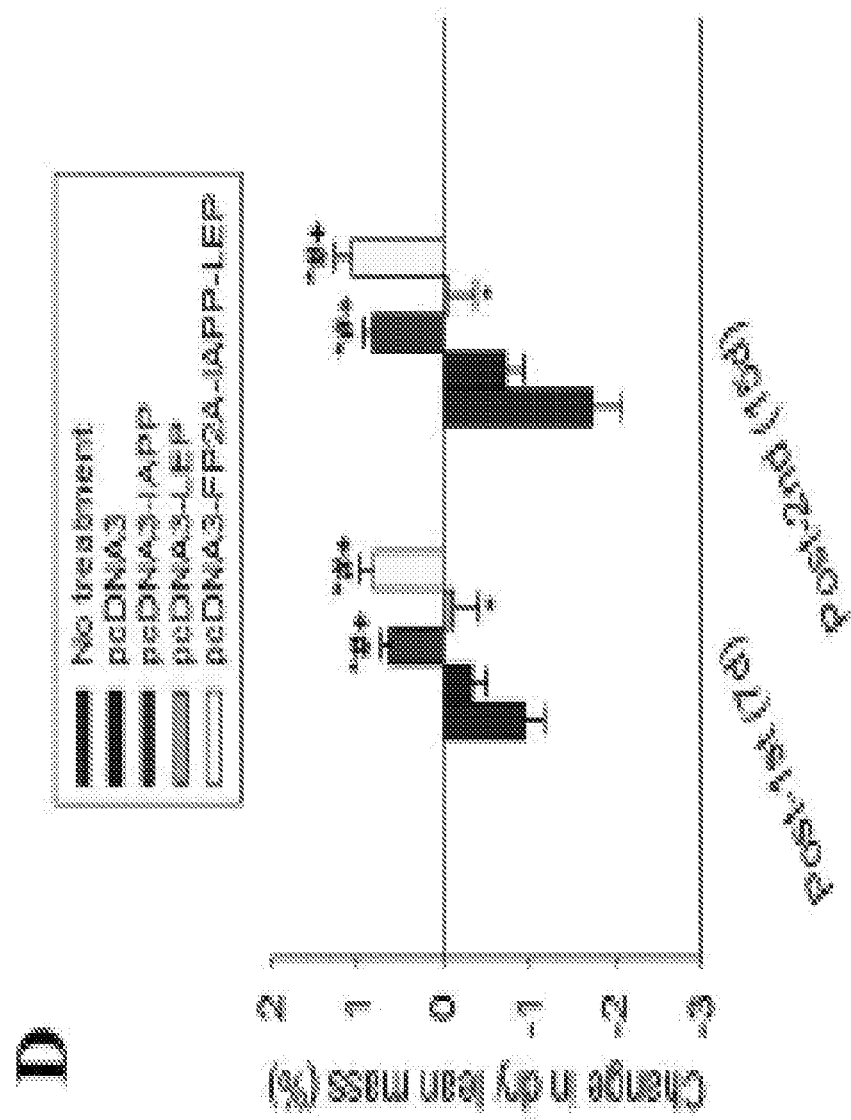

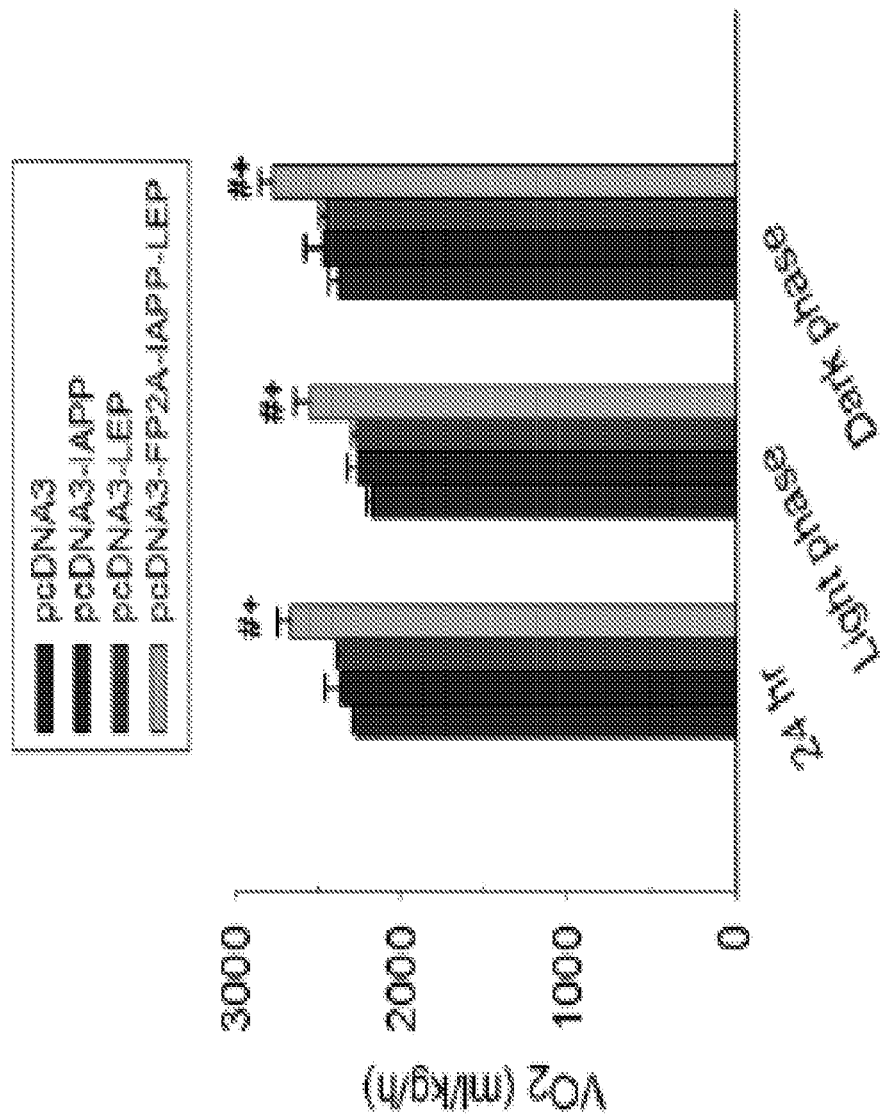

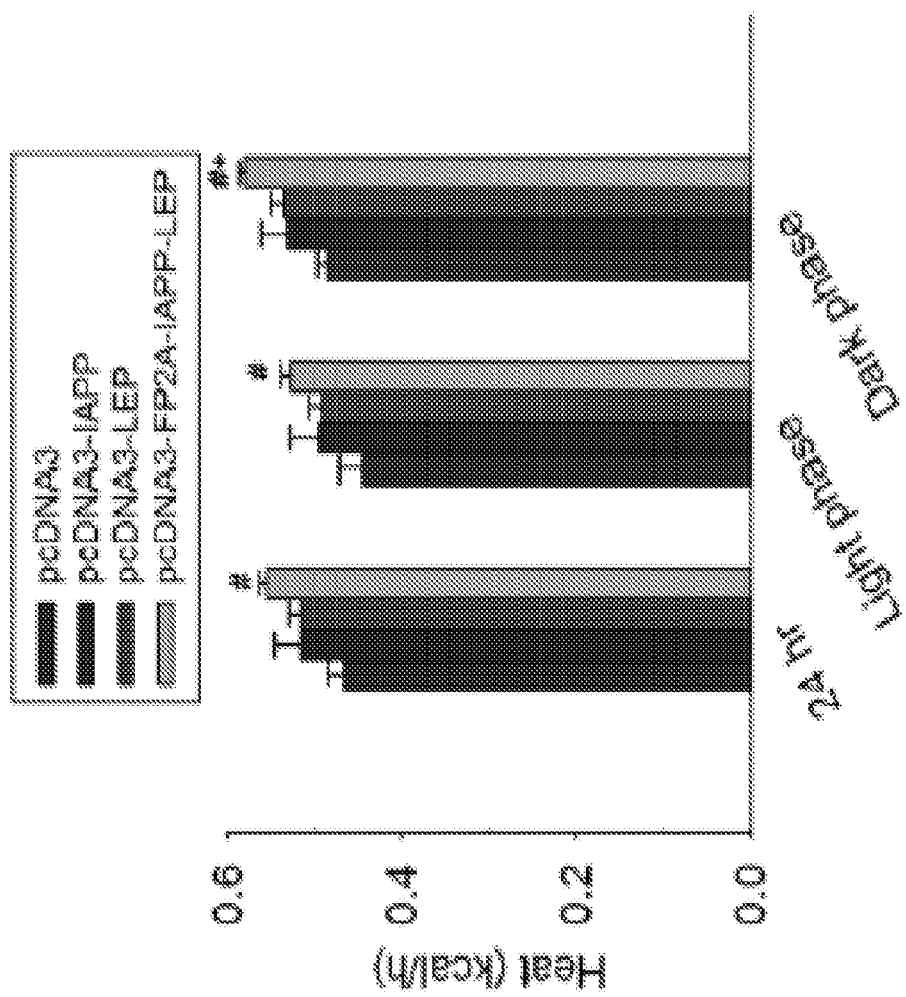

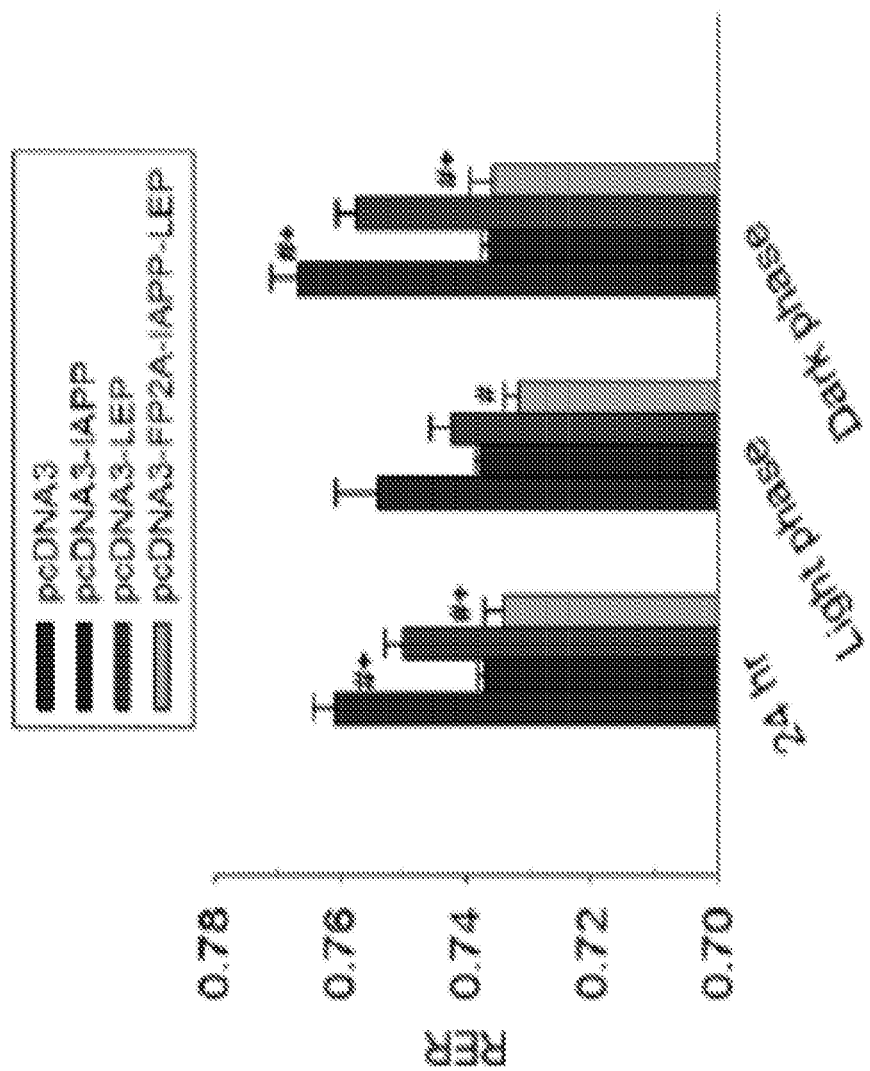

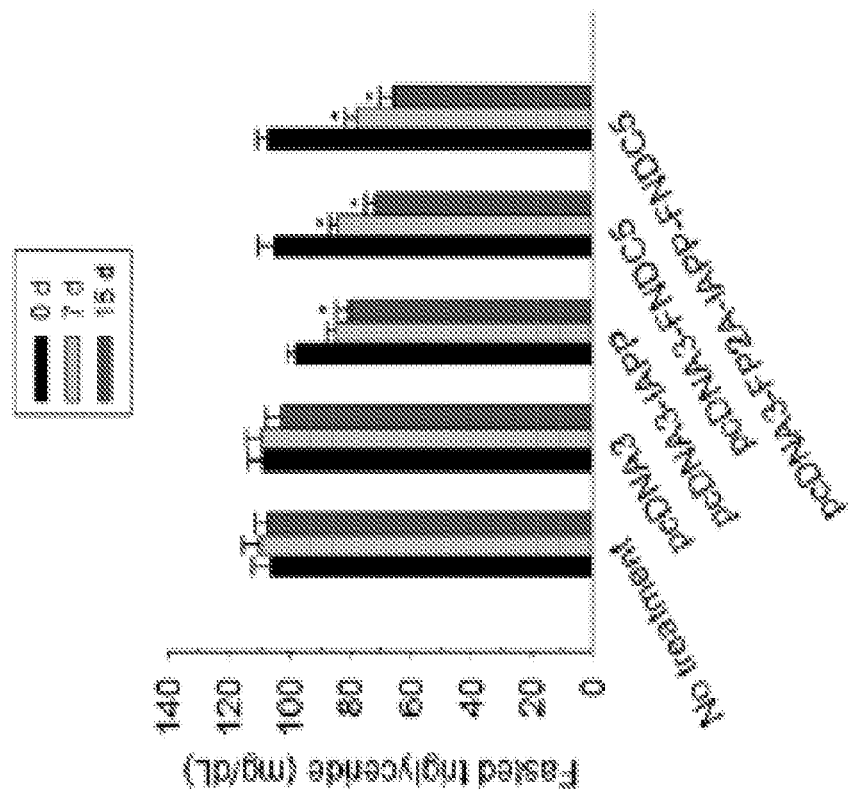

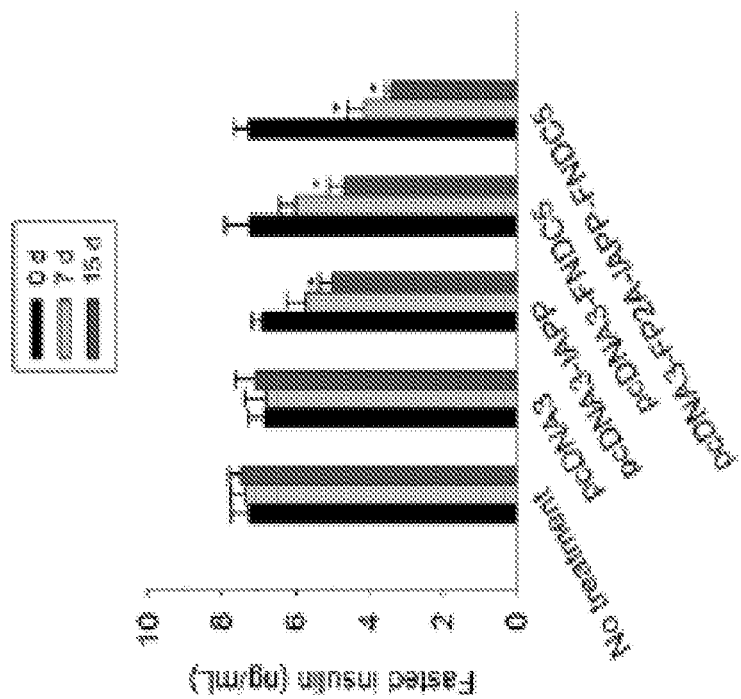

SEQUENCE LISTING

```
<160> NUMBER OF SEQ ID NOS: 19

<210> SEQ ID NO 1
<211> LENGTH: 279
<212> TYPE: DNA
<213> ORGANISM: Mus musculus

<400> SEQUENCE: 1
atgatgtgca tctccaaact gccagctgtc ctcctcatcc tctctgtggc actgaaccac      60
ttgagagcta cacctgtcag aagtggtagc aaccctcaga tggacaaacg gaagtgcaac     120
acggccacgt gtgccacaca acgcctggca aactttttgg ttcgttccag caacaacctt    180
ggtccagtcc tcccaccaac caacgtggga tcgaatacat atggcaagag gaatgcggca    240
ggggatccaa atagggaatc cttggatttc ttactcgtt                            279

<210> SEQ ID NO 2
<211> LENGTH: 93
<212> TYPE: PRT
<213> ORGANISM: Mus musculus

<400> SEQUENCE: 2

Met Met Cys Ile Ser Lys Leu Pro Ala Val Leu Leu Ile Leu Ser Val
1               5                   10                  15

Ala Leu Asn His Leu Arg Ala Thr Pro Val Arg Ser Gly Ser Asn Pro
                20                  25                  30

Gln Met Asp Lys Arg Lys Cys Asn Thr Ala Thr Cys Ala Thr Gln Arg
            35                  40                  45

Leu Ala Asn Phe Leu Val Arg Ser Ser Asn Asn Leu Gly Pro Val Leu
        50                  55                  60

Pro Pro Thr Asn Val Gly Ser Asn Thr Tyr Gly Lys Arg Asn Ala Ala
65                  70                  75                  80

Gly Asp Pro Asn Arg Glu Ser Leu Asp Phe Leu Leu Val
                85                  90

<210> SEQ ID NO 3
<211> LENGTH: 89
<212> TYPE: PRT
<213> ORGANISM: Homo sapiens

<400> SEQUENCE: 3
```

Met Gly Ile Leu Lys Leu Gln Val Phe Leu Ile Val Leu Ser Val Ala
1               5                   10                  15

Leu Asn His Leu Lys Ala Thr Pro Ile Glu Ser His Gln Val Glu Lys
            20                  25                  30

Arg Lys Cys Asn Thr Ala Thr Cys Ala Thr Gln Arg Leu Ala Asn Phe
        35                  40                  45

Leu Val His Ser Ser Asn Asn Phe Gly Ala Ile Leu Ser Ser Thr Asn
    50                  55                  60

Val Gly Ser Asn Thr Tyr Gly Lys Arg Asn Ala Val Glu Val Leu Lys
65                  70                  75                  80

Arg Glu Pro Leu Asn Tyr Leu Pro Leu
                85

<210> SEQ ID NO 4
<211> LENGTH: 501
<212> TYPE: DNA
<213> ORGANISM: Mus musculus

<400> SEQUENCE: 4
atgtgctgga gacccctgtg tcggttcctg tggctttggt cctatctgtc ttatgttcaa     60
gcagtgccta tccagaaagt ccaggatgac accaaaaccc tcatcaagac cattgtcacc    120
aggatcaatg acatttcaca cacgcagtcg gtatccgcca agcagagggt cactggcttg    180
gacttcattc ctgggcttca ccccattctg agtttgtcca agatggacca gactctggca    240
gtctatcaac aggtcctcac cagcctgcct tcccaaaatg tgctgcagat agccaatgac    300
ctggagaatc tccgagacct cctccatctg ctggccttct ccaagagctg ctccctgcct    360
cagaccagtg gcctgcagaa gccagagagc ctggatggcg tcctggaagc ctcactctac    420
tccacagagg tggtggcttt gagcaggctg cagggctctc tgcaggacat tcttcaacag    480
ttggatgtta gccctgaatg c                                              501

<210> SEQ ID NO 5
<211> LENGTH: 167
<212> TYPE: PRT
<213> ORGANISM: Mus musculus

<400> SEQUENCE: 5

Met Cys Trp Arg Pro Leu Cys Arg Phe Leu Trp Leu Trp Ser Tyr Leu
1               5                   10                  15

Ser Tyr Val Gln Ala Val Pro Ile Gln Lys Val Gln Asp Asp Thr Lys
            20                  25                  30

Thr Leu Ile Lys Thr Ile Val Thr Arg Ile Asn Asp Ile Ser His Thr
        35                  40                  45

Gln Ser Val Ser Ala Lys Gln Arg Val Thr Gly Leu Asp Phe Ile Pro
    50                  55                  60

Gly Leu His Pro Ile Leu Ser Leu Ser Lys Met Asp Gln Thr Leu Ala
65                  70                  75                  80

Val Tyr Gln Gln Val Leu Thr Ser Leu Pro Ser Gln Asn Val Leu Gln
                85                  90                  95

Ile Ala Asn Asp Leu Glu Asn Leu Arg Asp Leu Leu His Leu Leu Ala
            100                 105                 110

Phe Ser Lys Ser Cys Ser Leu Pro Gln Thr Ser Gly Leu Gln Lys Pro
        115                 120                 125

Glu Ser Leu Asp Gly Val Leu Glu Ala Ser Leu Tyr Ser Thr Glu Val
    130                 135                 140

Glu Ala Leu Ser Arg Leu Gln Gly Ser Leu Gln Asp Ile Leu Gln Gln
145                 150                 155                 160

Leu Asp Val Ser Pro Glu Cys
                165

<210> SEQ ID NO 6
<211> LENGTH: 167
<212> TYPE: PRT
<213> ORGANISM: Homo sapiens

<400> SEQUENCE: 6

Met His Trp Gly Thr Leu Cys Gly Phe Leu Trp Leu Trp Pro Tyr Leu
1               5                   10                  15

Phe Tyr Val Gln Ala Val Pro Ile Gln Lys Val Gln Asp Asp Thr Lys
                20                  25                  30

Thr Leu Ile Lys Thr Ile Val Thr Arg Ile Asn Asp Ile Ser His Thr
            35                  40                  45

Gln Ser Val Ser Ser Lys Gln Lys Val Thr Gly Leu Asp Phe Ile Pro
    50                  55                  60

Gly Leu His Pro Ile Leu Thr Leu Ser Lys Met Asp Gln Thr Leu Ala
65                  70                  75                  80

Val Tyr Gln Gln Ile Leu Thr Ser Met Pro Ser Arg Asn Val Ile Gln
                85                  90                  95

Ile Ser Asn Asp Leu Glu Asn Leu Arg Asp Leu Leu His Val Leu Ala
            100                 105                 110

Phe Ser Lys Ser Cys His Leu Pro Trp Ala Ser Gly Leu Glu Thr Leu
        115                 120                 125

Asp Ser Leu Gly Gly Val Leu Glu Ala Ser Gly Tyr Ser Thr Glu Val
    130                 135                 140

Val Ala Leu Ser Arg Leu Gln Gly Ser Leu Gln Asp Met Leu Trp Gln
145                 150                 155                 160

Leu Asp Leu Ser Pro Gly Cys
                165

<210> SEQ ID NO 7
<211> LENGTH: 627
<212> TYPE: DNA
<213> ORGANISM: Mus musculus

<400> SEQUENCE: 7
atgcccccag gccgtgcgc ctggccgccc cgcgccgcgc tccgcctgtg gctaggctgc      60
gtctgcttcg cgctggtgca ggcggacagc ccctcagccc ctgtgaacgt gaccgtccgg    120
cacctcaagg ccaactctgc cgtggtcagc tgggatgtcc tggaggatga agtggtcatt    180
ggctttgcca tctctcagca gaagaaggat gtgcggatgc tccggttcat tcaggaggtg    240
aacaccacca cccggtcctg cgctctctgg gacctggagg aggacacaga atatatcgtc    300
catgtgcagg ccatctccat ccagggacag agcccagcca gtgagcctgt gctcttcaag    360
accccacgcg aggctgaaaa gatggcctca agaacaaag atgaggtgac catgaaggag     420
atggggagga accagcagct gcgaacgggg gaggtgctga tcattgttgt ggtcctcttc    480
atgtgggcag gtgttatagc tctcttctgc cgccagtatg atatcatcaa ggacaacgag    540
cccaataaca acaaggagaa aaccaagagc gcatcagaaa ccagcacacc ggagcatcag    600
ggtgggggtc tcctccgcag caagata                                        627

```
<210> SEQ ID NO 8
<211> LENGTH: 209
<212> TYPE: PRT
<213> ORGANISM: Mus musculus

<400> SEQUENCE: 8

Met Pro Pro Gly Pro Cys Ala Trp Pro Pro Arg Ala Ala Leu Arg Leu
1               5                   10                  15

Trp Leu Gly Cys Val Cys Phe Ala Leu Val Gln Ala Asp Ser Pro Ser
            20                  25                  30

Ala Pro Val Asn Val Thr Val Arg His Leu Lys Ala Asn Ser Ala Val
        35                  40                  45

Val Ser Trp Asp Val Leu Glu Asp Glu Val Val Ile Gly Phe Ala Ile
    50                  55                  60

Ser Gln Gln Lys Lys Asp Val Arg Met Leu Arg Phe Ile Gln Glu Val
65                  70                  75                  80

Asn Thr Thr Thr Arg Ser Cys Ala Leu Trp Asp Leu Glu Glu Asp Thr
                85                  90                  95

Glu Tyr Ile Val His Val Gln Ala Ile Ser Ile Gln Gly Gln Ser Pro
            100                 105                 110

Ala Ser Glu Pro Val Leu Phe Lys Thr Pro Arg Glu Ala Glu Lys Met
        115                 120                 125

Ala Ser Lys Asn Lys Asp Glu Val Thr Met Lys Glu Met Gly Arg Asn
    130                 135                 140

Gln Gln Leu Arg Thr Gly Glu Val Leu Ile Ile Val Val Leu Phe
145                 150                 155                 160

Met Trp Ala Gly Val Ile Ala Leu Phe Cys Arg Gln Tyr Asp Ile Ile
                165                 170                 175

Lys Asp Asn Glu Pro Asn Asn Asn Lys Glu Lys Thr Lys Ser Ala Ser
            180                 185                 190

Glu Thr Ser Thr Pro Glu His Gln Gly Gly Gly Leu Leu Arg Ser Lys
        195                 200                 205

Ile

<210> SEQ ID NO 9
<211> LENGTH: 153
<212> TYPE: PRT
<213> ORGANISM: Homo sapiens

<400> SEQUENCE: 9

Met Leu Arg Phe Ile Gln Glu Val Asn Thr Thr Thr Arg Ser Cys Ala
1               5                   10                  15

Leu Trp Asp Leu Glu Glu Asp Thr Glu Tyr Ile Val His Val Gln Ala
            20                  25                  30

Ile Ser Ile Gln Gly Gln Ser Pro Ala Ser Glu Pro Val Leu Phe Lys
        35                  40                  45

Thr Pro Arg Glu Ala Glu Lys Met Ala Ser Lys Asn Lys Asp Glu Val
    50                  55                  60

Thr Met Lys Glu Met Gly Arg Asn Gln Gln Leu Arg Thr Gly Glu Val
65                  70                  75                  80

Leu Ile Ile Val Val Leu Phe Met Trp Ala Gly Val Ile Ala Leu
                85                  90                  95

Phe Cys Arg Gln Tyr Asp Ile Ile Lys Asp Asn Glu Pro Asn Asn Asn
            100                 105                 110

Lys Glu Lys Thr Lys Ser Ala Ser Glu Thr Ser Thr Pro Glu His Gln
        115                 120                 125
```

Gly Gly Gly Leu Leu Arg Ser Lys Val Arg Ala Arg Pro Gly Pro Gly
            130                 135                 140

Trp Ala Thr Leu Cys Leu Met Leu Trp
145                 150

<210> SEQ ID NO 10
<211> LENGTH: 6286
<212> TYPE: DNA
<213> ORGANISM: Artificial Sequence
<220> FEATURE:
<223> OTHER INFORMATION: Synthetic Oligonucleotide

<400> SEQUENCE: 10

| | |
|---|---|
| gacggatcgg gagatctccc gatccctat ggtcgactct cagtacaatc tgctctgatg | 60 |
| ccgcatagtt aagccagtat ctgctccctg cttgtgtgtt ggaggtcgct gagtagtgcg | 120 |
| cgagcaaaat ttaagctaca acaaggcaag gcttgaccga caattgcatg aagaatctgc | 180 |
| ttagggttag gcgttttgcg ctgcttcgcg atgtacgggc cagatatacg cgttgacatt | 240 |
| gattattgac tagttattaa tagtaatcaa ttacgggtc attagttcat agcccatata | 300 |
| tggagttccg cgttacataa cttacggtaa atggcccgcc tggctgaccg cccaacgacc | 360 |
| cccgcccatt gacgtcaata atgacgtatg ttcccatagt aacgccaata gggactttcc | 420 |
| attgacgtca atgggtggac tatttacggt aaactgccca cttggcagta catcaagtgt | 480 |
| atcatatgcc aagtacgccc cctattgacg tcaatgacgg taaatggccc gcctggcatt | 540 |
| atgcccagta catgacctta tgggactttc tacttggca gtacatctac gtattagtca | 600 |
| tcgctattac catggtgatg cggttttggc agtacatcaa tgggcgtgga tagcggtttg | 660 |
| actcacgggg atttccaagt ctccacccca ttgacgtcaa tgggagtttg ttttggcacc | 720 |
| aaaatcaacg ggactttcca aaatgtcgta acaactccgc cccattgacg caaatgggcg | 780 |
| gtaggcgtgt acggtgggag gtctatataa gcagagctct ctggctaact agagaaccca | 840 |
| ctgcttactg gcttatcgaa attaatacga ctcactatag ggagacccaa gcttggtacc | 900 |
| gagctcggat ccagacatga tgtgcatctc caaactgcca gctgtcctcc tcatcctctc | 960 |
| tgtggcactg aaccacttga gagctacacc tgtcagaagt ggtagcaacc ctcagatgga | 1020 |
| caaacggaag tgcaacacgg ccacgtgtgc cacacaacgc ctggcaaact ttttggttcg | 1080 |
| ttccagcaac aaccttggtc cagtcctccc accaaccaac gtgggatcga atacatatgg | 1140 |
| caagaggaat gcggcagggg atccaaatag ggaatccttg gatttcttac tcgttcgcgc | 1200 |
| aaaaagggga tccggagcca cgaacttctc tctgttaaag caagcaggag atgttgaaga | 1260 |
| aaaccccggg cctatgtgct ggagacccct gtgtcggttc ctgtggcttt ggtcctatct | 1320 |
| gtcttatgtt caagcagtgc ctatccagaa agtccaggat gacaccaaaa ccctcatcaa | 1380 |
| gaccattgtc accaggatca atgacatttc acacacgcag tcggtatccg ccaagcagag | 1440 |
| ggtcactggc ttggacttca ttcctgggct tcacccatt ctgagtttgt ccaagatgga | 1500 |
| ccagactctg gcagtctatc aacaggtcct caccagcctg ccttcccaaa atgtgctgca | 1560 |
| gatagccaat gacctggaga atctccgaga cctcctccat ctgctggcct tctccaagag | 1620 |
| ctgctccctg cctcagacca gtggcctgca gaagccagag agcctggatg cgtcctgga | 1680 |
| agcctcactc tactccacag aggtggtggc tttgagcagg ctgcagggct ctctgcagga | 1740 |
| cattcttcaa cagttggatg ttagccctga atgctaagaa ttctgcagat atccatcaca | 1800 |
| ctggcggccg ctcgagcatg catctagagg gccctattct atagtgtcac ctaaatgcta | 1860 |

```
gagctcgctg atcagcctcg actgtgcctt ctagttgcca gccatctgtt gtttgcccct    1920 ccccgtgcc ttccttgacc ctggaaggtg ccactcccac tgtcctttcc taataaaatg    1980
aggaaattgc atcgcattgt ctgagtaggt gtcattctat tctggggggt ggggtggggc    2040
aggacagcaa gggggaggat tgggaagaca atagcaggca tgctggggat gcggtgggct    2100
ctatggcttc tgaggcggaa agaaccagct ggggctctag ggggtatccc cacgcgccct    2160
gtagcggcgc attaagcgcg gcgggtgtgg tggttacgcg cagcgtgacc gctacacttg    2220
ccagcgccct agcgcccgct cctttcgctt tcttcccttc ctttctcgcc acgttcgccg    2280
gctttccccg tcaagctcta atcggggca tccctttagg gttccgattt agtgctttac    2340
ggcacctcga ccccaaaaaa cttgattagg gtgatggttc acgtagtggg ccatcgccct    2400
gatagacggt ttttcgccct tgacgttgg agtccacgtt ctttaatagt ggactcttgt    2460
tccaaactgg aacaacactc aaccctatct cggtctattc ttttgattta agggattt    2520 tggggatttc ggcctattgg ttaaaaaatg agctgattta acaaaatttt aacgcgaatt    2580
aattctgtgg aatgtgtgtc agttagggtg tggaaagtcc ccaggctccc caggcaggca    2640
gaagtatgca aagcatgcat ctcaattagt cagcaaccag gtgtggaaag tccccaggct    2700
ccccagcagg cagaagtatg caaagcatgc atctcaatta gtcagcaacc atagtcccgc    2760
ccctaactcc gcccatcccg ccctaactc cgcccagttc cgcccattct ccgccccatg    2820
gctgactaat tttttttatt tatgcagagg ccgaggccgc ctctgcctct gagctattcc    2880
agaagtagtg aggaggcttt tttggaggcc taggcttttg caaaaagctc ccgggagctt    2940
gtatatccat tttcggatct gatcaagaga caggatgagg atcgtttcgc atgattgaac    3000
aagatggatt gcacgcaggt tctccggccg cttgggtgga gaggctattc ggctatgact    3060
gggcacaaca gacaatcggc tgctctgatg ccgccgtgtt ccggctgtca gcgcaggggc    3120
gcccggttct ttttgtcaag accgacctgt ccggtgccct gaatgaactg caggacgagg    3180
cagcgcggct atcgtggctg gccacgacgg gcgttccttg cgcagctgtg ctcgacgttg    3240
tcactgaagc gggaagggac tggctgctat tgggcgaagt gccggggcag gatctcctgt    3300
catctcacct tgctcctgcc gagaaagtat ccatcatggc tgatgcaatg cggcggctgc    3360
atacgcttga tccggctacc tgcccattcg accaccaagc gaaacatcgc atcgagcgag    3420
cacgtactcg gatggaagcc ggtcttgtcg atcaggatga tctggacgaa gagcatcagg    3480
ggctcgcgcc agccgaactg ttcgccaggc tcaaggcgcg catgcccgac ggcgaggatc    3540
tcgtcgtgac ccatggcgat gcctgcttgc cgaatatcat ggtggaaaat ggccgctttt    3600
ctggattcat cgactgtggc cggctgggtg tggcggaccg ctatcaggac atagcgttgg    3660
ctacccgtga tattgctgaa gagcttggcg gcgaatgggc tgaccgcttc ctcgtgcttt    3720
acggtatcgc cgctcccgat tcgcagcgca tcgccttcta tcgccttctt gacgagttct    3780
tctgagcggg actctgggt tcgaaatgac cgaccaagcg acgcccaacc tgccatcacg    3840
agatttcgat tccaccgccg ccttctatga aggttgggc ttcggaatcg ttttccggga    3900
cgccggctgg atgatcctcc agcgcgggga tctcatgctg gagttcttcg cccaccccaa    3960
cttgtttatt gcagcttata atggttacaa ataaagcaat agcatcacaa atttcacaaa    4020 taaagcatt ttttcactgc attctagttg tggtttgtcc aaactcatca atgtatctta    4080
tcatgtctgt ataccgtcga cctctagcta gagcttggcg taatcatggt catagctgtt    4140
tcctgtgtga aattgttatc cgctcacaat tccacacaac atacgagccg aagcataaa    4200 gtgtaaagcc tggggtgcct aatgagtgag ctaactcaca ttaattgcgt tgcgctcact    4260
```

```
gcccgctttc cagtcgggaa acctgtcgtg ccagctgcat taatgaatcg gccaacgcgc    4320
ggggagaggc ggtttgcgta ttgggcgctc ttccgcttcc tcgctcactg actcgctgcg    4380
ctcggtcgtt cggctgcggc gagcggtatc agctcactca aaggcggtaa tacggttatc    4440
cacagaatca ggggataacg caggaaagaa catgtgagca aaaggccagc aaaaggccag    4500
gaaccgtaaa aaggccgcgt tgctggcgtt tttccatagg ctccgccccc ctgacgagca    4560
tcacaaaaat cgacgctcaa gtcagaggtg gcgaaacccg acaggactat aaagatacca    4620
ggcgtttccc cctggaagct ccctcgtgcg ctctcctgtt ccgaccctgc cgcttaccgg    4680
atacctgtcc gcctttctcc cttcgggaag cgtggcgctt tctcaatgct cacgctgtag    4740
gtatctcagt tcggtgtagg tcgttcgctc caagctgggc tgtgtgcacg aaccccccgt    4800
tcagcccgac cgctgcgcct tatccggtaa ctatcgtctt gagtccaacc cggtaagaca    4860
cgacttatcg ccactggcag cagccactgg taacaggatt agcagagcga ggtatgtagg    4920
cggtgctaca gagttcttga agtggtggcc taactacggc tacactagaa ggacagtatt    4980
tggtatctgc gctctgctga agccagttac cttcggaaaa agagttggta gctcttgatc    5040
cggcaaacaa accaccgctg gtagcggtgg tttttttgtt tgcaagcagc agattacgcg    5100
cagaaaaaaa ggatctcaag aagatccttt gatcttttct acggggtctg acgctcagtg    5160
gaacgaaaac tcacgttaag ggattttggt catgagatta tcaaaaagga tcttaccta    5220 gatccttta aattaaaaat gaagttttaa atcaatctaa agtatatatg agtaaacttg    5280
gtctgacagt taccaatgct taatcagtga ggcacctatc tcagcgatct gtctatttcg    5340
ttcatccata gttgcctgac tccccgtcgt gtagataact acgatacggg agggcttacc    5400
atctggcccc agtgctgcaa tgataccgcg agacccacgc tcaccggctc cagatttatc    5460
agcaataaac cagccagccg gaagggccga gcgcagaagt ggtcctgcaa ctttatccgc    5520
ctccatccag tctattaatt gttgccggga agctagagta agtagttcgc cagttaatag    5580
tttgcgcaac gttgttgcca ttgctacagg catcgtggtg tcacgctcgt cgtttggtat    5640
ggcttcattc agctccggtt cccaacgatc aaggcgagtt acatgatccc ccatgttgtg    5700
caaaaaagcg gttagctcct tcggtcctcc gatcgttgtc agaagtaagt tggccgcagt    5760
gttatcactc atggttatgg cagcactgca taattctctt actgtcatgc catccgtaag    5820
atgcttttct gtgactggtg agtactcaac caagtcattc tgagaatagt gtatgcggcg    5880
accgagttgc tcttgcccgg cgtcaatacg ggataatacc gcgccacata gcagaacttt    5940
aaaagtgctc atcattggaa aacgttcttc ggggcgaaaa ctctcaagga tcttaccgct    6000
gttgagatcc agttcgatgt aacccactcg tgcacccaac tgatcttcag catcttttac    6060
tttcaccagc gtttctgggt gagcaaaaac aggaaggcaa aatgccgcaa aaagggaat    6120 aagggcgaca cggaaatgtt gaatactcat actcttcctt tttcaatatt attgaagcat    6180
ttatcagggt tattgtctca tgagcggata catatttgaa tgtatttaga aaataaaca    6240 aatagggtt ccgcgcacat ttccccgaaa agtgccacct gacgtc    6286
```

<210> SEQ ID NO 11
<211> LENGTH: 6536
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1286)..(1286)

<223> OTHER INFORMATION: n is a, c, g, or t

<400> SEQUENCE: 11

```
gacggatcgg gagatctccc gatccctat ggtcgactct cagtacaatc tgctctgatg        60
ccgcatagtt aagccagtat ctgctccctg cttgtgtgtt ggaggtcgct gagtagtgcg       120
cgagcaaaat ttaagctaca acaaggcaag gcttgaccga caattgcatg aagaatctgc       180
ttagggttag gcgttttgcg ctgcttcgcg atgtacgggc cagatatacg cgttgacatt       240
gattattgac tagttattaa tagtaatcaa ttacggggtc attagttcat agcccatata       300
tggagttccg cgttacataa cttacggtaa atggcccgcc tggctgaccg cccaacgacc       360
cccgcccatt gacgtcaata atgacgtatg ttcccatagt aacgccaata gggactttcc       420
attgacgtca atgggtggac tatttacggt aaactgccca cttggcagta catcaagtgt       480
atcatatgcc aagtacgccc cctattgacg tcaatgacgg taaatggccc gcctggcatt       540
atgcccagta catgacctta tgggactttc ctacttggca gtacatctac gtattagtca       600
tcgctattac catggtgatg cggttttggc agtacatcaa tgggcgtgga tagcggtttg       660
actcacgggg atttccaagt ctccacccca ttgacgtcaa tgggagtttg ttttggcacc       720
aaaatcaacg ggacttttcca aaatgtcgta acaactccgc cccattgacg caaatgggcg       780
gtaggcgtgt acggtgggag gtctatataa gcagagctct ctggctaact agagaaccca       840
ctgcttactg gcttatcgaa attaatacga ctcactatag ggagacccaa gcttagaaat       900
gatgtgcatc tccaaactgc cagctgtcct cctcatcctc tctgtggcac tgaaccactt       960
gagagctaca cctgtcagaa gtggtagcaa ccctcagatg acaaacgga agtgcaacac      1020
ggccacgtgt gccacacaac gcctggcaaa cttttttggtt cgttccagca caaccttgg      1080
tccagtcctc ccaccaacca acgtgggatc gaatacatat ggcaagagga atgcggcagg      1140
ggatccaaat agggaatcct tggatttctt actcgttcgc gcaaaaggg gatccggagc      1200
cacgaacttc tctctgttaa agcaagcagg agatgttgaa gaaaaccccg ggcctgcggc      1260
cgccagtgtg atggatatct gcaganttcg cccttggccc aggagtcgcc atgccccag      1320
ggccgtgcgc ctggccgccc cgcgccgcgc tccgcctgtg gctaggctgc gtctgcttcg      1380
cgctggtgca ggcggacagc ccctcagccc ctgtgaacgt gaccgtccgg cacctcaagg      1440
ccaactctgc cgtggtcagc tgggatgtcc tggaggatga agtggtcatt ggctttgcca      1500
tctctcagca gaagaaggat gtgcggatgc tccggttcat tcaggaggtg aacaccacca      1560
cccggtcctg cgctctctgg gacctggagg aggacacaga atatatcgtc catgtgcagg      1620
ccatctccat ccagggacag agcccagcca gtgagcctgt gctcttcaag accccacgcg      1680
aggctgaaaa gatggcctca aagaacaaag atgaggtgac catgaaggag atgggggagga      1740
accagcagct gcgaacgggg gaggtgctga tcattgttgt ggtcctcttc atgtgggcag      1800
gtgttatagc tctcttctgc cgccagtatg atatcatcaa ggacaacgag cccaataaca      1860
acaaggagaa aaccaagagc gcatcagaaa ccagcacacc ggagcatcag ggtgggggtc      1920
tcctccgcag caagatatga tgacacattt acagtgcttg ctctgagcag ctcagaagac      1980
agtagagaat gcgagaggac cttctgacgg tgattgatat tacgaagggc gaattccagc      2040
acactggcgg ccgttactag ttcgagcatg catctagagg gccctattct atagtgtcac      2100
ctaaatgcta gagctcgctg atcagcctcg actgtgcctt ctagttgcca gccatctgtt      2160
gtttgcccct ccccgtgcc ttccttgacc ctggaaggtg ccactcccac tgtcctttcc      2220
taataaaatg aggaaattgc atcgcattgt ctgagtaggt gtcattctat tctggggggt      2280
```

```
ggggtggggc aggacagcaa gggggaggat tgggaagaca atagcaggca tgctggggat      2340
gcggtgggct ctatggcttc tgaggcggaa agaaccagct ggggctctag ggggtatccc      2400
cacgcgccct gtagcggcgc attaagcgcg gcgggtgtgg tggttacgcg cagcgtgacc      2460
gctacacttg ccagcgccct agcgcccgct cctttcgctt tcttcccttc ctttctcgcc      2520
acgttcgccg gctttccccg tcaagctcta atcggggca tccctttagg gttccgattt      2580
agtgctttac ggcacctcga ccccaaaaaa cttgattagg gtgatggttc acgtagtggg      2640
ccatcgccct gatagacggt ttttcgccct ttgacgttgg agtccacgtt ctttaatagt      2700
ggactcttgt tccaaactgg aacaacactc aaccctatct cggtctattc ttttgattta      2760
taagggattt tggggatttc ggcctattgg ttaaaaaatg agctgattta acaaaaattt      2820
aacgcgaatt aattctgtgg aatgtgtgtc agttagggtg tggaaagtcc ccaggctccc      2880
caggcaggca gaagtatgca aagcatgcat ctcaattagt cagcaaccag gtgtggaaag      2940
tccccaggct ccccagcagg cagaagtatg caaagcatgc atctcaatta gtcagcaacc      3000
atagtcccgc ccctaactcc gcccatcccg ccctaactc cgcccagttc cgcccattct      3060
ccgccccatg gctgactaat ttttttatt tatgcagagg ccgaggccgc ctctgcctct      3120
gagctattcc agaagtagtg aggaggcttt tttggaggcc taggcttttg caaaaagctc      3180 ccggagctt gtatatccat tttcggatct gatcaagaga caggatgagg atcgtttcgc      3240
atgattgaac aagatggatt gcacgcaggt tctccggccg cttgggtgga gaggctattc      3300
ggctatgact gggcacaaca gacaatcggc tgctctgatg ccgccgtgtt ccggctgtca      3360 gcgcagggc gcccggttct ttttgtcaag accgacctgt ccggtgccct gaatgaactg      3420
caggacgagg cagcgcggct atcgtggctg gccacgacgg gcgttccttg cgcagctgtg      3480
ctcgacgttg tcactgaagc gggaagggac tggctgctat gggcgaagt gccggggcag      3540 gatctcctgt catctcacct tgctcctgcc gagaaagtat ccatcatggc tgatgcaatg      3600
cggcggctgc atacgcttga tccggctacc tgcccattcg accaccaagc gaaacatcgc      3660
atcgagcgag cacgtactcg gatgaagccg gtcttgtcg atcaggatga tctggacgaa      3720
gagcatcagg ggctcgcgcc agccgaactg ttcgccaggc tcaaggcgcg catgcccgac      3780
ggcgaggatc tcgtcgtgac ccatggcgat gcctgcttgc cgaatatcat ggtgaaaat      3840 ggccgctttt ctggattcat cgactgtggc cggctgggtg tggcggaccg ctatcaggac      3900
atagcgttgg ctacccgtga tattgctgaa gagcttggcg gcgaatgggc tgaccgcttc      3960
ctcgtgcttt acggtatcgc cgctcccgat tcgcagcgca tcgccttcta tcgccttctt      4020
gacgagttct tctgagcggg actctggggt tcgaaatgac cgaccaagcg acgcccaacc      4080
tgccatcacg agatttcgat tccaccgccg ccttctatga aggttgggc ttcggaatcg      4140 ttttccggga cgccggctgg atgatcctcc agcgcgggga tctcatgctg gagttcttcg      4200 cccacccca cttgtttatt gcagcttata atggttacaa ataaagcaat agcatcacaa      4260
atttcacaaa taaagcattt ttttcactgc attctagttg tggtttgtcc aaactcatca      4320
atgtatctta tcatgtctgt ataccgtcga cctctagcta gagcttggcg taatcatggt      4380
catagctgtt cctgtgtga aattgttatc cgctcacaat tccacacaac atacgagccg      4440
gaagcataaa gtgtaaagcc tggggtgcct aatgagtgag ctaactcaca ttaattgcgt      4500
tgcgctcact gcccgctttc cagtcgggaa acctgtcgtg ccagctgcat taatgaatcg      4560
gccaacgcgc ggggagaggc ggtttgcgta ttgggcgctc ttccgcttcc tcgctcactg      4620
```

-continued

```
actcgctgcg ctcggtcgtt cggctgcggc gagcggtatc agctcactca aaggcggtaa      4680
tacggttatc cacagaatca ggggataacg caggaaagaa catgtgagca aaaggccagc      4740
aaaaggccag gaaccgtaaa aaggccgcgt tgctggcgtt tttccatagg ctccgccccc      4800
ctgacgagca tcacaaaaat cgacgctcaa gtcagaggtg gcgaaacccg acaggactat      4860
aaagatacca ggcgtttccc cctggaagct ccctcgtgcg ctctcctgtt ccgaccctgc      4920
cgcttaccgg atacctgtcc gcctttctcc cttcgggaag cgtggcgctt tctcaatgct      4980
cacgctgtag gtatctcagt tcggtgtagg tcgttcgctc caagctgggc tgtgtgcacg      5040
aaccccccgt tcagcccgac cgctgcgcct tatccggtaa ctatcgtctt gagtccaacc      5100
cggtaagaca cgacttatcg ccactggcag cagccactgg taacaggatt agcagagcga      5160
ggtatgtagg cggtgctaca gagttcttga agtggtggcc taactacggc tacactagaa      5220
ggacagtatt tggtatctgc gctctgctga agccagttac cttcggaaaa agagttggta      5280
gctcttgatc cggcaaacaa accaccgctg gtagcggtgg ttttttttgtt tgcaagcagc      5340 agattacgcg cagaaaaaaa ggatctcaag aagatccttt gatcttttct acggggtctg      5400
acgctcagtg gaacgaaaac tcacgttaag ggattttggt catgagatta tcaaaaagga      5460
tcttcaccta gatccttttta aattaaaaat gaagttttaa atcaatctaa agtatatatg      5520
agtaaacttg gtctgacagt taccaatgct taatcagtga ggcacctatc tcagcgatct      5580
gtctatttcg ttcatccata gttgcctgac tccccgtcgt gtagataact acgatacggg      5640
agggcttacc atctggcccc agtgctgcaa tgataccgcg agacccacgc tcaccggctc      5700
cagatttatc agcaataaac cagccagccg aagggccga gcgcagaagt ggtcctgcaa      5760
ctttatccgc ctccatccag tctattaatt gttgccggga agctagagta agtagttcgc      5820
cagttaatag tttgcgcaac gttgttgcca ttgctacagg catcgtggtg tcacgctcgt      5880
cgtttggtat ggcttcattc agctccggtt cccaacgatc aaggcgagtt acatgatccc      5940
ccatgttgtg caaaaaagcg gttagctcct tcggtcctcc gatcgttgtc agaagtaagt      6000
tggccgcagt gttatcactc atggttatgg cagcactgca taattctctt actgtcatgc      6060
catccgtaag atgcttttct gtgactggtg agtactcaac caagtcattc tgagaatagt      6120
gtatgcggcg accgagttgc tcttgcccgg cgtcaatacg ggataatacc gcgccacata      6180
gcagaacttt aaaagtgctc atcattggaa aacgttcttc ggggcgaaaa ctctcaagga      6240
tcttaccgct gttgagatcc agttcgatgt aacccactcg tgcacccaac tgatcttcag      6300
catcttttac tttcaccagc gtttctgggt gagcaaaaac aggaaggcaa aatgccgcaa      6360
aaaagggaat aagggcgaca cggaaatgtt gaatactcat actcttcctt tttcaatatt      6420
attgaagcat ttatcagggt tattgtctca tgagcggata catatttgaa tgtatttaga      6480
aaaataaaca ataggggtt ccgcgcacat ttccccgaaa agtgccacct gacgtc       6536
```

```
<210> SEQ ID NO 12
<211> LENGTH: 46
<212> TYPE: DNA
<213> ORGANISM: Artificial Sequence
<220> FEATURE:
<223> OTHER INFORMATION: Forward primer

<400> SEQUENCE: 12
gtaccgagct cggatccaga catgatgtgc atctccaaac tgccag                    46

<210> SEQ ID NO 13
<211> LENGTH: 105
```

<212> TYPE: DNA
<213> ORGANISM: Artificial Sequence
<220> FEATURE:
<223> OTHER INFORMATION: Reverse primer

<400> SEQUENCE: 13
aggcccgggg ttttcttcaa catctcctgc ttgctttaac agagagaagt tcgtggctcc    60
ggatccccTt tttgcgcgaa cgagtaagaa atccaaggat tccct                  105

<210> SEQ ID NO 14
<211> LENGTH: 40
<212> TYPE: DNA
<213> ORGANISM: Artificial Sequence
<220> FEATURE:
<223> OTHER INFORMATION: Forward primer

<400> SEQUENCE: 14
gaagaaaacc ccgggcctat gtgctggaga cccctgtgtc                          40

<210> SEQ ID NO 15
<211> LENGTH: 45
<212> TYPE: DNA
<213> ORGANISM: Artificial Sequence
<220> FEATURE:
<223> OTHER INFORMATION: Reverse primer

<400> SEQUENCE: 15
ggatatctgc agaattctta gcattcaggg ctaacatcca actgt                    45

<210> SEQ ID NO 16
<211> LENGTH: 43
<212> TYPE: DNA
<213> ORGANISM: Artificial Sequence
<220> FEATURE:
<223> OTHER INFORMATION: Forward primer

<400> SEQUENCE: 16
gtaccgagct cggatccaga aatgtgctgg agacccctgt gtc                      43

<210> SEQ ID NO 17
<211> LENGTH: 45
<212> TYPE: DNA
<213> ORGANISM: Artificial Sequence
<220> FEATURE:
<223> OTHER INFORMATION: Reverse primer

<400> SEQUENCE: 17
catgctcgag cggccgctta gcattcaggg ctaacatcca actgt                    45

<210> SEQ ID NO 18
<211> LENGTH: 45
<212> TYPE: DNA
<213> ORGANISM: Artificial Sequence
<220> FEATURE:
<223> OTHER INFORMATION: Forward primer

<400> SEQUENCE: 18
agggagaccc aagcttagaa atgatgtgca tctccaaact gccag                    45

<210> SEQ ID NO 19
<211> LENGTH: 121
<212> TYPE: DNA
<213> ORGANISM: Artificial Sequence
<220> FEATURE:
<223> OTHER INFORMATION: Reverse primer

```
<400> SEQUENCE: 19
cgttactagt ggatccaggc ccggggtttt cttcaacatc tcctgcttgc tttaacagag      60
agaagttcgt ggctccggat cccctttttg cgcgaacgag taagaaatcc aaggattccc     120
t                                                                    121
```

COMBINATORIAL GENE CONSTRUCT AND NON-VIRAL DELIVERY FOR ANTI-OBESITY

CROSS REFERENCE TO RELATED APPLICATIONS

This application is a U.S. national stage entry of International Patent Application No. PCT/US2016/024185, filed on Mar. 25, 2016, which claims the benefit of U.S. Provisional Patent Application No. 62/254,745, filed on Nov. 13, 2015, the contents of each of which are fully incorporated by reference herein in their entirety.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 32 Kilobyte 29,155 bytes ASCII (Text) file named "U-5900-026389-9174-US01-SEQ-LIST-05-14-18.txt," created on May 14, 2018.

BACKGROUND OF THE INVENTION

Obesity is a complex and serious threat to global human health and is a risk factor for a variety of conditions, including type 2 diabetes mellitus, cancer, and cardiovascular diseases (Cooke et al., *Nat. Rev. Drug Discovery,* 5: 919-931 (2006) and Harms et al., *Nat. Med.* 19: 1252-1263 (2013)), Since the discovery of adipocyte-derived hormone Leptin (LEP) in 1994 (Haslam et al., *Lancet,* 366: 1197-1209 (2005)), a variety of peptides and their corresponding receptors involved in energy homeostasis have been discovered from the central and peripheral organs. While obesity is commonly thought of as excessive body fat resulting from energy intake exceeding energy expenditure, single gene mutations and/or multiple environmental and psychological factors can contribute to the development of obesity (Kuo et al., *Biomaterials,* 35: 3172-3179 (2014), Contreras et al., *Ann. Med.,* 47: 150-168 (2015), and Boström et al., *Nature,* 481: 463-468 (2012)).

For the management of obesity, a host of single therapies have been investigated. When a particular biological pathway is blocked by a single therapy, however, the body starts to activate alternative compensatory mechanisms to maintain the pre-existing energy balance state, which can lead to resistance to (Uldry et al., *Cell Metab.,* 3: 333-341 (2006)). For example, LEP therapy was once thought to hold great promise in the battle against the obesity epidemic; however, while LEP alone was highly effective in treating LEP-deficient subjects, it showed only limited efficacy in the major obese condition, diet-induced obesity, due to LEP resistance (Seale et al., *J Clin. Invest.,* 121: 96-105 (2011) and Ohno et al., *Cell Metab.,* 15: 395-404 (2012)). To address the disadvantages associated with single protein therapy for obesity, combinatorial strategies have been investigated. For example, LEP resistance was efficiently overcome by continuous or twice-a-day injections of LEP in combination with islet amyloid polypeptide (IAPP) (Uldry et al., supra, *Cell Metab.,* 3: 333-341 (2006), Seale et al., *J. Clin. Invest.,* 121: 96-105 (2011), Ohno et al., *Cell Metab.* 15: 395-404 (2012), Zhang et al., *Diabetes,* 60: 1063-1071 (2011), and Sadry et al., *Nat. Rev. Endocrinol.* 9: 425-433 (2013)). Continuous or twice-a-day administrations of multiple protein therapeutics however, have limited patient compliance, cause irritation at administrations sites, have a high cost burden, and even lead to antibody production against the administered proteins (Ohno et al., *Cell Metab.* 15: 395-404 (2012)).

Accordingly, there is a need for improved compositions and methods for the prevention and treatment of obesity.

BRIEF SUMMARY OF THE INVENTION

The invention provides a plasmid comprising two or more of (a) a nucleic acid sequence encoding islet amyloid polypeptide (IAPP), (b) a nucleic acid sequence encoding leptin (LEP), and (c) a nucleic acid sequence encoding fibronectin type III domain containing 5 (FNDC5). Also provided by the invention are compositions and host cells comprising the plasmid and methods of increasing the metabolic activity in a mammal.

BRIEF DESCRIPTION OF THE DRAWINGS

FIG. 4B is an image depicting the results of in vitro gene expression analysis using RT-PCR and gel electrophoresis. The lanes are indicated as: lane 1 (size marker), lane 2 (PCR amplicon of cDNA from un-treated HEK293T), lane 3 (PCR amplicon of cDNA from pcDNA3-treated HEK293T), lane 4 (PCR amplicon of cDNA from pcDNA3-IAPP-treated HEK293T), lane 5 (PCR amplicon of cDNA from pcDNA3-LEP-treated HEK293T), lane 6 (PCR amplicon of cDNA from pcDNA3-FP2A-IAPP-LEP-treated HEK293T). The numbers on the left are the same as described in FIG. 4A. The numbers on the right (658 bp for lane 5, 868 bp for lane 4, and 1,018 bp for lane 6) are the sizes of PCR products.

FIG. 7 includes graphs illustrating the measurement of blood parameters following lPEI-pDNA polyplex administrations into DIO mice. FIG. 7A shows blood glucose changes (n=7) by lPEI-pDNA polyplexes. *$P<0.05$ vs. no treatment, #$P<0.05$ vs. pcDNA3, +$P<0.05$ vs. pcDNA3-LEP, one-way ANOVA. FIG. 7C shows serum free fatty acid levels (n=6), and FIG. 7D shows serum triglyceride levels (n=6) at pre-treatment, after the first lPEI-pDNA polyplex treatment, and after the second polyplex treatment. Data are shown as the means±SEM. *$P<0.05$ vs. pre-treatment, one-way ANOVA.

FIG. 8B is a graph depicting ratios of EpiWAT and IngWAT to whole body weight (n=5). FIG. 8D is a graph illustrating changes in dry lean mass compared to the pre-injection state (n=7). Data are shown as the means±SEM. *$P<0.05$ vs. no treatment, #$P<0.05$ vs. pcDNA3, ^$P<0.05$ vs. pcDNA3-IAPP, +$P<0.05$ vs. pcDNA3-LEP, one-way ANOVA.

FIG. 9 includes graphs illustrating the results of the metabolic chamber assay during the initial three days following lPEI-pDNA polyplex treatments. Mean oxygen consumption ($VO_2$) is show in FIG. 9A, heat production is shown in FIG. 9B, and respiratory exchange ratio (RER) is shown in FIG. 9C. All grouped data (n=3) are shown as means±SEM. #$P<0.05$ vs. pcDNA3, +$P<0.05$ vs. pcDNA3-LEP, one-way ANOVA.

DETAILED DESCRIPTION OF THE INVENTION

1. Definitions

Figure 1:
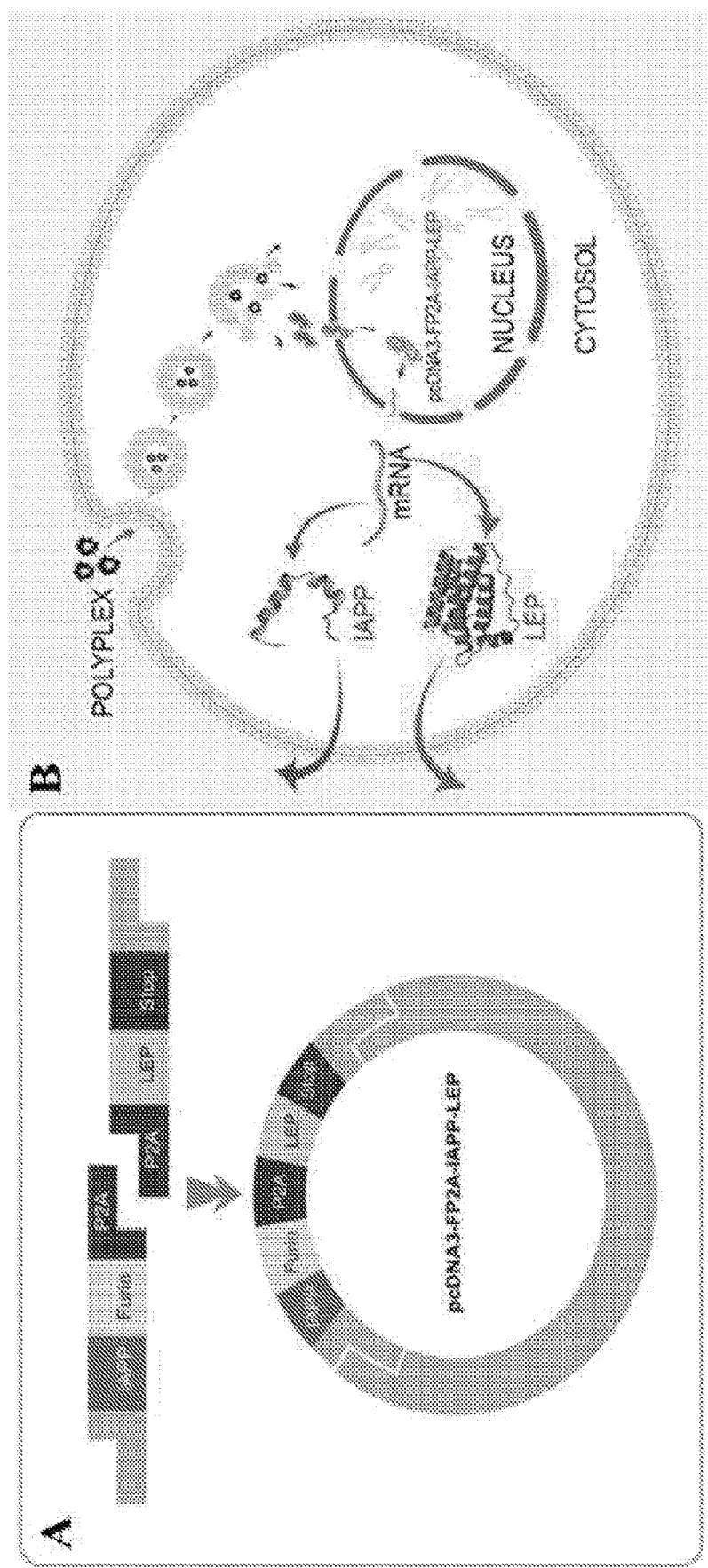
FIG. 1A is a diagram illustrating the construction of the bicistronic plasmid pcDNA3-FP2A-IAPP-LEP. The IAPP and LEP encoding regions are translated individually through furin and P2A.
FIG. 1B is a schematic representation of pcDNA3-FP2A-IAPP-LEP delivery using lPEI (polyplex: lPEI-pcDNA3-FP2A-IAPP-LEP complex).

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting. The terminology used herein is for the purpose of describing particular embodiments only and is not intended to be limiting.

For recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the numbers 6.0, 6.1, 6.2, 6.3, 6.4, 6.5, 6.6, 6.7, 6.8, 6.9, and 7.0 are explicitly contemplated.

As used herein, the term "adipocytes" refers to cells primarily comprised of adipose tissue, specializing in storing energy as fat. There are two types of adipose tissue, white adipose tissue (WAT) (or white fat) and brown adipose tissue (BAT) (also known as "beige adipocytes," "brown in white" (BRITE) cells, and brown fat).

"Complement" or "complementary" as used herein means a nucleic acid can mean Watson-Crick (e.g., A-T/U and C-G) or Hoogsteen base pairing between nucleotides or nucleotide analogs of nucleic acid molecules.

"Identical" or "identity" as used herein in the context of two or more nucleic acids or polypeptide sequences means that the sequences have a specified percentage of residues that are the same over a specified region. The percentage can be calculated by optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. In cases where the two sequences are of different lengths or the alignment produces one or more staggered ends and the specified region of comparison includes only a single sequence, the residues of single sequence are included in the denominator but not the numerator of the calculation. When comparing DNA and RNA, thymine (T) and uracil (U) can be considered equivalent. Identity can be performed manually or by using a computer sequence algorithm such as BLAST or BLAST 2.0.

"Inhibit" as used herein refers to the ability to substantially antagonize, prohibit, prevent, restrain, slow, disrupt, alter, eliminate, stop, or reverse the progression or severity of the activity of a particular agent, disease, or biological process.

"Nucleic acid" or "oligonucleotide" or "polynucleotide" as used herein means at least two nucleotides covalently linked together. The depiction of a single strand also defines the sequence of the complementary strand. Thus, a nucleic acid also encompasses the complementary strand of a depicted single strand. Many variants of a nucleic acid can be used for the same purpose as a given nucleic acid. Thus, a nucleic acid also encompasses substantially identical nucleic acids and complements thereof. A single strand provides a probe that can hybridize to a target sequence under stringent hybridization conditions. Thus, a nucleic acid also encompasses a probe that hybridizes under stringent hybridization conditions.

Nucleic acids can be single stranded or double stranded, or can contain portions of both double stranded and single stranded sequence. The nucleic acid can be DNA, both genomic and cDNA, RNA, or a hybrid, where the nucleic acid can contain combinations of deoxyribo- and ribo-nucleotides, and combinations of bases including uracil, adenine, thymine, cytosine, guanine, inosine, xanthine hypoxanthine, isocytosine and isoguanine. Nucleic acids can be obtained by chemical synthesis methods or by recombinant methods.

"Operably linked" as used herein means that expression of a gene is under the control of a promoter with which it is spatially connected. A promoter can be positioned 5' (upstream) or 3' (downstream) of a gene under its control. The distance between the promoter and a gene can be approximately the same as the distance between that promoter and the gene it controls in the gene from which the promoter is derived. As is known in the art, variation in this distance can be accommodated without loss of promoter function.

A "peptide," "protein," or "polypeptide" as used herein can mean a linked sequence of amino acids and can be natural, synthetic, or a modification or combination of natural and synthetic.

"Stringent hybridization conditions" as used herein means conditions under which a first nucleic acid sequence (e.g., probe) will hybridize to a second nucleic acid sequence (e.g., target), such as in a complex mixture of nucleic acids. Stringent conditions are sequence-dependent and will be different in different circumstances. Stringent conditions can be selected to be about 5 10° C. lower than the thermal melting point (Tm) for the specific sequence at a defined ionic strength pH. The Tm can be the temperature (under defined ionic strength, pH, and nucleic concentration) at which 50% of the probes complementary to the target hybridize to the target sequence at equilibrium (as the target sequences are present in excess, at Tm, 50% of the probes are occupied at equilibrium). Stringent conditions can be those in which the salt concentration is less than about 1.0 M sodium ion, such as about 0.01-1.0 M sodium ion concentration (or other salts) at pH 7.0 to 8.3 and the temperature is at least about 30° C. for short probes (e.g., about 10-50 nucleotides) and at least about 60° C. for long probes (e.g., greater than about 50 nucleotides). Stringent conditions can also be achieved with the addition of destabilizing agents such as formamide. For selective or specific hybridization, a positive signal can be at least 2 to 10 times background hybridization. Exemplary stringent hybridization conditions include the following: 50% formamide, 5×SSC, and 1% SDS, incubating at 42° C., or, 5×SSC, 1% SDS, incubating at 65° C., with wash in 0.2×SSC, and 0.1% SDS at 65° C.

"Subject" as used herein can mean a mammal that wants to or is in need of being immunized with the herein described vaccines. The mammal can be a dog, human, chimpanzee, cat, horse, cow, mouse, or rat.

As used herein, the terms "treatment," "treating," and the like refer to obtaining a desired pharmacologic and/or physiologic effect. Preferably, the effect is therapeutic, i.e., the effect partially or completely cures a disease and/or adverse symptom attributable to the disease. To this end, the inventive method comprises administering a "therapeutically effective amount" of a composition. A "therapeutically effective amount" refers to an amount effective, at dosages and for periods of time necessary, to achieve a desired therapeutic result. The therapeutically effective amount may vary according to factors such as the disease state, age, sex, and weight of the individual, and the ability of the composition to elicit a desired response in the individual. Alternatively, the pharmacologic and/or physiologic effect may be prophylactic, i.e., the effect completely or partially prevents a disease or symptom thereof. In this respect, the inventive method comprises administering a "prophylactically effective amount" of a composition. A "prophylactically effective amount" refers to an amount effective, at dosages and for periods of time necessary, to achieve a desired prophylactic result (e.g., prevention of disease onset).

"Variant" used herein with respect to a nucleic acid means (i) a portion or fragment of a referenced nucleotide sequence; (ii) the complement of a referenced nucleotide sequence or portion thereof; (iii) a nucleic acid that is substantially identical to a referenced nucleic acid or the complement thereof; or (iv) a nucleic acid that hybridizes under stringent conditions to the referenced nucleic acid, complement thereof, or a sequences substantially identical thereto.

"Variant" with respect to a peptide or polypeptide that differs in amino acid sequence by the insertion, deletion, or conservative substitution of amino acids, but retain at least one biological activity. Variant can also mean a protein with an amino acid sequence that is substantially identical to a referenced protein with an amino acid sequence that retains at least one biological activity. A conservative substitution of an amino acid, i.e., replacing an amino acid with a different amino acid of similar properties (e.g., hydrophilicity, degree and distribution of charged regions) is recognized in the art as typically involving a minor change. These minor changes can be identified, in part, by considering the hydropathic index of amino acids, as understood in the art (see, e.g., Kyte et al., *J. Mol. Biol.*, 157: 105-132 (1982)). The hydropathic index of an amino acid is based on a consideration of its hydrophobicity and charge. It is known in the art that amino acids of similar hydropathic indexes can be substituted and still retain protein function. In one aspect, amino acids having hydropathic indexes of ±2 are substituted. The hydrophilicity of amino acids can also be used to reveal substitutions that would result in proteins retaining biological function. A consideration of the hydrophilicity of amino acids in the context of a peptide permits calculation of the greatest local average hydrophilicity of that peptide, a useful measure that has been reported to correlate well with antigenicity and immunogenicity (see, e.g., U.S. Pat. No. 4,554, 101). Substitution of amino acids having similar hydrophilicity values can result in peptides retaining biological activity, for example immunogenicity, as is understood in the art. Substitutions can be performed with amino acids having hydrophilicity values within ±2 of each other. Both the hydrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties.

A variant may be a nucleic acid sequence that is substantially identical over the full length of the full gene sequence or a fragment thereof. The nucleic acid sequence may be 80%, 81%, 82%, 83%, 84%, 85%, 86%, 87%, 88%, 89%, 90%, 91%, 92%, 93%, 94%, 95%, 96%, 97%, 98%, 99%, or 100% identical over the full length of the gene sequence or a fragment thereof. A variant may be an amino acid sequence that is substantially identical over the full length of the amino acid sequence or fragment thereof. The amino acid sequence may be 80%, 81%, 82%, 83%, 84%, 85%, 86%, 87%, 88%, 89%, 90%, 91%, 92%, 93%, 94%, 95%, 96%, 97%, 98%, 99%, or 100% identical over the full length of the amino acid sequence or a fragment thereof.

"Vector" as used herein means a nucleic acid sequence containing an origin of replication. A vector can be a viral vector, bacteriophage, bacterial artificial chromosome (BAC), or yeast artificial chromosome (YAC). A vector can be a DNA or RNA vector. A vector can be a self-replicating extrachromosomal vector, and preferably, is a DNA plasmid. The vector can contain or include one or more heterologous nucleic acid sequences.

The terms "thermogenic program," "thermogenesis," "browning," and "brown fat development," as used herein, refer to the biological conversion of white adipocytes into beige or brown adipocytes in response to various stimuli, such as, exercise and caloric restriction (Mattson, *Ageing Res. Rev.* 9(1): 69 (2010)). The genes PRDM16 (PR domain containing 16), PPARγ (peroxisome proliferator-activated receptor γ), and PGC-1α (peroxisome proliferator-activated receptor γ coactivator 1α) have been shown to be key genes in the regulation of inducible brown fat (Lo et. al., *Biosci Reports,* 33(5): e00065 (2013)).

2. Obesity and Associated Pathways

The World Health Organization (WHO) defines obesity as the accumulation of excessive fat that may be detrimental to an individual's health. Although obesity is preventable, more than 1.9 billion adults aged 18 and over were obese (see *World Health Organization, Fact sheet* 311, January 2015). In general, obesity is caused by consuming a greater number of calories than the number of calories expended, resulting in an energy imbalance. This imbalance is often multifactorial, involving various environmental and genetic factors. There have been a number of genetic pathways associated with obesity, including, for example, glycolysis, thermogenesis, insulin signaling, and leptin signaling. Monogenic and polygenic forms of obesity have been identified. In addition, obesity is known to be caused by environmental factors that interact with genetic predisposition. Examples of obesity-associated genes include SH2B1, KCTD15, MTCH2, NEGR1, LEP, IAPP, and FNDC5 (Choquet et al., *Curr. Genomics,* 12(3):169-179 (2011). The invention described herein provides a plasmid comprising two or more genes (e.g., 2, 3, 4, 5 or more genes) involved in biological pathways associated with obesity.

3. Genes Associated with Obesity a. Islet Amyloid Polypeptide (IAPP)

In one embodiment, the plasmid can comprise a nucleic acid sequence encoding islet amyloid polypeptide (IAPP). IAPP, also referred to in the art as amylin, pramlintide, diabetes-associated peptide, and insulinoma amyloid peptide, is a peptide hormone that is synthesized in the brain and pancreas (See Mietlicki-Baase, *Physiol. Behav.*, Epub ahead of print (2016)). IAPP is known to play a role in energy balance and glycemic regulation, and has been shown to act as a satiation signal. In particular, IAPP has been shown to elicit a thermogenic program and increase energy expenditure in animal models (see, e.g., Wielinga et al., *Physiol. Behav.,* 101(1): 45-52 (2010) and Contreras et al., *Ann. Med.,* 47: 150-168 (2015)). The U.S. Food and Drug Administration (FDA) has approved use of an IAPP analog for the treatment of diabetes mellitus, due to the role of IAPP in improving glucose levels by suppressing gastric emptying and glucagon secretion in animal models and humans (see, e.g., Thompson et al., *Diabetes,* 46: 632-36 (1997), Young et al., *Nutrition,* 14: 524-27 (1998), and Mietlicki-Baase, *Physiol. Behav.*, Epub ahead of print (2016)). In addition, IAPP inhibits food intake, which contributes to weight loss (see Rushing et al., *Endocrinology*, 141: 850-53 (2000) and Kong et al., *Diabetologia*, 40: 82-88 (1997)).

The IAPP polypeptide contains 37 amino acid residues, and is derived from the proteolytic processing of an 89 amino acid precursor. Genes encoding IAPP are found in a variety of mammalian species, such as humans, felines, and rodents, and several IAPP amino acid sequences have been deposited in the GenBank database (see, e.g. GenBank Accession NOs: X56030.1, X13859.1, 557804.1, 557802.1, NM_012586.2, NM_000415.2, NM_001003233.2, and NM_010491.2). The nucleic acid sequence encoding IAPP can comprise any IAPP-encoding nucleic acid sequence known in the art, such as those described above. In one embodiment, the nucleic acid sequence encoding IAPP comprises SEQ ID NO: 1, which encodes the amino acid sequence of SEQ ID NO: 2. In another embodiment, the nucleic acid sequence encodes an IAPP protein comprising the amino acid sequence of SEQ ID NO: 3.

Alternatively, the nucleic acid sequence encoding IAPP comprises a nucleic acid sequence that is desirably at least about 70% identical (e.g., at least 71%, at least 72%, at least 73%, at least 74%, at least 75%, at least 76%, at least 77%, at least 78%, or at least 79% identical) to SEQ ID NO: 1, preferably at least about 80% identical (e.g., at least 81%, at least 82%, at least 83%, at least 84%, at least 85%, at least 86%, at least 87%, at least 88%, or at least 89% identical) to SEQ ID NO: 1, and more preferably at least about 90% identical (e.g., at least 91%, at least 92%, at least 93%, at least 94%, at least 95%, at least 96%, at least 97%, at least 98%, at least 99%, or 100% identical) to SEQ ID NO: 1.

Nucleic acid or amino acid sequence "identity," as described herein, can be determined by comparing a nucleic acid or amino acid sequence of interest to a reference nucleic acid or amino acid sequence. The percent identity is the number of nucleotides or amino acid residues that are the same (i.e., that are identical) as between the sequence of interest and the reference sequence divided by the length of the longest sequence (i.e., the length of either the sequence of interest or the reference sequence, whichever is longer). A number of mathematical algorithms for obtaining the optimal alignment and calculating identity between two or more sequences are known and incorporated into a number of available software programs. Examples of such programs include CLUSTAL-W, T-Coffee, and ALIGN (for alignment of nucleic acid and amino acid sequences), BLAST programs (e.g., BLAST 2.1, BL2SEQ, and later versions thereof) and FASTA programs (e.g., FASTA3x, FAS™, and SSEARCH) (for sequence alignment and sequence similarity searches). Sequence alignment algorithms also are disclosed in, for example, Altschul et al., *J. Molecular Biol.*, 215(3): 403-410 (1990), Beigert et al., *Proc. Natl. Acad. Sci. USA*, 106(10): 3770-3775 (2009), Durbin et al., eds., *Biological Sequence Analysis: Probalistic Models of Proteins and Nucleic Acids*, Cambridge University Press, Cambridge, UK (2009), Soding, *Bioinformatics*, 21(7): 951-960 (2005), Altschul et al., *Nucleic Acids Res.*, 25(17): 3389-3402 (1997), and Gusfield, *Algorithms on Strings, Trees and Sequences*, Cambridge University Press, Cambridge UK (1997)).

In another embodiment, the nucleic acid sequence can encode a fragment of IAPP. The nucleic acid sequence can encode an IAPP fragment of any suitable size, so long as the IAPP fragment retains the biological activity of the full-length IAPP polypeptide (e.g., inducing a thermogenic response, increasing energy expenditure, improving glycemic control, reducing food intake, and slowing of gastric emptying in a mammal). For example the nucleic acid sequence can be at least 10%, at least 15%, at least 20%, at least 25%, at least 30%, at least 35%, at least 40%, at least 45%, at least 50%, at least 55% at least 60%, at least 65%, at least 70%, at least 75%, at least 80%, at least 85%, at least 90%, at least 95%, at least 96%, at least 97%, at least 98% or at least 99% of SEQ ID NO: 1. In another embodiment, the nucleic acid sequence can encode a variant (as defined above) of the IAPP gene.

b. Leptin (LEP)

In another embodiment, the plasmid can comprise a nucleic acid sequence encoding leptin (LEP). LEP, also referred to in the art as obesity factor, metreleptin, and obese protein, is a hormone produced by white adipocytes (see Trayhurn et al., *Proc. Nutr. Soc.* 60(3): 329-39 (2001)). LEP is known to play a role in regulation of body weight, regulation of immune and inflammatory responses, hematopoiesis, angiogenesis, wound healing, and the development of diabetes mellitus II. In particular, LEP functions as part of a signaling pathway that can inhibit food intake and regulate energy expenditure to maintain constancy of the adipose mass (see GeneCards® Human Gene Database, Weizmann Institute of Science, ID NO: GC07P128241).

The LEP peptide consists of 167 amino acid residues. Genes encoding LEP are found in a variety of mammalian species, such as humans, felines, and rodents, and several LEP amino acid sequences have been deposited in the GenBank database (see, e.g., GenBank Accession NOs: NM_000230.2, NM_001003070.1, NM_173928.2, NM_013076.3, AB041360.1, NM_008493.3, NM_213840.1, and NM_001290901.1). The nucleic acid sequence encoding LEP can comprise any LEP-encoding nucleic acid sequence known in the art, such as those described above. In one embodiment, the nucleic acid sequence encoding LEP comprises SEQ ID NO: 4, which encodes the amino acid sequence of SEQ ID NO: 5. In another embodiment, the nucleic acid sequence encodes a LEP protein comprising the amino acid sequence of SEQ ID NO: 6.

Alternatively, the nucleic acid sequence encoding LEP comprises a nucleic acid sequence that is desirably at least about 70% identical (e.g., at least 71%, at least 72%, at least 73%, at least 74%, at least 75%, at least 76%, at least 77%, at least 78%, or at least 79% identical) to SEQ ID NO: 4, preferably at least about 80% identical (e.g., at least 81%, at least 82%, at least 83%, at least 84%, at least 85%, at least 86%, at least 87%, at least 88%, or at least 89% identical) to SEQ ID NO: 4, and more preferably at least about 90% identical (e.g., at least 91%, at least 92%, at least 93%, at least 94%, at least 95%, at least 96%, at least 97%, at least 98%, at least 99%, or 100% identical) to SEQ ID NO: 4, as determined using any suitable method described herein or known in the art.

In another embodiment, the nucleic acid sequence can encode a fragment of LEP. The nucleic acid sequence can encode an LEP fragment of any suitable size, so long as the LEP fragment retains the biological activity of the full-length LEP polypeptide (e.g., regulation of body weight, regulation of immune and inflammatory responses, hematopoiesis, angiogenesis, and wound healing. For example the nucleic acid sequence can be at least 10%, at least 15%, at least 20%, at least 25%, at least 30%, at least 35%, at least 40%, at least 45%, at least 50%, at least 55% at least 60%, at least 65%, at least 70%, at least 75%, at least 80%, at least 85%, at least 90%, at least 95%, at least 96%, at least 97%, at least 98% or at least 99% of SEQ ID NO: 4. In another embodiment, the nucleic acid sequence can encode a variant (as defined above) of the leptin gene.

c. FNDC5

In another embodiment, the plasmid can comprise a nucleic acid sequence encoding fibronectin type III containing 5 (FNDC5). FNDC5, also referred to in the art as irisin, fibronectin type III repeat-containing domain, and FRCP2, is produced by muscle cells during and after exercise in humans and animal models. FNDC5 is subsequently cleaved, generating the peptide hormone irisin (see, e.g., Bostrom et al., *Nature,* 481(7382): 463-468 (2012) and GeneCards® ID NO: GC01M032830). It is thought that FNDC5 plays a role in the browning of white adipocytes in animal models and humans, a process which contributes to weight loss (see, e.g., Pyrzak et al., *Adv. Exp. Med. Biol.,* 866: 25-34 (2015), Wu et al., *J. Biol. Chem.* 5, 289(49): 34129-40 (2014), and Daskalopoulou et al., *Eur. J. Endocrinol.* 171(3): 343-52 (2014).

The FNDC5 peptide contains of 212 amino acid residues. Genes encoding FNDC5 are found in a variety of mammalian species, such as humans, felines, and rodents, and several FNDC amino acid sequences have been deposited in the GenBank database (see, e.g. GenBank Accession NOs: NM_001270981.1, NM_027402.3, NM_153756.2, NM_001171940.1, NM_001171941.2, and NM_001105421.1). The nucleic acid sequence encoding FNDC5 can comprise any FNDC5-encoding nucleic acid sequence known in the art, such as those described above. In one embodiment, the nucleic acid sequence encoding FNDC5 comprises SEQ ID NO: 7, which encodes the amino acid sequence of SEQ ID NO: 8. In another embodiment, the nucleic acid sequence encodes an FNDC5 protein comprising the amino acid sequence of SEQ ID NO: 9.

Alternatively, the nucleic acid sequence encoding FNDC5 comprises a nucleic acid sequence that is desirably at least about 70% identical (e.g., at least 71%, at least 72%, at least 73%, at least 74%, at least 75%, at least 76%, at least 77%, at least 78%, or at least 79% identical) to SEQ ID NO: 7, preferably at least about 80% identical (e.g., at least 81%, at least 82%, at least 83%, at least 84%, at least 85%, at least 86%, at least 87%, at least 88%, or at least 89% identical) to SEQ ID NO: 7, and more preferably at least about 90% identical (e.g., at least 91%, at least 92%, at least 93%, at least 94%, at least 95%, at least 96%, at least 97%, at least 98%, at least 99%, or 100% identical) to SEQ ID NO: 7, as determined using any suitable method described herein or known in the art.

In another embodiment, the nucleic acid sequence can encode a fragment of FNDC5. The nucleic acid sequence can encode an FNDC5 fragment of any suitable size, so long as the FNDC5 fragment retains the biological activity of the full-length FNDC5 polypeptide (e.g., browning of white adipocytes). For example the nucleic acid sequence can be at least 10%, at least 15%, at least 20%, at least 25%, at least 30%, at least 35%, at least 40%, at least 45%, at least 50%, at least 55% at least 60%, at least 65%, at least 70%, at least 75%, at least 80%, at least 85%, at least 90%, at least 95%, at least 96%, at least 97%, at least 98% or at least 99% of SEQ ID NO: 7. In another embodiment, the nucleic acid sequence can encode a variant (as defined above) of the FNDC5 gene.

4. Plasmid

The two or more nucleic acid sequences encoding IAPP, LEP, and/or FNDC5 desirably are incorporated into a vector. In one embodiment, the invention provides a plasmid comprising two or more nucleic acid sequences encoding IAPP, LEP, and/or FNDC5. The plasmid described herein can be, or be based on, any suitable plasmid known in the art, a variety of which are available from commercial sources. Examples of suitable plasmids include, but are not limited to pcDNA3 (INVITROGEN™), pcDNA 3.1(+) (INVITROGEN™), pcDNA3.1(−) (INVITROGEN™), psPAX2, pMD2.G, pX330, pX458, PX459, and PX335.

The plasmid can comprise two or more of the above-described nucleic acid sequences in any combination. For example, the plasmid can comprise (1) a nucleic acid sequence encoding IAPP and a nucleic acid sequence encoding LEP, (2) a nucleic acid sequence encoding IAPP and a nucleic acid sequence encoding FNDC5, or (3) a nucleic acid sequence encoding LEP and a nucleic acid sequence encoding FNDC5. In another embodiment, the plasmid can comprise three nucleic acid sequences, i.e., a nucleic acid sequence encoding IAPP, a nucleic acid sequence encoding LEP, and a nucleic acid sequence encoding FNDC5. An exemplary plasmid encoding IAPP and LEP comprises the nucleic acid sequence of SEQ ID NO: 10). An exemplary plasmid encoding IAPP and FNDC5 comprises the nucleic acid sequence of SEQ ID NO: 11.

In addition to the two or more nucleic acid sequences encoding IAPP, LEP, and/or FNDC5, the plasmid preferably comprises expression control sequences, such as promoters, enhancers, polyadenylation signals, transcription terminators, internal ribosome entry sites (IRES), and the like, that provide for the expression of the coding sequences in a host cell. Exemplary expression control sequences are known in the art and described in, for example, Goeddel, *Gene Expression Technology: Methods in Enzymology,* Vol. 185, Academic Press, San Diego, Calif. (1990).

A large number of promoters, including constitutive, inducible, and repressible promoters, from a variety of different sources are well known in the art. Representative sources of promoters include for example, virus, mammal, insect, plant, yeast, and bacteria, and suitable promoters from these sources are readily available, or can be made synthetically, based on sequences publicly available, for example, from depositories such as the ATCC as well as other commercial or individual sources. Non-limiting examples of promoters include a promoter from simian virus 40 (SV40), a mouse mammary tumor virus (MMTV) promoter, a human immunodeficiency virus (HIV) promoter such as the bovine immunodeficiency virus (BIV) long terminal repeat (LTR) promoter, a Moloney virus promoter, an avian leukosis virus (ALV) promoter, a cytomegalovirus (CMV) promoter such as the CMV immediate early promoter, an Epstein Barr virus (EBV) promoter, or a Rous sarcoma virus (RSV) promoter. The promoter also can be a mammalian promoter, such as, for example, an actin promoter, a myosin promoter, a hemoglobin promoter, a muscle creatine promoter, or a metallothionein promoter.

Multiple nucleic acid sequences can be operably linked to the same or different promoters. In one embodiment of the invention, each of the two or more nucleic acid sequences is operably linked to a separate promoter. While it is preferred that each promoter is different, one or ordinary skill in the art will appreciate the advantages of using one particularly efficient promoter to control expression of all of the two or more nucleic acid sequences present in the plasmid. Thus, each of the two or more nucleic acid sequences can be operably linked to the same promoter. In another embodiment, each of the two or more nucleic acid sequences are operably linked to a different promoter. The selection of an appropriate promoter for a given nucleic acid sequence will depend upon a number of factors, including promoter strength, and can be performed using routine methods known in the art.

The plasmid also can comprise a polyadenylation signal, which can be located downstream of the two more nucleic acid sequences. The polyadenylation signal can be any suitable polyadenylation signal, including, for example, a SV40 polyadenylation signal, LTR polyadenylation signal, bovine growth hormone (bGH) polyadenylation signal, human growth hormone (hGH) polyadenylation signal, or human β-globin polyadenylation signal. The SV40 polyadenylation signal can be a polyadenylation signal from a pCEP4 vector (Invitrogen, San Diego, Calif.).

The plasmid also can comprise an enhancer. The term "enhancer" as used herein, refers to a DNA sequence that increases transcription of, for example, a nucleic acid sequence to which it is operably linked. Enhancers can be located many kilobases away from the coding region of the nucleic acid sequence and can mediate the binding of regulatory factors, patterns of DNA methylation, or changes in DNA structure. The enhancer can be isolated or derived from any suitable mammalian gene, such as, for example actin, myosin, hemoglobin, muscle creatine, or virus, such as, for example, CMV, HA, RSV or EBV. Enhancers are further described in, for example, U.S. Pat. Nos. 5,593,972 and 5,962,428, and International Patent Application Publication WO 94/016737.

The plasmid can comprise additional elements to optimize expression and production of multiple proteins from a single vector. In one embodiment, the plasmid can comprise a nucleic acid sequence encoding a self-processing peptide, also referred to as a "self-cleaving" peptide, which allows multiple proteins to be encoded as a polyprotein, which dissociates into component proteins upon translation (see, e.g., Radcliffe et al., *Gene Therapy*, 11: 1673-1674 (2004)). In one embodiment, the plasmid comprises a nucleic acid sequence encoding a 2A peptide. 2A peptides, first discovered in picornaviruses, are short (about 20 amino acids) and enable a single transcript mRNA encoding multiple genes to express their corresponding peptides simultaneously in similar molar concentrations. Cleavage occurs between the glycine and proline residues found on the C-terminus of the peptide, which typically results in the upstream cistron having a few additional residues added to the end and the downstream cistron beginning with a proline (Kim et al., *PLoS One*, 6(4): e18556.doi: 10.1371/journal.pone. 0018556 (2011)). Several 2A peptides are known in the art, any of which can be used in the plasmid described herein. In one embodiment, the plasmid comprises a nucleic acid sequence encoding a porcine teschovirus-1 2A (P2A), which has been shown to exhibit the highest cleavage efficiency in mammalian cells among the 2A family.

In another embodiment, the plasmid comprises a nucleic acid sequence encoding a furin peptide linker gene. The furin peptide is used in the art as a linker to prevent possible adverse effects derived from the residual 2A peptide in 2A-based-gene constructs (18 from the provisional). Furin is an enzyme which belongs to the subtilisin-like proprotein convertase family, which includes proprotein convertases that process latent precursor proteins into their biologically active products. Furin is a calcium-dependent serine endoprotease highly expressed in the Golgi apparatus, where it functions to cleave other proteins into their mature/active forms. Furin cleaves proteins just downstream of a basic amino acid target sequence (canonically, Arg-X-(Arg/Lys)-Arg') (see, e.g., Lin et al., *Blood Cells*, 40(1):122-31 (2008), Kuninger, *BMC Biochemistry*, 9: 9 (2008), Thomas, *Nature Reviews Molecular Cell Biology*, 3(10): 753-66 (2002), and Shiryaev et al., *The Journal of Biological Chemistry*, 282 (29): 20847-53 (2007)).

6. Non-Viral Carriers

It will be appreciated that DNA vectors, such as plasmids, are often immunogenic in vivo, and can be degraded by nucleases in serum, limiting their use as effective gene delivery systems in vivo. Accordingly, the plasmid described herein can be conjugated to a carrier to reduce potential toxicity and immunogenicity in vivo. Ideally, the carrier is a non-viral carrier, as several limitations have been associated with viral vector delivery of plasmids, including immunogenicity, broad tropism, difficulty of vector production, limited DNA packaging capacity, and carcinogenesis (Yin et al., *Nature Reviews Genetics*, 15: 541-555 (2014)).

The plasmid can be conjugated to any suitable non-viral carrier that can efficiently deliver plasmids to cells in vitro and/or in vivo, several of which are known in the art. In one embodiment, the non-viral carrier can be a polymeric cation. Examples of suitable polymeric cations include, but are not limited to, branched polyethylenimine (PEI), linear polyethylenimine (lPEI), reducible polyethyleneimine, poly(l lysine), poly[(2 dimethylamino)ethyl methacrylate], poly(β amino ester)s, chitosan, polyamidoamine dendrimer, poly[a-(4-aminobutyl)-L-glycolic acid], and PEG grafted polycations such as PEI-g-PEG. In another embodiment, the non-viral carrier can be a small molecule cation. Examples of suitable small molecule cations include, but are not limited to, DOTMA: N[1-(2,3-dioleyloxy) propyl]-N,N,N-trimethylammonium chloride, DOTAP: 1,2-dioleyl-3-trimethylamonium-propane, DMRIE: N-(2-hydroxyethyl)-N,N-dimethyl-2,3-bis(tetradecyloxy-1-propananium bromide), DOTIM: 1-[2-(oleoyloxy)ethyl]-2-oleyl-3-(2-hydroxyethyl) imidazolinium chloride, DOGS: dioctadecylamidoglycylspermine, DC-Chol: [N—(N',N'-dimethylaminoethane)-carbamoyl]cholesterol, BGTC: bis-guanidium-tren-cholesterol, DOPE: 1,2-dioleyl-sn-glycerol-3-phosphoethanolamine, and calcium phosphate.

The plasmid can be conjugated to the non-viral carrier using any suitable method known in the art, such as those described in, e.g., Luten et al., *J. Controlled Release*, 126(2): 97-110 (2008); Kawakami et al., *J. Pharm. Sci.*, 97(2): 726-745 (2008); Katsuri et al., *Biomaterials*, 26(32): 6375-6385 (2005).

7. Compositions

The invention provides a composition comprising the above-described plasmid and a pharmaceutically acceptable carrier. The composition desirably is a physiologically acceptable (e.g., pharmaceutically acceptable) composition, which comprises a carrier, preferably a physiologically (e.g., pharmaceutically) acceptable carrier. Any suitable carrier can be used within the context of the invention, and such carriers are well known in the art. The choice of carrier will be determined, in part, by the particular use of the composition (e.g., administration to an animal) and the particular method used to administer the composition. Accordingly, there is a wide variety of suitable formulations of the composition of the present invention. The previously described formulations and methods are merely exemplary and are in no way limiting. However, oral and injectable formulations are preferred. The pharmaceutical composition optionally can be sterile.

Formulations suitable for oral administration can comprise (a) liquid solutions, such as an effective amount of the active ingredient (i.e., a plasmid encoding IAPP, LEP, and/or FNDC5) dissolved in diluents, such as water, saline, or orange juice; (b) capsules, sachets or tablets, each containing a predetermined amount of the active ingredient, as solids or granules; (c) suspensions in an appropriate liquid; and (d) suitable emulsions. Tablet forms can include one or more of lactose, mannitol, corn starch, potato starch, microcrystalline cellulose, acacia, gelatin, colloidal silicon dioxide, croscarmellose sodium, talc, magnesium stearate, stearic acid, and other excipients, colorants, diluents, buffering agents, moistening agents, preservatives, flavoring agents, and pharmacologically compatible excipients. Lozenge forms can comprise the active ingredient in a flavor, usually sucrose and acacia or tragacanth, as well as pastilles comprising the active ingredient in an inert base, such as gelatin and glycerin, or sucrose and acacia, emulsions, gels, and the like containing, in addition to the active ingredient, such excipients as are known in the art.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations can be presented in unit-dose or multi-dose sealed containers, such as ampules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described.

8. Cells

The invention also provides a host cell comprising the above-described composition. The cell may be in vitro or in vivo, depending on the application. Preferred in vitro cells are those that can be easily and reliably grown, have reasonably fast growth rates, have well characterized expression systems, and can be transformed or transfected easily. The host cell can be a prokaryotic cell or a eukaryotic cell. Examples of suitable prokaryotic cells include, but are not limited to, cells from the genera *Bacillus* (such as *Bacillus subtilis* and *Bacillus brevis*), *Escherichia* (such as *E. coli*), *Pseudomonas, Streptomyces, Salmonella*, and *Erwinia*. Preferably, the plasmid is introduced into a eukaryotic cell. Suitable eukaryotic cells are known in the art and include, for example, yeast cells, insect cells, and mammalian cells. In one embodiment, the host cell is a mammalian cell. A number of suitable mammalian host cells are known in the art and many are available from the American Type Tissue Collection (ATCC, Manassas, Va.). Examples of suitable mammalian cells include, but are not limited to Chinese hamster ovary cells (CHO) (ATCC No. CCL61), human embryonic kidney 293 cells (HEK-293) (ATCC No. CRL1573), 3T3 cells (ATCC No. CRL92), and COS-1 cells (ATCC No. CRL1650), and COS-7 cells (ATCC No. CRL1651). Further exemplary mammalian host cells include primate cell lines, rodent cell lines, and human cell lines, including transformed cell lines. Normal diploid cells, cells derived from in vitro culture of primary tissue, as well as primary explants are also suitable. Other suitable mammalian cell lines are known in the art and are readily available from depositories such as the ATCC as well as other commercial or individual sources.

Most preferably, the mammalian cell is a human cell. Examples of suitable human cells include, but are not limited to, human embryonic kidney 293 cells (HEK-293) (ATCC® CRL-1573™), HeLa cells (ATCC® CCL-2™), Jurkat cells (ATCC® TIB-152™), MCF-7 cells (ATCC® HTB-22™), NIH-3T3 cells (ATCC® CRL-1658™), and HT-29 cells (SIGMA ALDRICH® 91072201).

Other suitable human cell lines are known in the art and are readily available from depositories such as the ATCC as well as other commercial or individual sources. Methods for selecting suitable mammalian host cells and methods for transformation, culture amplification, screening, and purification of cells are known in the art.

9. Method for Increasing Metabolic Activity

The invention further provides a method for increasing metabolic activity in an animal. The method comprises administering to an animal in need thereof the above-described composition, whereby the two or more nucleic acids sequences are expressed in the animal and metabolic activity is increased.

The terms "metabolic activity" and "metabolism," as used herein, refer to a set of chemical transformations that are necessary for maintaining life in any organism. Metabolic activity involves the transformation of energy and matter in the body. Examples of factors affected by metabolic activity include, but are not limited to blood glucose levels, blood insulin levels, blood lipid concentrations, whole body adiposity, fat metabolism, energy metabolism, body weight, satiety, food intake, and browning of white adipocytes.

The terms "increase," "enhance," or "improve," as used herein with respect to metabolic activity, refer to the ability to substantially induce, augment, raise, promote, stimulate, speed up, allow, or encourage metabolic activity in an animal. The plasmid of the invention, and the composition comprising same, preferably increases metabolic activity in an animal by at least about 20%, about 30%, about 40%, about 50%, about 60%, about 70%, about 80%, about 90%, about 95%, about 100% (or a range defined by any two of the foregoing values), as compared to an animal that has not received the composition.

Metabolic activity can be measured by assessing a variety of parameters, including, for example, blood glucose levels, blood insulin levels, blood lipid concentrations, whole body adiposity, fat metabolism, energy metabolism, body weight, satiety, food intake, and browning of white adipocytes. Thus, in some embodiments, increasing the metabolic activity in the mammal can comprise one or any combination of the following: (a) reducing blood glucose levels in the mammal, (b) reducing blood insulin levels in the mammal, (c) reducing blood lipid concentrations in the mammal, (d) reducing whole body adiposity in the mammal, (d) increasing fat metabolism in the mammal, (e) increasing energy metabolism in the mammal, (f) reducing body weight in the mammal, (g) increasing satiety in the mammal, (h) reducing food intake in the mammal, and/or (i) increasing browning of white adipocytes. It will be appreciated, however, that any aspect of metabolic activity can be increased as a result of the inventive method. Specific methodology for measuring changes in metabolic activity include, but are not limited to (a) measuring calculating body composition via nuclear magnetic resonance, (b) blood chemistry analysis via insulin ELISA kits, free fatty acid test kits, and triglyceride assay kits, (c) measuring glucose levels in blood via glucose test strips, (d) metabolic chamber assays comparing the weight of adipose tissue, (e) tracking food consumption, (f) measuring weight by scale, (g) measuring body fat with a caliper, (h) bioelectric impedance analysis, (i) measuring body circumference, and (j) hydrostatic weighing.

As used herein, the term "blood glucose levels" refers to the level of glucose in the bloodstream of a subject. Normal human blood glucose levels range between about 70 to 115 mg/dL after fasting overnight. The term "blood insulin levels" refers the level of insulin in the blood. Normal human insulin levels typically are less than 17 mcU/mL. The term "blood lipid concentrations" refers to the level of lipids in the blood, including but not limited to high density lipoprotein (HDL), low density lipoprotein (LDL), and triglycerides. Normal human levels of HDL are typically less than 130 mg/dL. Normal human levels of LDL are typically greater than 35 mg/dL. Normal human levels of triglycerides are typically less than 150 mg/dL. As used herein, the term "reducing whole body adiposity" means lowering the level of accumulation of lipids in the body. The term "increasing fat metabolism" means raising the level of oxidation, decomposition, and/or synthesis of fats in tissues. The term "increasing energy metabolism" means increasing the rate or efficiency of the process of generating energy (ATP) from nutrients. The term "reducing body weight" means lowering the total weight of an animal as measured in ounces, pounds, grams, or kilograms. The term "increasing satiety" means raising the feeling or condition of being full. The term "reducing food intake" refers to lowering the amount of food an animal consumes. As used herein, the term "increasing browning of white adipocytes" means raising the level of a process where white adipocytes takes on characteristics of brown adipocytes, notably taking on a brown-fat-like gene expression program (e.g., expression of UCP1, Cidea (cell death-inducing DFFA-like effector a) and Dio2 (diodinase 2)), and the presence of multilocular lipid droplets and multiple mitochondria.

Any route of administration can be used to deliver the composition to the mammal. Indeed, although more than one route can be used to administer the composition, a particular route can provide a more immediate and more effective reaction than another route. Preferably, the composition is administered orally or via intraperitoneal injection. The composition also can be applied or instilled into body cavities, absorbed through the skin (e.g., via a transdermal patch), inhaled, ingested, topically applied to tissue, or administered parenterally via, for instance, intravenous, peritoneal, or intraarterial administration.

The composition can be administered in or on a device that allows controlled or sustained release, such as a sponge, biocompatible meshwork, mechanical reservoir, or mechanical implant. Implants (see, e.g., U.S. Pat. No. 5,443,505) and devices (see, e.g., U.S. Pat. No. 4,863,457), such as an implantable device, e.g., a mechanical reservoir or an implant or a device comprised of a polymeric composition, are particularly useful for administration of the composition. The composition can be administered in the form of sustained-release formulations (see, e.g., U.S. Pat. No. 5,378,475) comprising, for example, gel foam, hyaluronic acid, gelatin, chondroitin sulfate, a polyphosphoester, such as bis-2-hydroxyethyl-terephthalate BHET), and/or a polylactic-glycolic acid.

The composition can be administered to any suitable mammal in need thereof. Examples of suitable mammals include, but are not limited to humans, non-human primates, and rodents (e.g. mice or rats). In a preferred embodiment, the composition is administered to an obese mammal. In general, "obesity" is characterized as an excess of adipose tissue. A mammal, particularly a human, is considered obese or overweight when the mammal's weight is greater than what is considered healthy for a given height. In humans, obesity typically is determined by measuring body mass index (BMI). BMI is calculated as the weight in kilograms of an individual divided by the square of the individual's height in meters. According to the U.S. Centers for Disease Control and Prevention (CDC), a BMI between 25.0 and 29.9 falls within the "overweight" range, and a BMI higher than 30.0 falls within the "obese" range. Obesity often gives rise to obesity-related conditions including, but not limited to, non-alcoholic fatty liver disease, type II diabetes, sleep apnea, high blood pressure, heart disease, stroke, cancer, gallbladder disease infertility, irregular periods, erectile dysfunction, and osteoarthritis.

The method described herein can be used to increase the metabolic activity of any suitable mammal in need thereof. Preferably, the mammal is a human. Obesity in humans can be measured using routine method known in the art, such as, for example, measuring BMI, measuring waist circumference, skinfold thickness measurements, bioelectrical impedance, densitometry (underwater weighing), air-displacement plethysmography, dual energy x-ray absorptiometry (DXA), densitometry, hydrometry, computerized tomography, magnetic resonance imaging, and the like. In some embodiments, the mammal is a human having a BMI between 25.0 and 29.9 (i.e., overweight according to the aforementioned CDC guidelines). In some embodiments, the mammal is a human having a BMI of 30.0 or higher (i.e., obese according to the aforementioned CDC guidelines). In other embodiments, the mammal is a human male having a waist circumference greater than 40 inches or a human female having a waist circumference greater than 35 inches.

In another embodiment, the mammal can be non-human animal model of obesity. Examples of animal models of obesity include, but are not limited to, diet induced obesity (DIO), in which the animal is fed a diet of approximately 60% fat (kcal), lethal yellow mutant mouse, ob/ob mouse, db/db mouse, New Zealand obese mouse, Tsumara Suzuki Obese Diabetes mouse, M16 mouse, kuo kondo mouse, Zucker fatty rat, Wistar fatty rat, and Otsuka long evans tokushima fatty (Kanasaki et al., *Journal of Biomedicine and Biotechnology*, 2011: 197636 (2011)). In some embodiments, the animal is fed a high fat diet.

In one embodiment, the effect induced by expression of the two or more genes is synergistic as compared to the effect of expression of each gene alone. As used herein, the term "synergistic" means that the effect achieved with the plasmid comprising two or more nucleic acid sequences described herein is greater than the sum of the effects that result from a plasmid comprising each of the two or more nucleic acid sequences individually. Advantageously, such synergy between the two or more nucleic acid sequences allows for the use of smaller doses of the plasmid. In some embodiments, the combination of IAPP and LEP has a synergistic effect. In some embodiments, the combination of IAPP and FNDC5 has a synergistic effect. In some embodiments, the combination of IAPP, FNDC5, and LEP has a synergistic effect.

The composition described herein may be administered alone or in combination with other conventional anti-obesity therapies. Other anti-obesity therapies include, but are not limited to, exercise programs, lowering caloric intake, behavioral modification, weight-loss surgery, prescription weight-loss medications, prescription behavioral modification medications, and commercially-available weight loss programs.

The following examples further illustrate the invention but, of course, should not be construed as in any way limiting its scope.

Example 1

This example describes the construction of a plasmid comprising a nucleic acid sequence encoding islet amyloid polypeptide (IAPP) and either a nucleic acid sequence encoding leptin (LEP) or a nucleic acid sequence encoding fibronectin type III domain containing 5 (FNDC5).

Three plasmids referred to as pcDNA3-IAPP, pcDNA3-LEP, and pcDNA3-FP2A-IAPP-LEP were constructed with mouse-originated IAPP and LEP genes. For the bicistronic plasmid pcDNA3-FP2A-IAPP-LEP, the IAPP and LEP genes and nucleic acid sequences encoding furin and P2A (FP2A) were assembled by IN-FUSION™ reaction (Huh, h. et al., Biologicals, 35: 165-171). A schematic of the bicistronic pcDNA3-FP2A-IAPP-LEP plasmid is depicted in FIG. 1. Forward and reverse PCR primers were designed which included a more than 15 base pair overlap with the neighboring segment of pcDNA3 plasmid (Invitrogen, Carlsbad, Calif., USA) and more than 20 base pairs of target gene-specific sequence. The primer sequences for pcDNA3-FP2A-IAPP-LEP and pcDNA3-LEP plasmids are provided in Table 1.

TABLE 1

| Target ORF (Final plasmid) | Forward primer | Reverse primer |
| --- | --- | --- |
| IAPP (pcDNA3-FP2A-IAPP-LEP) | GTACCGAGCTCGGAT CCAGACATGATGTGC ATCTCCAAACTGCCA G (SEQ ID NO: 12) | AGGCCCGGGGTTTTCTTCAA CATCTCCTGCTTGCTTTAACA GAGAGAAGTTCGTGGCTCCG GATCCCCTTTTTGCGCGAAC GAGTAAGAAATCCAAGGATT CCCT (SEQ ID NO: 13) |
| LEP (pcDNA3-FP2A-IAPP-LEP) | GAAGAAAACCCCGGG CCTATGTGCTGGAGA CCCCTGTGTC (SEQ ID NO: 14) | GGATATCTGCAGAATTCTTA GCATTCAGGGCTAACATCCA ACTGT (SEQ ID NO: 15) |
| LEP (pcDNA3-LEP) | GTACCGAGCTCGGAT CCAGAAATGTGCTGG AGACCCCTGTGTC (SEQ ID NO: 16) | CATGCTCGAGCGGCCGCTTA GCATTCAGGGCTAACATCCA ACTGT (SEQ ID NO: 17) |

Additionally, short pieces of P2A, furin, restriction enzyme sites, and a translation initiation site (Kozak sequence) were added to the primer sequences. PCR amplification was performed with the primers and mouse-originated IAPP and LEP cDNA using CLONEAMP™ HiFi Premix (Clontech, Mountain View, Calif.). After pcDNA3 was digested by BamHI and EcoRI, the PCR amplicons were ligated into the linearized pcDNA3 by IN-FUSION™ HD Enzyme Premix (Clontech Mountain View, Calif.). The reaction mixture was then transformed into STELLAR™ Competent Cells (Clontech, Mountain View, Calif.), followed by ampicillin-containing LB agar plate colony identification. For pcDNA3-LEP construction, the procedure was similar to pcDNA3-FP2A-IAPP-LEP preparation using IN-FUSION™ reaction. Following pcDNA3 digestion by BamHI and NotI, the PCR product containing the LEP open reading frame (ORF) was sub-cloned into pcDNA3. pcDNA3-IAPP was produced by simple double enzyme digestion of the IAPP gene with EcoRI and NotI from an IAPP ORF-associated cDNA plasmid, followed by the insertion of the gene into linearized pcDNA3. The gene sequence of pcDNA3-FP2A-IAPP-LEP was confirmed by Sanger DNA sequencing for authenticity as SEQ ID NO: 10.

Figure 2:
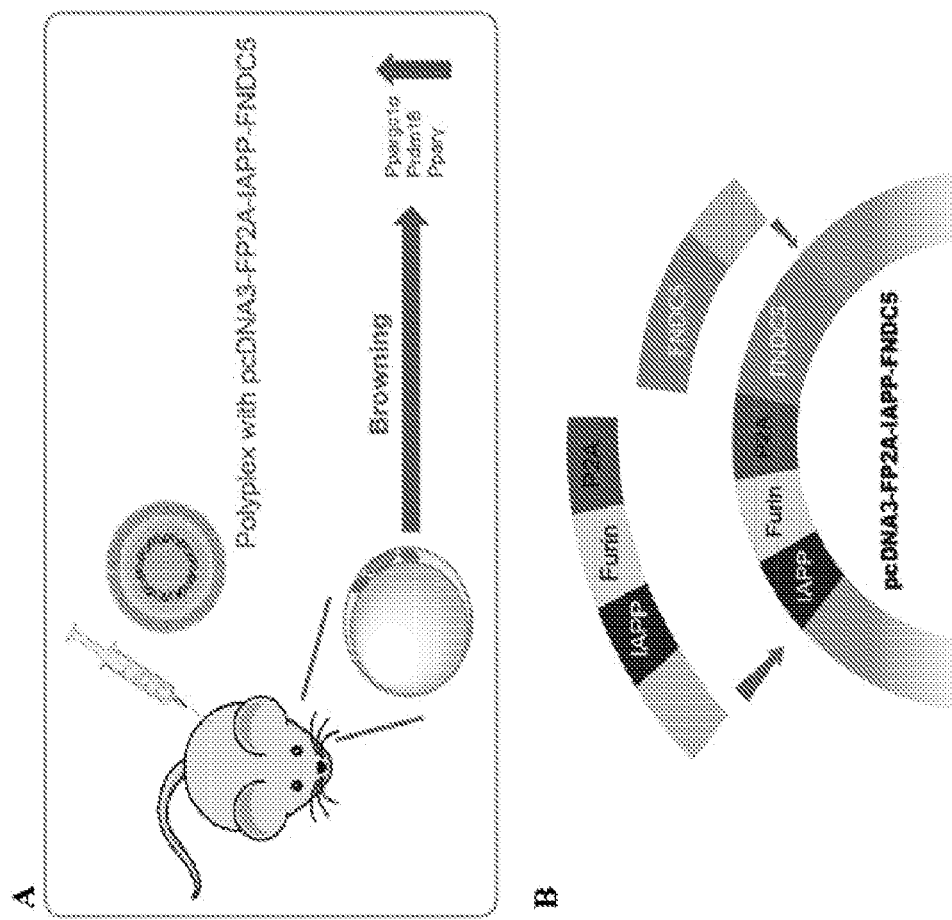
FIG. 2A is a diagram illustrating that administration of lPEI-pcDNA3-FP2A-IAPP-FNDC5 polyplex into a mouse induces the overexpression of three browning molecular determinants in white adipocytes.
FIG. 2B is a schematic representation of pcDNA3-FP2A-IAPP-FNDC5.

Plasmids referred to as pcDNA3-FNDC5 and pcDNA3-FP2A-IAPP-FNDC5 were prepared using mouse-originated IAPP and FNDC5 ORFs. To construct the bicistronic plasmid pcDNA3-FP2A-IAPP-FNDC5, the FNDC5 gene was obtained from pCR-blunt-TOPO-FNDC5 by double enzyme cut with BamHI and NotI, and ligated into pcDNA3, producing pcDNA3-FNDC5 (i.e., mono-cistronic pcDNA3-FNDC5). A schematic of the bicistronic plasmid is depicted in FIG. 2. Forward and reverse PCR primers were then designed which included a more than 15 base pair overlap with the neighboring segment of pcDNA3-FNDC5. The primers also contain translation initiation site (Kozak), restriction enzyme sites, and an FP2A linker gene. The primers also included more than 20 base pairs of IAPP ORF-complementary sequences. The primer sequences for pcDNA3-FP2A-IAPP-FNDC5 are provided in Table 2.

TABLE 2

| | |
| --- | --- |
| Forward primer | AGGGAGACCCAAGCTTAGAAA TGATGTGCATCTCCAAACTGCCAG (SEQ ID NO: 18) |
| Reverse primer | CGTTACTAGTGGATCCAGGCCCGGGGTTTTCTTCAACATC TCCTGCTTGCTTTAACAGAGAGAAGTTCGTGGCTCCGGAT CCCCTTTTTGCGCGAACGAGTAAGAAATCCAAGGATTCCC T (SEQ ID NO: 19) |

PCR was performed with the primers and IAPP cDNA plasmid, followed by the ligation of the PCR amplicon with linearized pcDNA3-FNDC5 using IN-FUSION™ reaction to complete pcDNA3-FP2A-IAPP-FNDC5 preparation (Zhu, B. et al., Biotechniques, 43: 354-359 (2007)). The plasmid pcDNA3-IAPP was generated as discussed above.

Figure 3A:
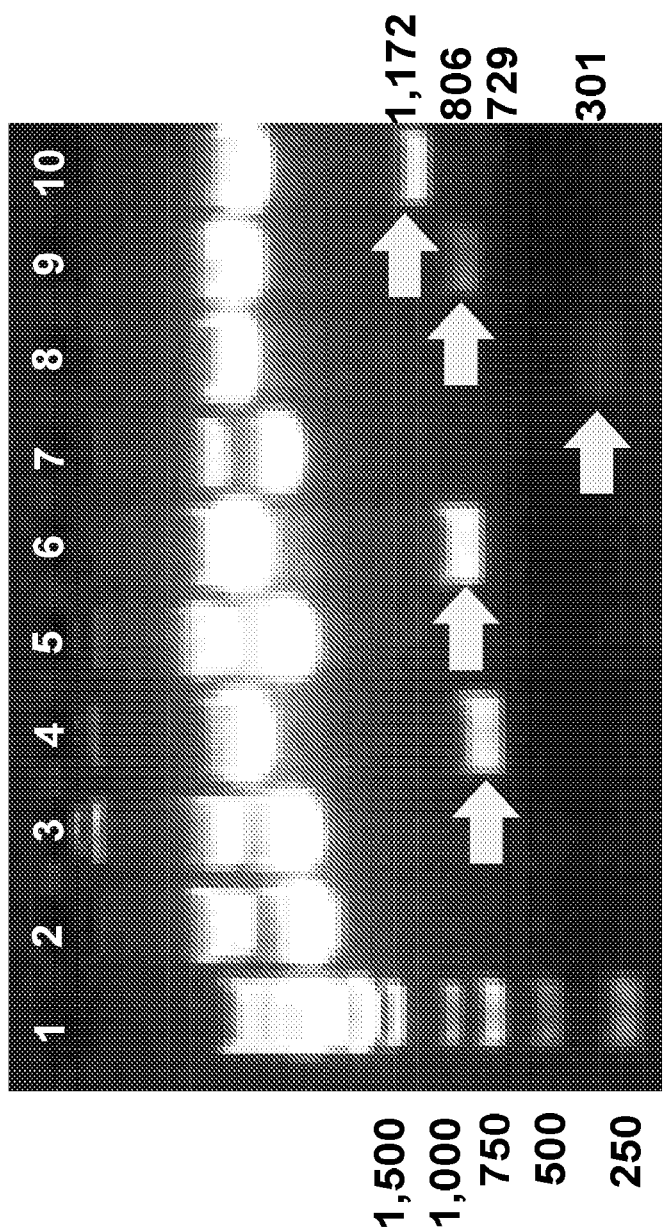
FIG. 3A is an image depicting results of restriction enzyme digestion-based gel electrophoresis to identify target gene inserts of constructed plasmids. The lanes are indicated as: lane 1 (size marker), lane 2 (pcDNA3), lane 3 (pcDNA3-IAPP), lane 4 (pcDNA3-IAPP cleaved by EcoRI and NotI), lane 5 (pcDNA3-FNDC5), lane 6 (pcDNA3-FNDC5 digested by BamHI and NotI), lane 7 (pcDNA3-FP2A-IAPP-FNDC5), lane 8 (pcDNA3-FP2A-IAPP-FNDC5 cut by HindIII and BamHI), lane 9 (pcDNA3-FP2A-IAPP-FNDC5 cleaved by BamHI and NotI), and lane 10 (pcDNA3-FP2A-IAPP-FNDC5 digested by HindIII and NotI). The numbers on the left side are the reference size, and the numbers on the right are DNA size by restriction enzyme digestion (301 bp: Kozak, IAPP, and furin ORF; 729 bp: IAPP gene from mouse cDNA; 806 bp: FNDC5 gene from mouse cDNA; 1172 bp: Kozak, IAPP, FP2A, and FNDC5 ORF).
Figure 3B:
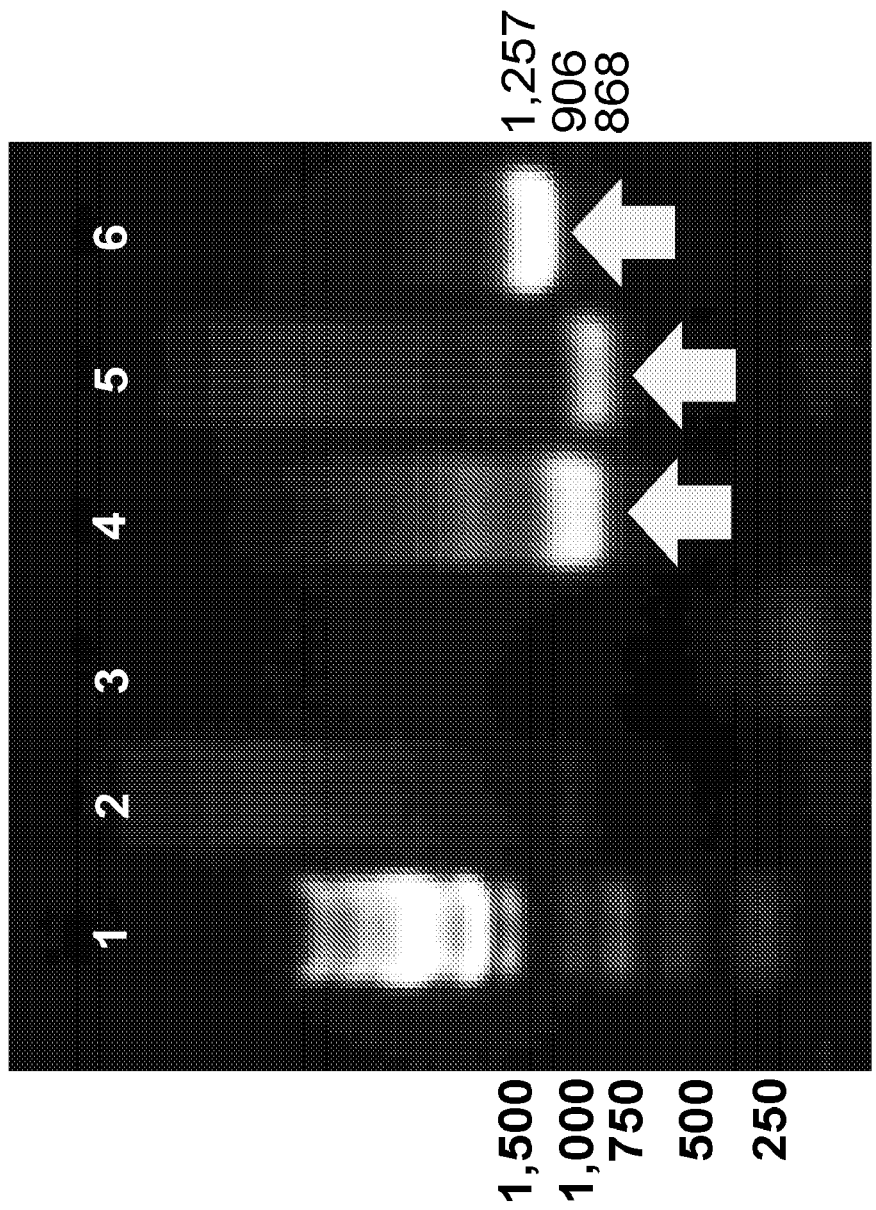
FIG. 3B is an image depicting the results of in vitro gene expression analysis using RT-PCR and gel electrophoresis. The lanes are indicated as: lane 1 (size marker), lane 2 (PCR product from non-treated HEK293T), lane 3 (PCR product from pcDNA3-treated HEK293T), lane 4 (PCR product from pcDNA3-FNDC5-treated HEK293T), lane 5 (PCR product from pcDNA3-IAPP-treated HEK293T), lane 6 (PCR product from pcDNA3-FP2A-IAPP-FNDC5-treated HEK293T). The numbers on the right side show the sizes of PCR products.

The gene sequence of pcDNA3-FP2A-IAPP-FNDC was confirmed by Sanger DNA sequencing for authenticity as SEQ ID NO: 11. Verification of plasmid construction was confirmed by a DNA sequencing assay.

pcDNA3-IAPP, pcDNA3-FNDC5, and pcDNA3-FP2A-IAPP-FNDC5 exhibited a correctly sized DNA product, and pcDNA3-FP2A-IAPP-FNDC5 exhibited a single transcript (FIG. 3B), as previously reported (Szymczak et al., *Expert Opin. Biol.*, 5: 627-638 (2005). Thus, it was demonstrated that total RNA extracted from the transfected cells showed the presence of mRNA corresponding to the insert for each target gene. Additionally, the transfected cells can express the transcript of full-length gene.

The results of this example confirm the construction of plasmids encoding IAPP and LEP or IAPP and FNDC5 in accordance with the invention.

Example 2

This example describes expression of the genes IAPP, LEP, and FNDC5 from plasmids generated in accordance with the invention.

Figure 3C:
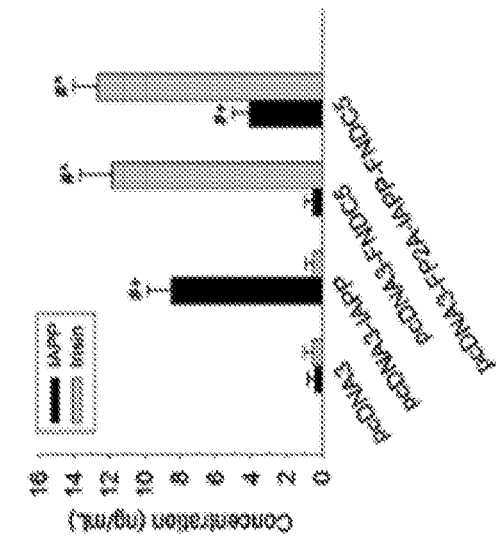
FIG. 3C is a graph illustrating IAPP and irisin expression from HEK293T medium by XFECT™-pDNA complexes (n ¼ 3).
Figure 3D:
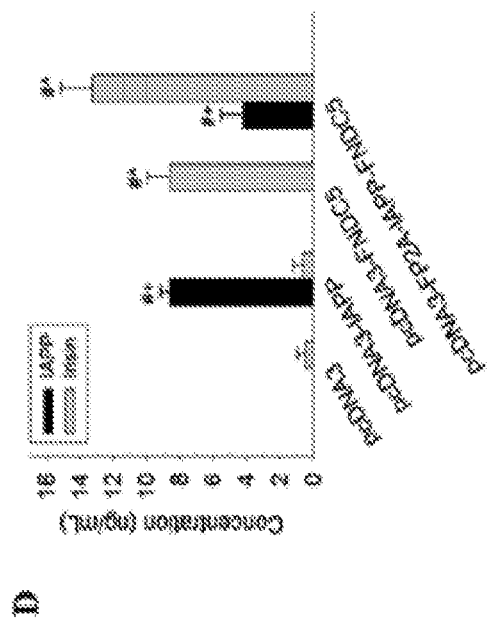
FIG. 3D is a graph illustrating IAPP and irisin expression from HEK293T medium by lPEI-pDNA polyplexes (n ¼ 3). Error bars in the graphs represent SEM, #P<0.05 vs. pcDNA3, P<0.05 vs. pcDNA3-FNDC5.
Figure 4A:
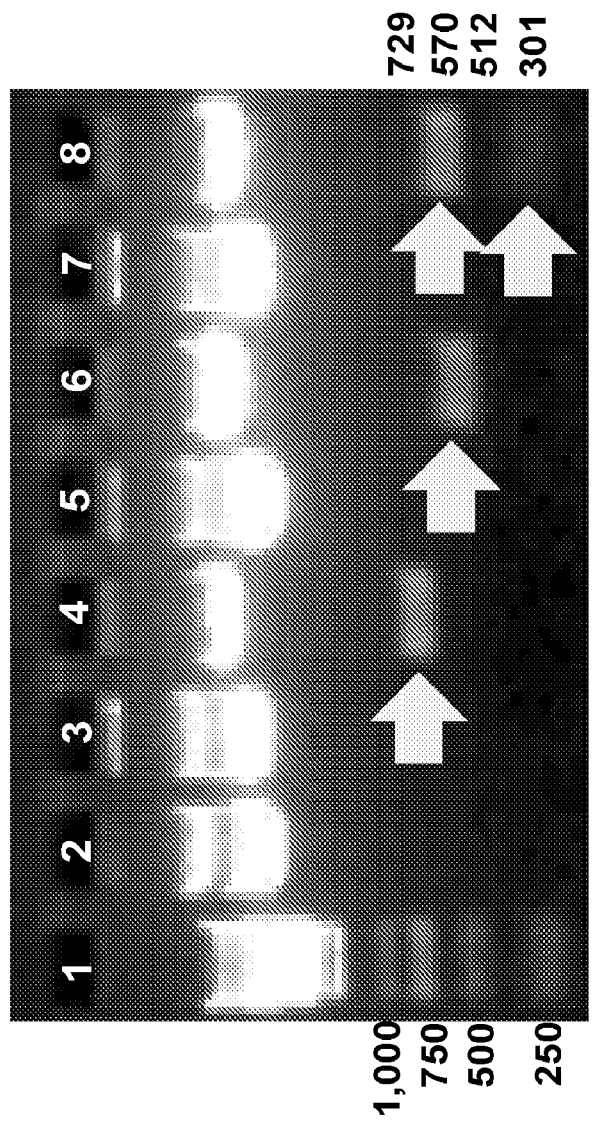
FIG. 4A is an image depicting results of restriction enzyme digestion-based gel electrophoresis to identify target gene inserts of constructed plasmids. The lanes are indicated as: lane 1 (size marker), lane 2 (pcDNA3), lane 3 (pcDNA3-IAPP), lane 4 (pcDNA3-IAPP digested by EcoRI and NotI), lane 5 (pcDNA3-LEP), lane 6 (pcDNA3-LEP cut by BamHI and NotI), lane 7 (pcDNA3-FP2A-IAPP-LEP), lane 8 (pcDNA3-FP2A-IAPP-LEP cleaved by BamHI and EcoRI). The numbers on the left side (typed in bold black) are the reference size from size marker. The numbers on the right side are the size of DNA bands generated by restriction enzymes (301 bp: Kozak, IAPP, and furin ORF, 512 bp: Kozak and LEP ORF, 570 bp: LEP and P2A ORF with stop codon, 729 bp: IAPP gene from mouse cDNA).

The presence and size of the insert of each of the plasmids described above was confirmed by restriction enzyme digestion and agarose gel electrophoresis, as shown in FIGS. 3 and 4.

Expression of the IAPP, LEP, and FNDC5 genes from each of the plasmids described in Example 1 was evaluated in HEK293T cells. Specifically, each plasmid was transduced by XFECT™ Transfection Reagent (Clontech, Mountain View, Calif.) into HEK293T cells (ATCC, Manassas, Va., USA) according to the manufacturer's protocol. HEK293T cells were cultured in DMEM (ATCC, Manassas, Va., USA), supplemented with 10% fetal bovine serum in 5% $CO_2$ humidified atmosphere at 37° C. Briefly, HEK293T cells were cultured in a six-well plate at an initial density of $5 \times 10^5$ per well for one day. 5 µg of pDNA complexed with 1.5 µl of XFECT™ was then added to the cells, followed by an additional two-day incubation. Cells were then harvested and centrifuged to obtain a cell pellet. Total RNA was extracted from the pellet using RNeasy Mini Kit (Qiagen, Valencia, Calif., USA). The first strand cDNA was synthesized from the RNA sample using M-MuLV Enzyme Mix and M-MuLV Reaction Mix (New England Biolabs). Subsequently, reverse transcriptase-polymerase chain reaction (RT-PCR) was completed with ONETAQ® RT-PCR Kit (New England Biolabs) and pcDNA3-complementary T7 and SP6 primers (obtained from the University of Utah Core Facility). Each RT-PCR product was analyzed by agarose gel electrophoresis.

To examine linear polyethylenimine (lPEI) as a non-viral gene delivery carrier, lPEI-pDNA polyplex nanoparticles were formed in HEPES buffer (20 mM) at N:P ratio of 5. The procedure with respect to the lPEI-pDNA polyplex addition for IAPP and LEP identification was the same as described above for XFECT™-pDNA complex transfection. In particular, the media from the no treatment cell group were used as a blank for EIA and ELISA. Following complexing pDNA with lPEI to generate a compacted polyplex, the polyplex presented as a nano-sized (approximately 100 nm) and positively charged complex (Table 3 and Table 4).

TABLE 3

| pDNA | Particle size (nm) | Polydispersity Index (PDI) | Zeta potential (mV) |
|---|---|---|---|
| pcDNA3 | 94.6 ± 0.9 | 0.135 ± 0.017 | 28.5 ± 1.0 |
| pcDNA3-IAPP | 107.1 ± 1.6 | 0.179 ± 0.031 | 27.7 ± 1.6 |
| pcDNA3-LEP | 99.9 ± 1.7 | 0.165 ± 0.013 | 29.2 ± 1.4 |
| pcDNA3-FP2A-IAPP-LEP | 103.6 ± 1.4 | 0.146 ± 0.026 | 28.2 ± 1.3 |

TABLE 4

| Plasmid (with lPEI) | Particle size (nm) | Polydispersity Index (PDI) | Surface charge (mV) |
|---|---|---|---|
| pcDNA3 | 95.9 ± 0.8 | 0.156 ± 0.027 | 26.2 ± 1.1 |
| pcDNA3-IAPP | 104.2 ± 2.5 | 0.189 ± 0.014 | 28.6 ± 0.6 |
| pcDNA3-FNDC5 | 91.6 ± 1.9 | 0.171 ± 0.022 | 27.2 ± 0.8 |
| pcDNA3-FP2A-IAPP-FNDC5 | 92.2 ± 1.5 | 0.165 ± 0.020 | 25.8 ± 1.9 |

Figures 4C, 4D:
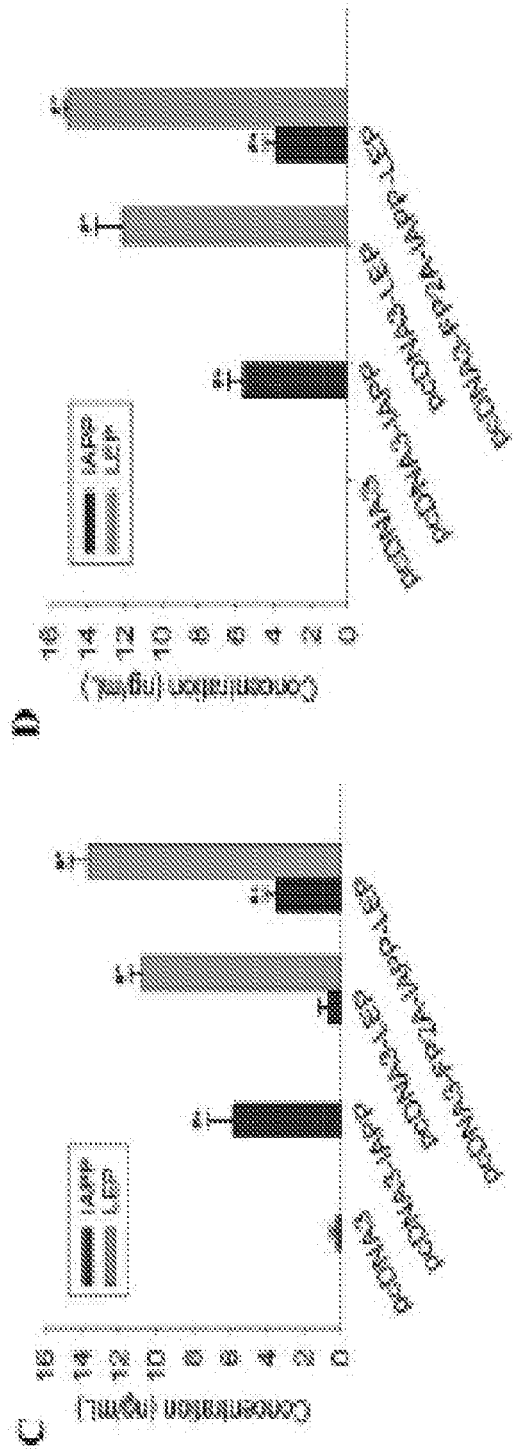
FIG. 4C is a graph illustrating IAPP and LEP gene expression by XFECT™-pDNA complexes in vitro (n=3).
FIG. 4D is a graph illustrating IAPP and LEP expression by lPEI-pDNA polyplexes in vitro (n=3). All grouped data are shown as means±SEM. #$P<0.05$ vs. pcDNA3, ^$P<0.05$ vs. pcDNA3-IAPP, +$P<0.05$ vs. pcDNA3-LEP, one-way ANOVA.

To evaluate protein expression from each of the plasmids, each plasmid was initially complexed with the in vitro gene carrier, XFECT™, and transfected into HEK293T cells initially. The concentrations of IAPP, LEP, and FNDC secreted into the culture medium were then measured. All of the plasmids expressed and secreted the proteins encoded therein (FIGS. 3C and 4C). In particular, both bicistronic plasmids pcDNA3-FP2A-IAPP-FNDC5 and pcDNA3-FP2A-IAPP-LEP co-expressed both IAPP and FNDC5 peptides and IAPP and LEP peptides, respectively, at similar molar concentrations due to the presence of the FP2A linker between the genes (Table 5 and Table 6).

TABLE 5

| pcDNA3-FP2A-IAPP-LEP | IAPP | LEP |
|---|---|---|
| Concentration (ng/mL) | 3.53 ± 0.99 | 13.68 ± 1.58 |
| Molecular weight (kDa) | ~4 | ~16 |
| Molar concentration (nM) | ~0.88 | ~0.86 |
| Molar concentration ratio | 1 | ~0.98 |

TABLE 6

| pcDNA3-FP2A-IAPP-FNDC5 | IAPP | Irisin |
|---|---|---|
| Concentration (ng/mL) | 4.10 ± 1.66 | 12.71 ± 2.32 |
| Molecular weight (kDa) | ~4 | ~13 |
| Molar concentration (nM) | ~1.03 | ~0.98 |
| Molar concentration ratio | 1 | ~0.95 |

To confirm that lPEI could be advanced as a gene carrier for in vivo studies, protein expression from plasmids complexed with lPEI was compared were compared to expression from the XFECT™-pDNA complexes. lPEI-pDNA polyplexes were transfected into HEK293T cells in the same manner as the commercial gene vehicle. Similar to the results from XFECT™ gene carrier, the genes delivered by lPEI were expressed as their secreted form of peptides. In particular, pcDNA3-FP2A-IAPP-LEP expressed both IAPP and LEP peptides in similar molar concentrations (FIG. 4D and Table 7), and pcDNA3-FP2A-IAPP-FNDC5 expressed both IAPP and irisin were co-expressed in equimolar concentrations (FIG. 3D and Table 8).

TABLE 7

| pcDNA3-FP2A-IAPP-LEP | IAPP | LEP |
|---|---|---|
| Concentration (ng/mL) | 3.92 ± 0.90 | 15.07 ± 0.36 |
| Molecular weight (kDa) | ~4 | ~16 |
| Molar concentration (nM) | ~0.98 | ~0.94 |
| Molar concentration ratio | 1 | ~0.96 |

TABLE 8

| pcDNA3-FP2A-IAPP-FNDC5 | IAPP | Irisin |
|---|---|---|
| Concentration (ng/mL) | 4.20 ± 2.31 | 13.25 ± 3.26 |
| Molecular weight (kDa) | ~4 | ~13 |
| Molar concentration (nM) | ~1.05 | ~1.02 |
| Molar concentration ratio | 1 | ~0.97 |

The results of this example confirm that the plasmids pcDNA3-FP2A-IAPP-LEP and pcDNA3-FP2A-IAPP-FNDC5 express the proteins encoded therein in vitro and that the lPEI-pDNA polypeptides were suitable for further in vivo applications.

Example 3

This example describes in vivo gene delivery of the pcDNA-FP2A-IAPP-LEP plasmid and resulting changes in body weight and food consumption.

To determine the most suitable frequency and dose of lPEI-pDNA polyplexes, the polyplexes were first administered intraperitoneally (i.p.) to lean mice. The lPEI-pDNA polyplex containing the IAPP gene (lPEI complexed with pcDNA3-IAPP or with pcDNA3-FP2A-IAPP-LEP) and the polyplex containing the LEP gene (lPEI complexed with pcDNA3-LEP or with pcDNA3-FP2A-IAPP-LEP) displayed much higher concentrations in serum of treated mice as compared to untreated mice on day 1 and day 3 post-administrations. However, after one week, protein levels prominently declined. Moreover, weight loss was observed in treated mice, and reached a plateau or began to slightly reverse after one week. Thus, weekly polyplex administrations were chosen for further studies using diet induced obese (DIO) mice. Circulating hormone concentration and weight loss were not found to be significantly different between the 45 µg and 60 µg doses of plasmid DNA. Therefore, 45 µg of pDNA with lPEI was determined as an optimal dose for subsequent experiments in DIO mice to avoid any potential hepatotoxicity (Kim et al., *PLoS One* 6: e18556 (2011)) and Zhu et al., *Biotechniques*, 43: 354-359 (2007)).

Figure 5A:
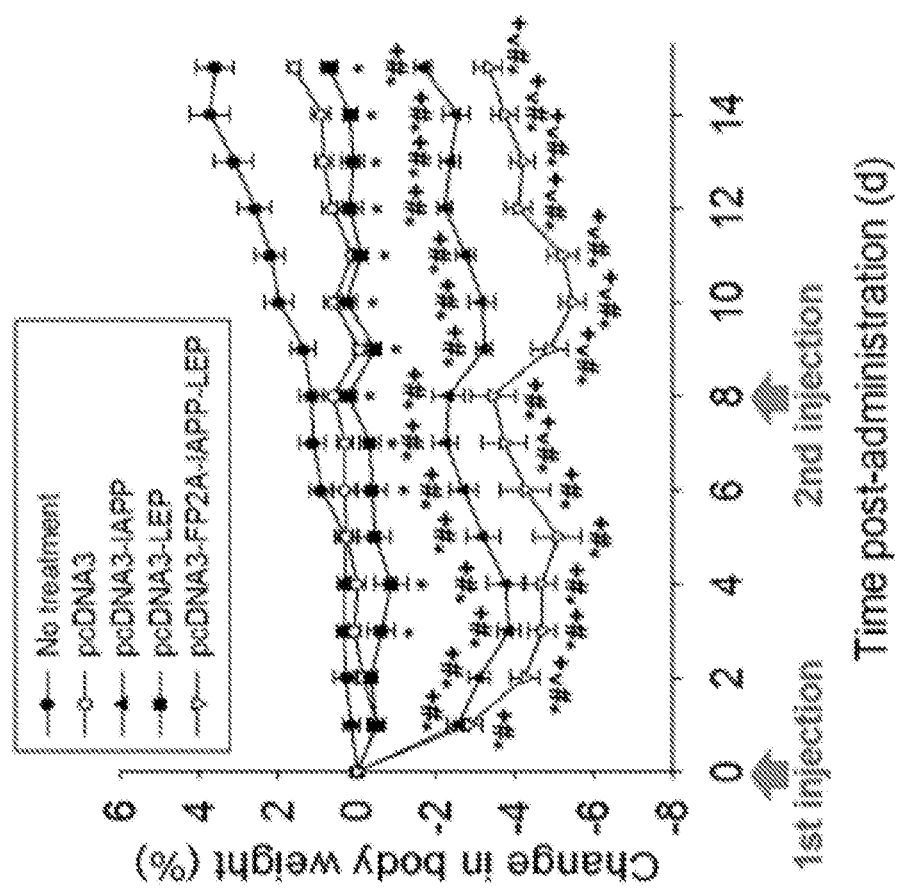
FIG. 5 contains graphs illustrating body weight changes (5A) and average daily food intake (5B) in DIO mice following administrations of lPEI-pDNA polyplexes (n=8) monitored throughout the experimental periods.
FIG. 5C is a graph illustrating the synergy index of lPEI-pcDNA3-FP2A-IAPP-LEP polyplex treatments in DIO mice. Data are shown as the means±SEM. *$P<0.05$ vs. no treatment, #$P<0.05$ vs. pcDNA3, ^$P<0.05$ vs. pcDNA3-IAPP, +$P<0.05$ vs. pcDNA3-LEP, one-way ANOVA.

DIO mice were then treated twice (on days 0 and 8) with lPEI-pcDNA3, pcDNA3-IAPP, pcDNA3-LEP, and bicistronic pcDNA3-FP2A-IAPP-LEP (45 µg per plasmid). After treatment, no mice died and there were no modifications in behavior, appearance, or mobility, indicating the safety of the polyplexes. During the treatment, the bicistronic plasmid polyplex exhibited the greatest inhibition of both weight gain and food intake (FIGS. 5A-B). In addition, mice receiving the bicistronic pDNA polyplex exhibited weight loss that resulted in a visible size decrease. lPEI-pcDNA3-IAPP polyplex also exhibited a greater reduction in both body weight and food intake as compared to no treatment, or treatment with lPEI-pcDNA3 or lPEI-pcDNA3-LEP, which is consistent with previous reports (Uldry et al., *Cell Metab.*, 3: 333-341 (2006), Seale. et al., *J. Clin. Invest.* 121: 96-105 (2011), and Urban-Klein et al., *Gene Ther.* 12: 461-466 (2005)). Additionally, the lPEI-pcDNA3-LEP treatment group did not show a sharp dip in either weight or food intake due to the intrinsic LEP resistance in DIO mice (Uldry et al., supra, and Sadry et al., *Nat. Rev. Endocrinol.*, 5 (2014)). While no treated mice showed a constant increase in body weight, lPEI-pcDNA3-treated mice displayed a more sluggish weight gain, possibly due to the distress caused by the injections of lPEIpcDNA3 polyplex (Kim et al, *PLoS One*, 6: e18556 (2011). However, the weight changes resulting from the lPEI-pcDNA3 polyplex administrations were negligible in comparison with the weight changes that occurred following treatment with the lPEI-pcDNA3-FP2A-IAPP-LEP polyplex.

Rothman's synergy index (S) was calculated to determine whether the lPEI-pcDNA3-FP2A-IAPP-LEP polyplex exhibited a synergistic effect on body weight loss in DIO mice. In this index, exactly additive results indicate that there is no synergistic effect of the combination of two therapeutic agents (here, IAPP and LEP). Rothman's synergy index was calculated as follows:

Control odds=the average change in body weight of
lPEI-pcDNA3-treated DIO mice group (%)÷
[(100−the average change in body weight of
lPEI-pcDNA3-treated DIO mice group (%))]

Treatment odds=the average change in body weight
of lPEI-pcDNA3-IAPP, -pcDNA3-LEP, or
pcDNA3-FP2A-IAPP-LEP-treated DIO mice
group (%)÷[(100−the average change in body
weight of lPEI-pcDNA3-IAPP, -pcDNA3-LEP,
or -pcDNA3-FP2A-IAPP-LEP-treated DIO mice
group (%))]

Figure 5C:
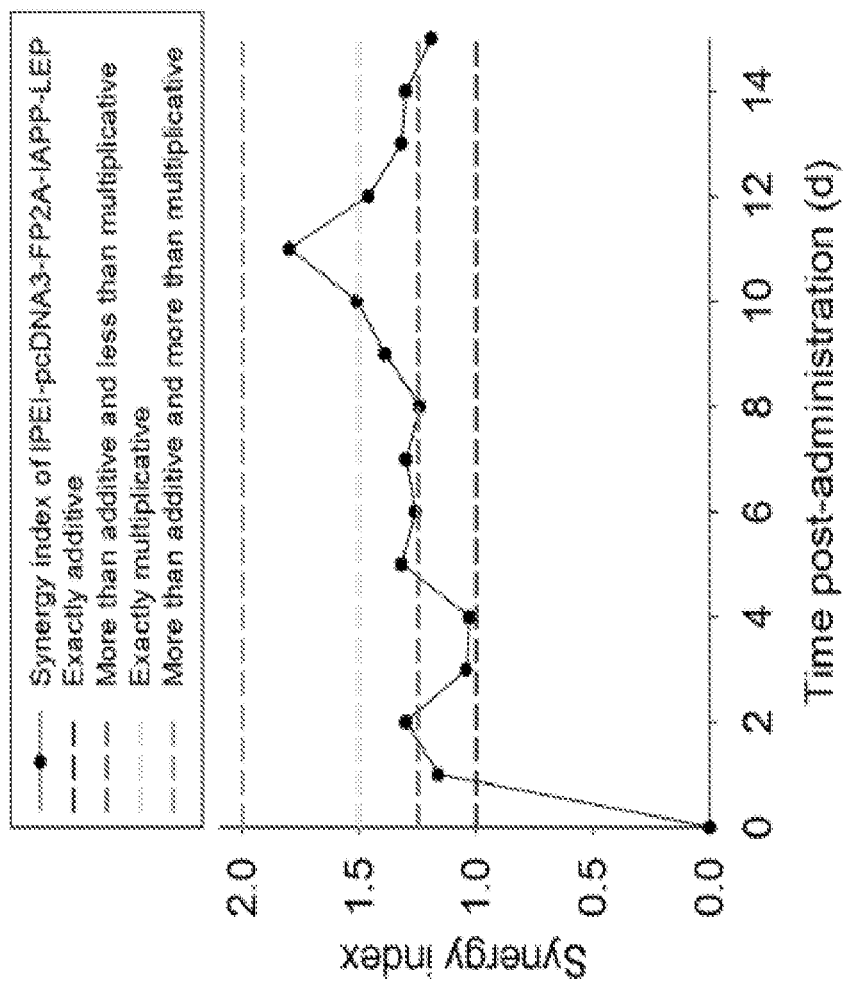

Odds Ratio=Treatment odds÷Control odds $S=(ORIL-1) \div [(ORI+ORL)-2]$ where ORIL indicates
the OR of lPEI-pcDNA3-FP2A-IAPP-LEP-administered DIO mice group, OR means the OR
of lPEI-pcDNA3-IAPP-injected DIO mice group, and ORL is the OR of lPEI-pcDNA3-LEP-treated DIO mice group During the time period of from 1-7 days following the first administration, lPEI-pcDNA3-FP2A-IAPP-LEP polyplex treatment appeared to produce more than an additive and less than a multiplicative interaction. Furthermore, during the period of from 9-15 days following the second administration, exactly multiplicative synergism was observed (FIG. 5C).

The results of this example confirm that in vivo delivery of the pcDNA-FP2A-IAPP-LEP plasmid conjugated to a non-viral carrier exerts a synergistic effect on body weight loss in DIO mice.

Example 4

This example describes the effects of in vivo delivery of lPEI-pcDNA3-FP2A-IAPP-LEP on circulated hormones and obesity-related metabolic variables in the blood of treated mice.

Figure 6:
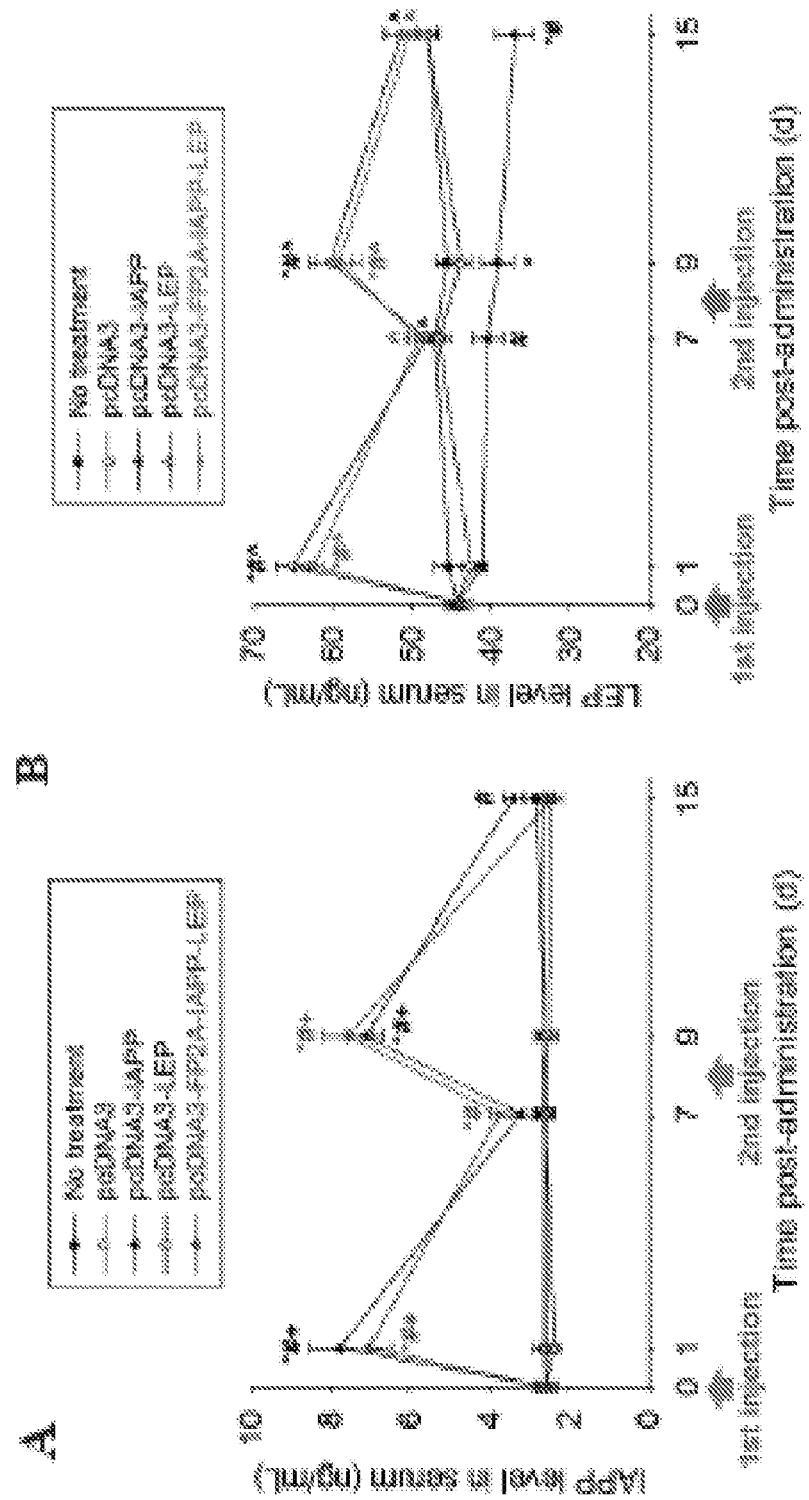
FIG. 6 are graphs illustrating serum protein levels of IAPP (6A) (n=6) and LEP (6B) (n=6) in DIO mice for 15 days following polyplex administrations. Data are shown as the means±SEM. *$P<0.05$ vs. no treatment, #$P<0.05$ vs. pcDNA3, ^$P<0.05$ vs. pcDNA3-IAPP, +$P<0.05$ vs. pcDNA3-LEP, one-way ANOVA.

To identify physiological changes in DIO mice following the administrations of lPEI-pcDNA3-FP2A-IAPP-LEP polyplex as described in Example 3, IAPP and LEP protein levels in serum samples were detected using an IAPP EIA kit and a LEP ELISA kit (Phoenix Pharmaceuticals), respectively (FIG. 6A-B). Consistent with data from lean mice, the DIO mice showed highly elevated levels of both IAPP and LEP protein 1 day following the first and second lPEI-pcDNA3-FP2A-IAPP-LEP polyplex injections; however, the levels decreased gradually after about one week. This decrease correlated with the changes in body weight, with stagnant weight loss observed after a week (FIG. 5A). Based on the results from lean and DIO mice, it was concluded that lPEI-pcDNA3-FP2A-IAPP-LEP can successfully produce each peptide in vivo.

For blood glucose measurements, about five microliters of blood drawn from the tail vein of 6-hour fasted DIO mice was placed onto a glucose test strip (American Diabetes Wholesale) and glucose levels were measured using a blood glucose meter (Bayer Contour). Before polyplex treatments, the initial blood glucose level of all mice was between 170-220 mg/dL. Treatment with the lPEI-pcDNA3-FP2A-IAPP-LEP polyplex led to significant decreases in blood glucose levels as compared to no treatment, lPEI-pcDNA3, and lPEI-pcDNA3-LEP polyplex treatment groups (FIG. 7A).

Figure 7B:
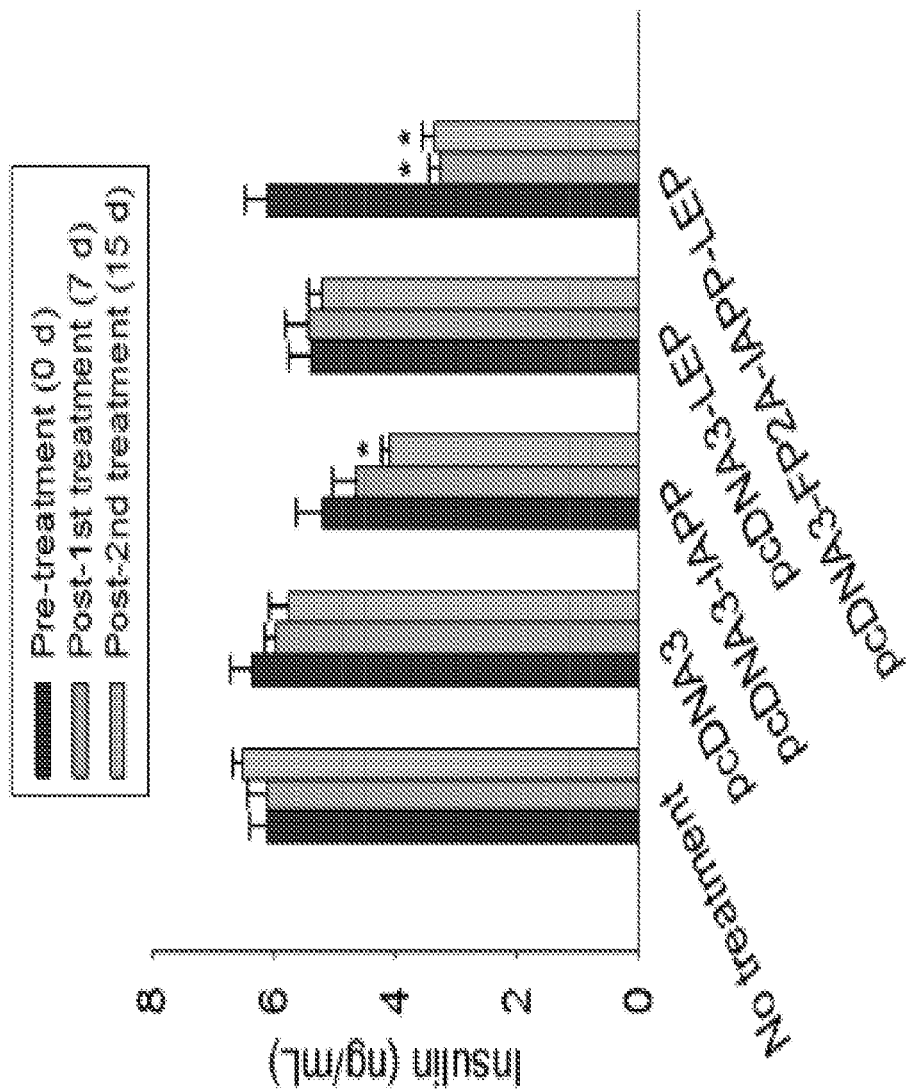
FIG. 7B shows serum insulin levels (n=6)

The levels of serum insulin, free fatty acids, and triglycerides were measured by Mouse Insulin ELISA Kit (Crystal Chem), FFA test kit (Roche), and TG assay solutions (Wako Diagnostics, Richmond, Va., USA), respectively. Two weekly injections of the lPEI-pcDNA3-FP2A-IAPP-LEP polyplex resulted in a significant decrease of circulating levels of insulin (FIG. 7B). In addition, both circulating free fatty acids (FIG. 7C) and triglycerides (FIG. 7D) also were significantly reduced relative to the pre-treatment state.

The results of this example demonstrate that treatment with the lPEI-pcDNA3-FP2A-IAPP-LEP polyplex decreases the levels of glucose, insulin, and lipid concentrations in mouse blood.

Example 5

This example describes changes in adiposity in DIO mice after treatment with the lPEI-pcDNA3-FP2A-IAPP-LEP polyplex.

Two representative white adipose tissues (WATs) were prepared, i.e., visceral epididymal white adipose tissue (Epi- WAT) and subcutaneous inguinal white adipose tissue (Ing-WAT), from DIO mice on day 15 after euthanasia. The weight percentage of each adipose type was quantified by the weight of each WAT divided by total body weight×100.

Figure 8A:
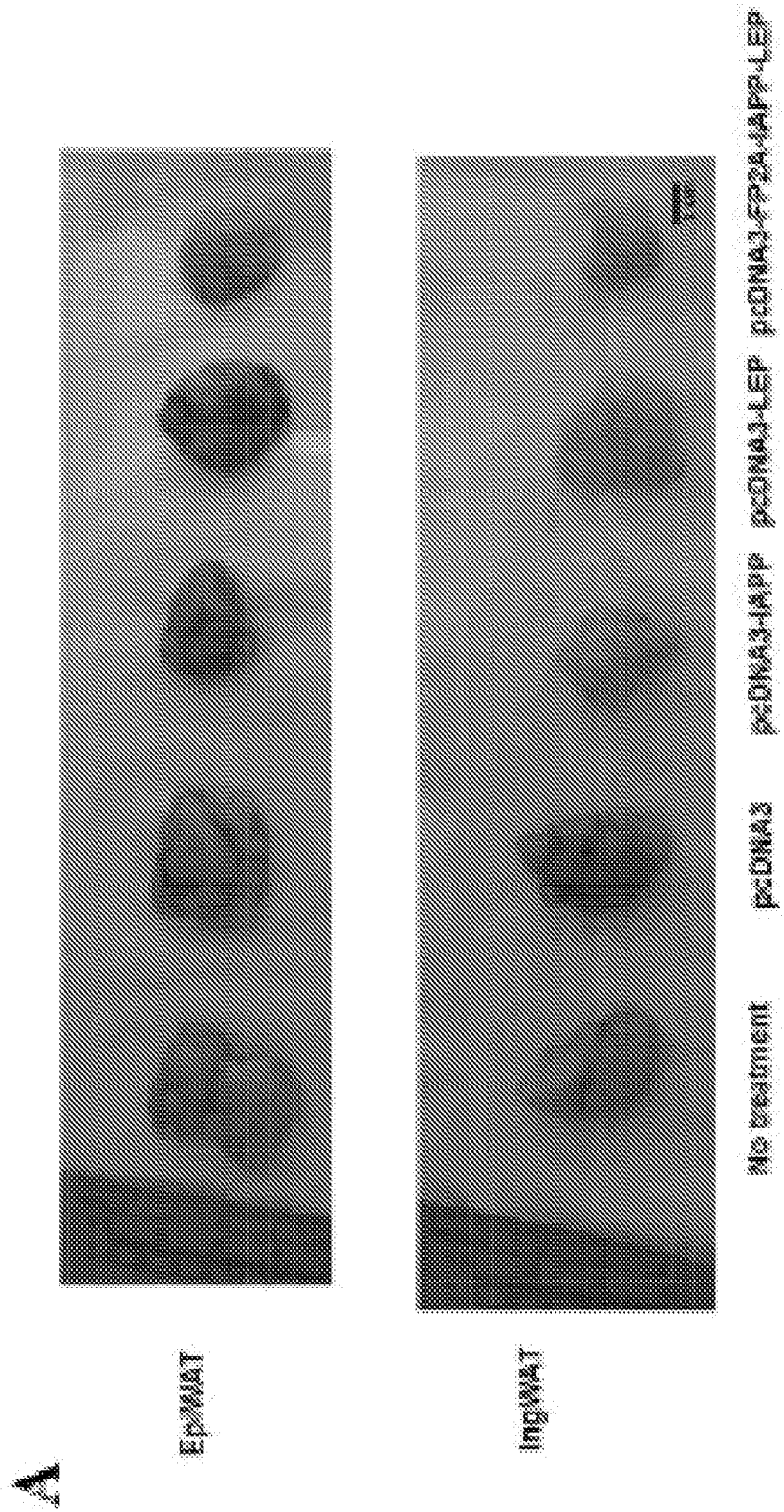
FIG. 8A is an image of EpiWAT and IngWAT 15 days after two lPEI-pDNA polyplex administrations (n=5).
Figure 8C:
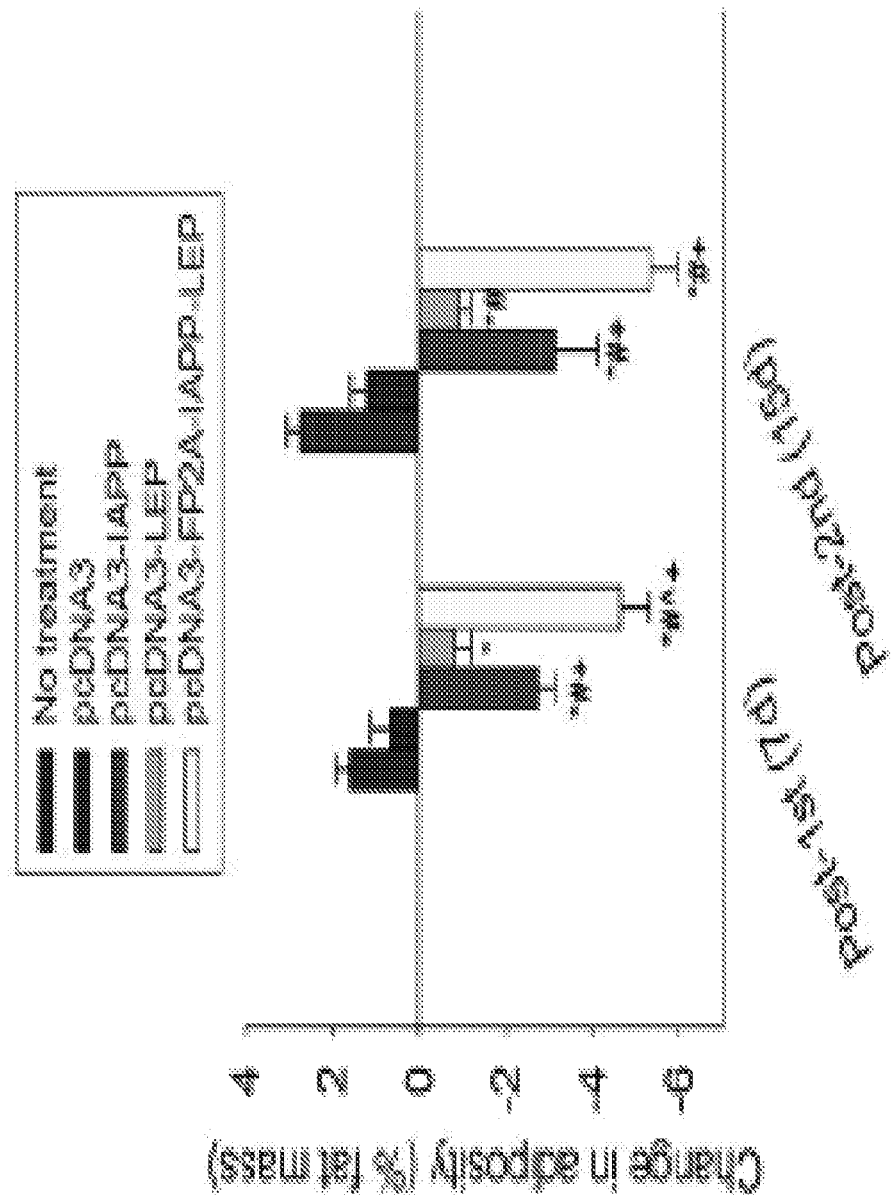
FIG. 8C is a graph illustrating changes in total adiposity compared to the pre-injection state (n=7).

To elucidate the effects of the lPEI-pcDNA3-FP2A-IAPP-LEPpolyplex treatment on changes in adiposity of DIO mice, mouse size and weight (%) of EpiWAT and IngWAT were analyzed on day 15. Both WATs appeared significantly smaller and lighter in the mice treated with either lPEI-pcDNA3-IAPP or the lPEI-pcDNA3-FP2A-IAPP-LEP polyplex as compared to other groups (FIGS. 8A-B). In particular, the mass of IngWAT from mice treated with the lPEI-pcDNA3-FP2A-IAPP-LEP polyplex was approximately half of that of two controls (i.e., un-treated and lPEI-pcDNA3-treated groups). Although the pcDNA3-FP2A-IAPP-LEP polyplex injections resulted in a greater decrease of total body adiposity relative to the other groups (FIG. 8C), total dry lean mass did not decrease (FIG. 8D). The reduction of body adiposity is consistent with the decrease observed in lipid concentrations in blood circulation resulting from lPEI-pcDNA3-FP2A-IAPP-LEP polyplex treatment (FIGS. 7C-D).

The results of this example describe the changes in adiposity in DIO mice after treatment with the lPEI-pcDNA3-FP2A-IAPP-LEP polyplex.

Example 6

This example describes the effects of in vivo delivery of lPEI-pcDNA3-FP2A-IAPP-LEP on indirect calorimetry in mice.

The ability of bicistronic plasmid polyplex administrations to increase energy expenditure in DIO mice was evaluated. Following injection of lPEI-pcDNA3 (control), lPEI-pcDNA3-IAPP, lPEI-pcDNA3-LEP, and the lPEI-pcDNA3-FP2A-IAPP-LEP polyplex into DIO mice, oxygen consumption ($VO_2$), carbon dioxide production ($VCO_2$), respiratory exchange ratio (RER; $VCO_2/VO_2$), and heat generation were measured by an indirect calorimetry system (Columbus Instruments) for three days. All the DIO mice in each chamber had free access to high-fat diet (HFD) and water during the assay.

Metabolic changes induced by the bicistronic plasmid polyplex during the first three days, i.e., the time period in which an active weight loss occurred, were investigated (FIG. 5A). The metabolic chamber assay revealed that the weight reduction induced by the lPEI-pcDNA3-FP2A-IAPP-LEP polyplex was associated with an increase in a marker of metabolic rate, $VO_2$ (FIG. 9A), and heat generation (FIG. 9B). Moreover, the RER ($VCO_2$ to $VO_2$) was significantly reduced in bicistronic plasmid polyplex-treated mice relative to pcDNA3 and pcDNA3-LEP polyplex-treated animals (FIG. 9C). These results suggest that fat metabolism as the energy fuel production was increased during the initial three days, resulting in fat dissipation.

The results of this example demonstrates that in vivo delivery of the lPEI-pcDNA3-FP2A-IAPP-LEP polyplex increased oxygen consumption ($VO_2$), carbon dioxide production ($VCO_2$), RER ($VCO_2/VO_2$), and heat generation in mice.

Example 7

This example describes in vivo gene delivery of the pcDNA-FP2A-IAPP-FNDC5 plasmid and its effects on browning efficacy in mice.

Figure 10:
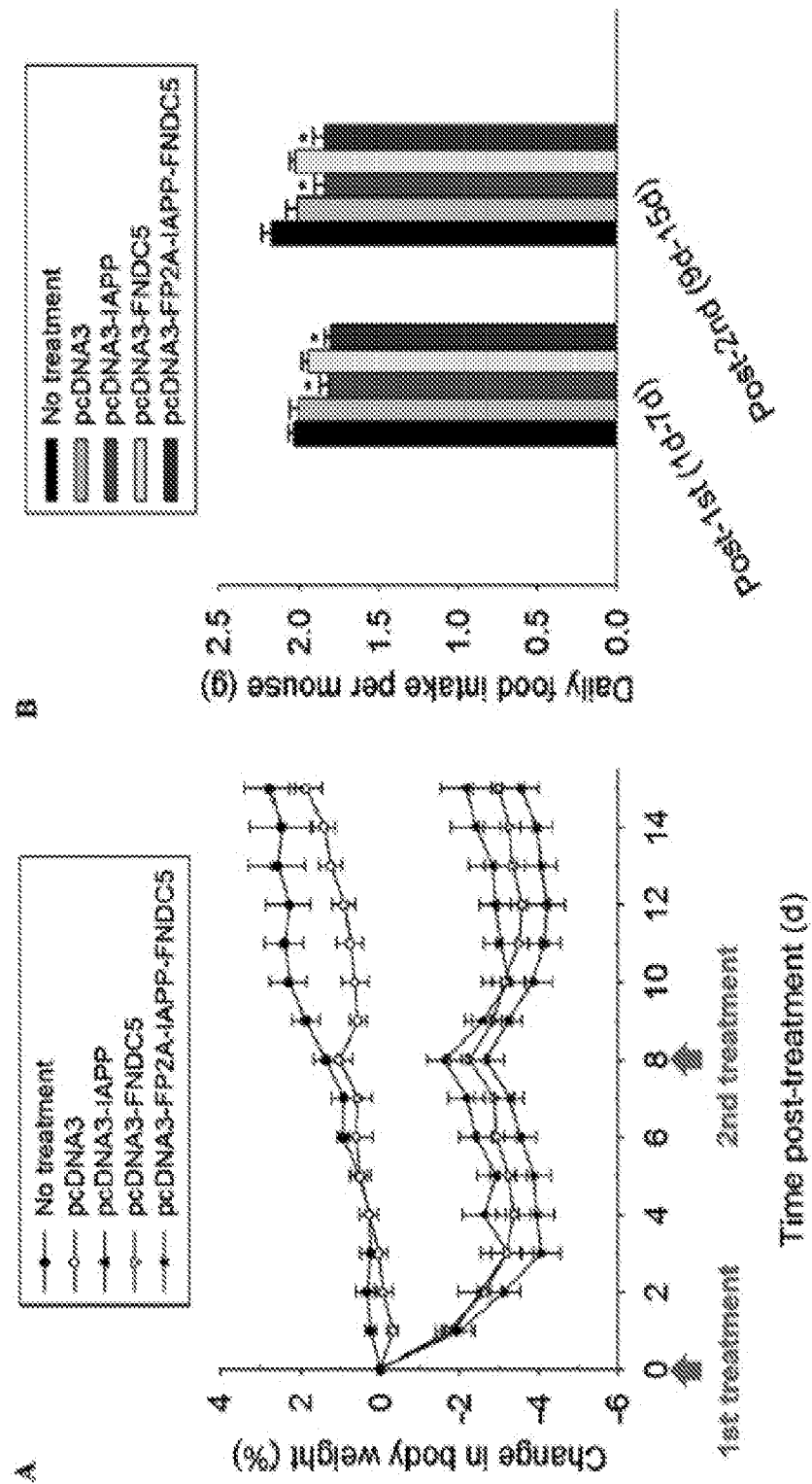
FIG. 10A is a graph illustrating changes in body mass in DIO mice following the administration of lPEI-pcDNA3, lPEI-pcDNA3-IAPP, lPEI-pcDNA3-FNDC5, and lPEI-pcDNA3-FP2A-IAPP-FNDC5 polyplexes. All three experimental groups (pcDNA3-IAPP, pcDNA3-FNDC5, and pcDNA3-FP2A-IAPP-FNDC5) are statistically significant ($P<0.05$) against both control groups (no treatment and pcDNA3) at all-time points.
FIG. 10B is a graph illustrating average daily food consumption after the first and second treatments with polyplexes. All data are means±SEM, n=6 per group, *$P<0.05$ vs. no treatment.

DIO mice were intraperitoneally injected twice (on days 0 and 8) with the polyplexes lPEI-pcDNA3-IAPP, lPEI-pcDNA3-FNDC5, or lPEI-pcDNA-FP2A-IAPP-FNDC5 body weights were measured daily. FIG. 10A shows the loss of body weight achieved by the pDNAs delivered by lPEI. Throughout the treatment period, DIO mice treated with lPEI-pcDNA3-FP2A-IAPP-FNDC5 exhibited the greatest decrease in body weight. The change in body weight was most pronounced during the initial three days after both the first and second treatments. In contrast, the untreated DIO mice and DIO mice treated with the lPEI-pcDNA3 polyplex exhibited constant body weight gain due to their palatable HFD feeding (FIG. 10A). Although the body weight gain in untreated DIO mice was somewhat higher than that of the lPEI-pcDNA3-treated group, possibly due to the distress by polyplex injection (Park et al., *J. Control. Release,* 207: 154-162 (2015) and Bonnet et al., *Pharm. Res.* 25: 2972-2982 (2008)), the difference between these groups was not statistically significant.

A significant reduction of food consumption occurred in DIO mice treated with lPEI-pcDNA3-IAPP and lPEI-pcDNA3-FP2A-IAPP-FNDC5 (FIG. 10B). Although the treatment with the lPEI-pcDNA3-FNDC5 polyplex led to noticeable loss of body weight in DIO mice (FIG. 10A), it did not significantly decrease the amount of food intake. Indeed, food intake following treatment with the lPEI-pcDNA3-FP2A-IAPP-FNDC5 polyplex was similar to that observed following treatment with monocistronic pcDNA3-IAPP (FIG. 10B).

DIO mice treated with lPEI-pcDNA3-FNDC5 appeared hyperphagic, suggesting that body weight reduction by lPEI-pcDNA3-FNDC5 and lPEI-pcDNA3-FP2A-IAPP-FNDC5 may primarily result from browning-related energy metabolism rather than reduced food intake.

Figure 11:
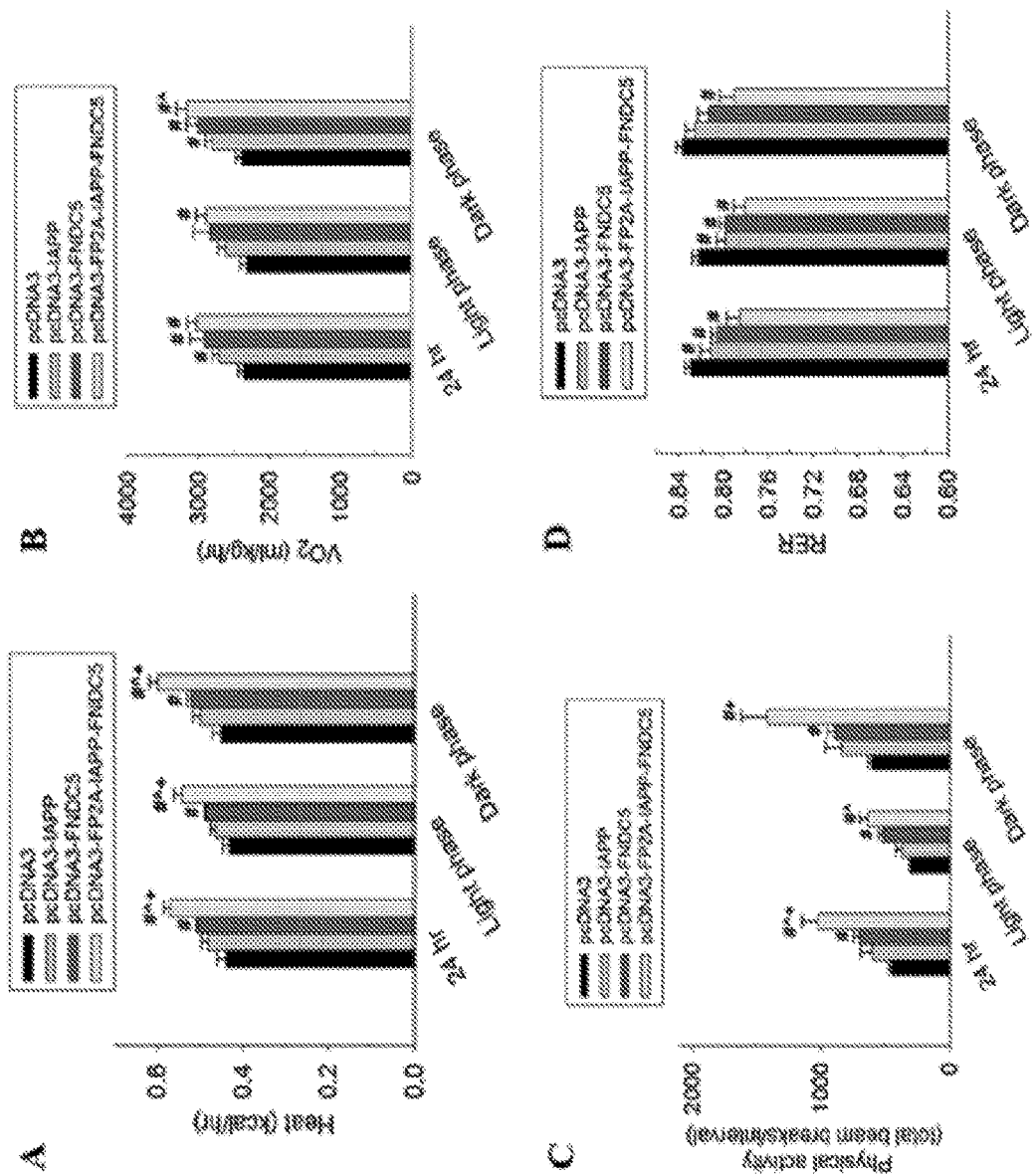
FIG. 11 includes graphs illustrating increased energy expenditure (11A), elevated oxygen consumption (11B), increased physical activity (11C), and RER (11D) by the lPEI-pcDNA3-FP2A-IAPP-FNDC5 polyplex during three days of treatment. Error bars in the graph represent SEM, n ¼ 4 per group. #$P<0.05$ vs. pcDNA3, ^$P<0.05$ vs. pcDNA3-IAPP, +$P<0.05$ vs. pcDNA3-FNDC5.

In order to better understand the mechanism underlying decreased body weight in DIO mice treated with the FNDC5 gene, a metabolic chamber assay was conducted to measure the energy expenditure, oxygen consumption (a marker of metabolic rate), and physical mobility of the animals treated with pDNAs containing the FNDC5 gene (i.e., lPEI-pcDNA3-FNDC5 and l-PEI-pcDNA3-FP2A-IAPP-FNDC5). To this end, after the administration of polyplexes, changes related to energy metabolism were detected during the first three days after administration, when active body weight reduction was prominent (FIG. 10A). As shown in FIG. 11, heat generation was significantly increased in DIO mice treated with the lPEI-pcDNA3-FP2A-IAPP-FNDC5 polyplex as compared to all the other groups. In accordance with the escalation of thermogenesis, oxygen consumption and physical activity were also noticeably increased in DIO mice administered with lPEI-pcDNA3-FP2A-IAPP-FNDC5. lPEI-pcDNA3-FNDC5 also significantly increased heat production, oxygen consumption, and movement as compared to lPEIpcDNA3, the experimental control, in DIO mice. These results suggest that, although lPEI-pcDNA3-FNDC5 did not suppress food intake in DIO mice, it produced an increase in energy metabolism, which led to the decline in body weight (FIG. 10A). Because decreased spontaneous physical exercise and the consequent decrease in thermogenesis derived from non-exercise activity are prevalent globally, these results also suggest that FNDC5 may contribute to the inhibition of obesity in humans (Levine et al., *Science,* 283: 212-214 (1999)).

Treatment with lPEI-pcDNA3-IAPP polyplex produced a significant increase in oxygen consumption and a small increase in heat production and movement. In addition, the respiratory exchange ratio (RER) was significantly decreased after the therapeutic gene polyplex treatments, indicating that the polyplexes altered energy source selection between carbohydrate and fatty acids. However, the RER did not differ between single and dual browning gene polyplexes, suggesting that the combinatorial gene polyplex's preference for carbohydrate and fatty acid usage as fuel source was similar to the single-gene polyplexes.

Figure 12:
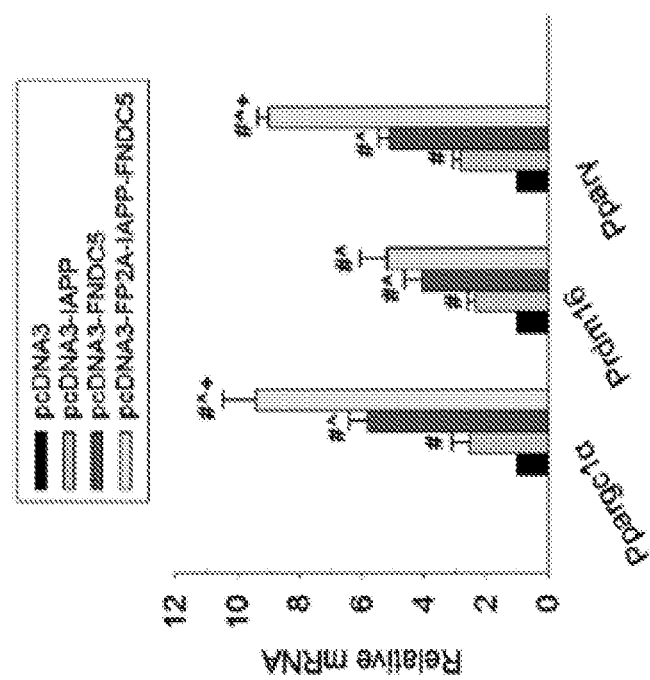
FIG. 12 is a graph illustrating gene expression in IngWAT from DIO mice. The enhanced expression levels of Ppargc1a, Prdm16, and Pparg were determined after treatment with the lPEI-pcDNA3-FP2A-IAPP-FNDC5 polyplex. Error bars in the graph represent SEM, n ¼ 5 per group. #$P<0.05$ vs. pcDNA3, ^$P<0.05$ vs. pcDNA3-IAPP, +$P<0.05$ vs. pcDNA3-FNDC5.

The above data indicate that the lPEI-pcDNA3-FP2A-IAPP-FNDC5 polyplex was the most effective in elevating energy metabolism via heat generation and physical mobility as compared to the other tested plasmids. Consistent with increased energy metabolism, lPEI-pcDNA3-FP2A-IAPP-FNDC5-treated DIO mice exhibited significant increased expression of three major browning gene markers: Ppargc1a, Prdm16, and Pparg, at three days after administration (FIG. 12). This observation suggests that the increase in heat generation induced by pcDNA3-FP2A-IAPP-FNDC5 (FIG. 11A) is associated with enhanced thermogenesis mediated by molecular determinants of browning. In addition, pcDNA3-IAPP and pcDNA3-FNDC5 produced elevated expression profiles of thermogenic program-related genes.

Figure 13:
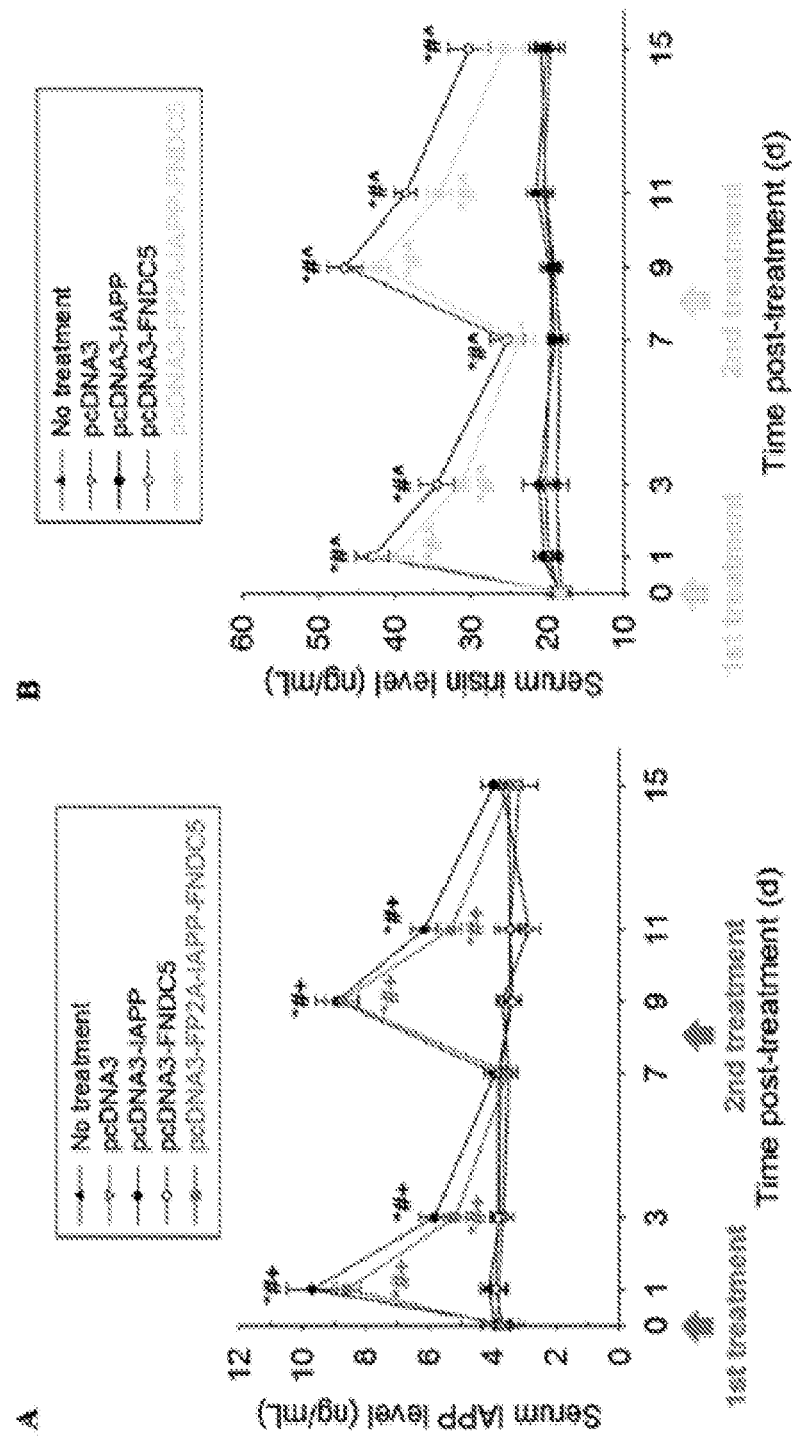
FIG. 13 includes graphs illustrating IAPP (13A) and irisin (13B) serum protein levels in DIO mice injected with the indicated polyplex. Data represent means±SEM, n ¼ 5 per group. *$P<0.05$ vs. No treatment, #$P<0.05$ vs. pcDNA3, A$P<0.05$ vs. pcDNA3-IAPP, +$P<0.05$ vs. pcDNA3-FNDC5.

The levels of both IAPP and irisin in blood serum from DIO mice was measured (FIG. 13). IAPP was significantly produced from lPEIpcDNA3-IAPP and lPEI-pcDNA3-FP2A-IAPP-FNDC5-treated DIO mice, and irisin was significantly produced from lPEI-pcDNA3-FNDC5 and lPEI-pcDNA3-FP2A-IAPP-FNDC5-treated DIO mice after one and three days of their administrations. These results are consistent with the data regarding body weight loss described above (FIG. 10A), because the changes in body weight peaked during the initial three days and leveled off after a week. Weekly treatment of DIO mice with lPEI-pcDNA3-FP2A-IAPP-FNDC5 exhibited a reduction of body weight and sufficient levels of browning hormones, consistent with previous reports (Park et al., supra). Although the rate of body weight loss slowed after three days post-treatment, the difference in body weight changes between the two control cohorts and the lPEI-pcDNA3-FP2A-IAPP-FNDC5-treated DIO mice group remained high.

The results of this example demonstrate that treatment with the lPEI-pcDNA3-FP2A-IAPP-FNDC5 polyplex increases energy metabolism and browning in DIO mice.

Example 8

This example describes the effect of lPEI-pcDNA3-FP2A-IAPP-FNDC5 on local adipose tissues in vivo.

Figure 14A:
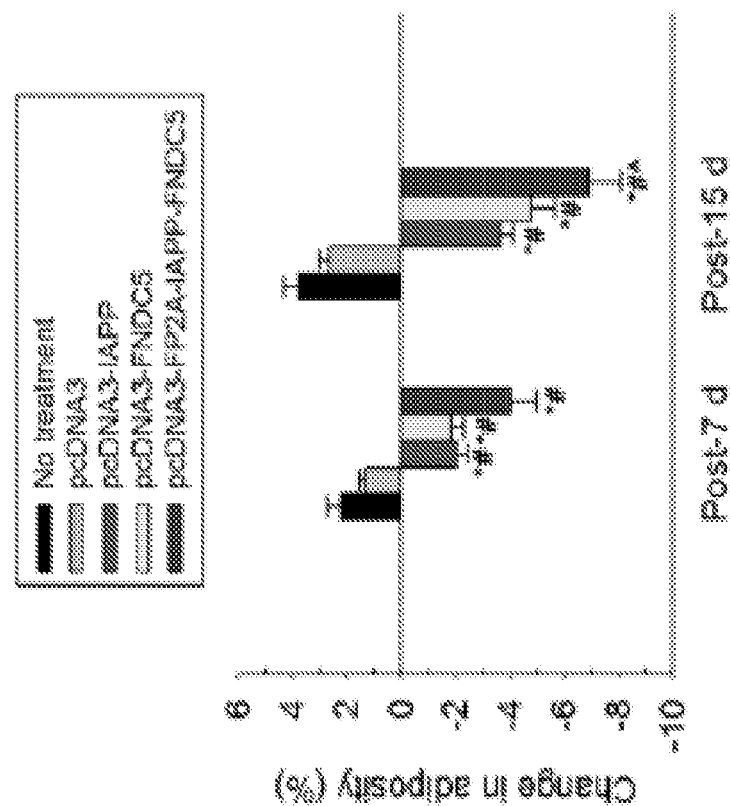
FIG. 14A is a graph illustrating changes in percent body fat.
Figure 14B:
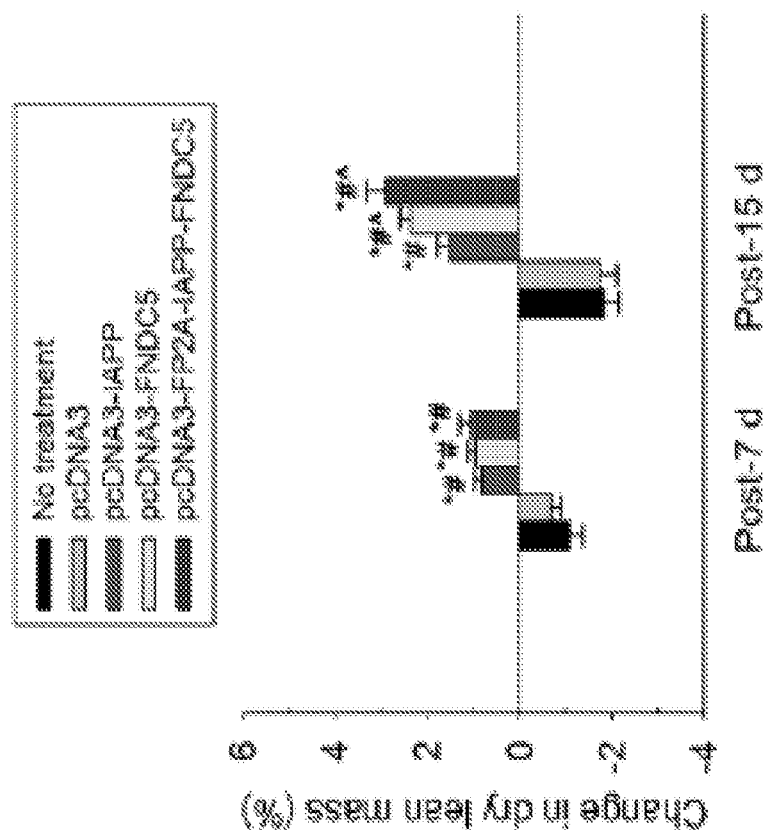
FIG. 14B is a graph illustrating changes in dry lean mass of each treatment group. For FIGS. 14A and 14B, n ¼ 5 per group. Error bars in the graph represent, #$P<0.05$ vs. pcDNA3, ^$P<0.05$ vs. pcDNA3-IAPP, +$P<0.05$ vs. pcDNA3-FNDC5.

To determine the changes in total fat and dry lean mass, mice treated with plasmid DNA polyplexes as described in Example 7 were inserted into a rodent nuclear magnetic resonance machine (Bruker) at the following time points: pre-treatment, post-first treatment (7 days), and post-second treatment (15 days). Total adiposity was quantified as described in Example 5. Changes in the percentage of adiposity and dry lean mass were determined by calculating the difference at 7 days (post-first treatment) and at 15 days (post-second treatment) from pre-injection, respectively.

lPEI-pcDNA3-FP2A-IAPP-FNDC5-treated mice exhibited a significant decrease in adiposity as measured by rodent NMR assay (FIG. 14A). While an increase in adiposity was detected in the control untreated DIO mice and DIO mice treated with lPEI-pcDNA3-treated due to HFD feeding, a significant reduction of whole body adiposity in the DIO mice treated with lPEI-pcDNA3-IAPP, lPEI-pcDNA3-FNDC5, and lPEI-pcDNA3-FP2A-IAPP-FNDC5 was observed. Treatment with lPEI-pcDNA3-IAPP, lPEI-pcDNA3-FNDC5, and lPEI-pcDNA3-FP2A-IAPP-FNDC5 did not reduce the percentage of total dry lean mass following two administrations of each plasmid (FIG. 14B). These results suggest that body weight loss in mice treated with the plasmid-polyplex conjugates may be caused by a decrease in adipose tissues. Expansion of adipose tissue was observed in untreated DIO mice and DIO mice treated with lPEI-pcDNA3.

Figure 14C:
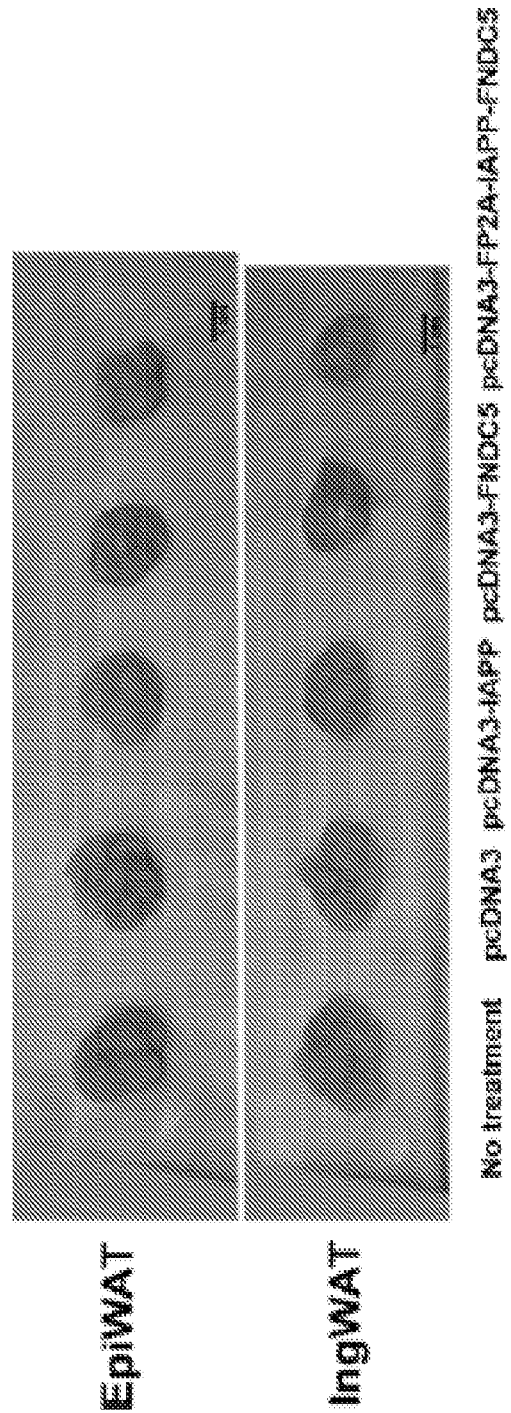
FIG. 14C includes representative images of EpiWAT and IngWAT after two polyplex treatments (n=4).
Figure 14D:
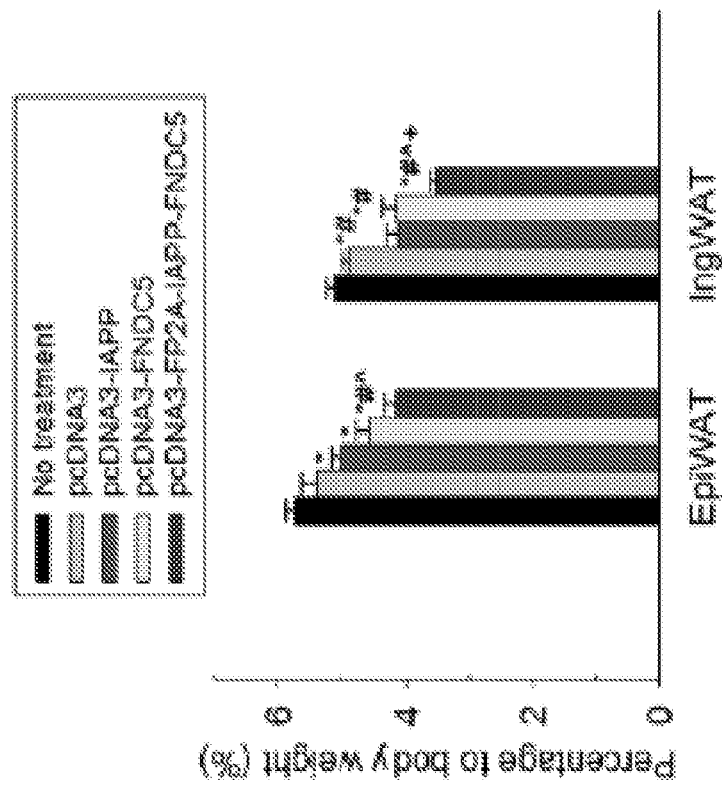
FIG. 14D is a graph illustrating the ratios of WAT weight to body weight (n ¼ 4).

The changes in EpiWAT and IngWAT in treated mice were evaluated. Total RNA from IngWAT was extracted using the Trizol-based method, and reverse transcribed with High-Capacity RNA-to-cDNA™ Kit purchased from Invitrogen (Carlsbad, Calif., USA). Ppargc1a (Mm01208835_m1), Prdm16 (Mm00712556_m1), and Pparg (Mm01184322_m1) were measured using Single Tube TAQMAN® Gene Expression Assays. Eukaryotic 18S rRNA was used as endogenous control. Quantitative measures were obtained by the DDCT. The volume (FIG. 14C) and weight (FIG. 14D) of WATs from lPEI-pcDNA3-FP2A-IAPP-FNDC5 treated DIO mice were markedly less than those from all the other groups. In addition, there was a noticeable reduction of IngWAT in lPEI-pcDNA3-IAPP-treated mice and lPEI-pcDNA3-FNDC5-treated mice as compared to the two control groups.

The results of this example suggest that the delivery of lPEI-pcDNA3-FP2A-IAPP-FNDC5 can elicit a browning effect, leading to the decline in fat mass.

Example 9

This example describes the effects of lPEI-pcDNA3-FP2A-IAPP-FNDC5 on metabolic variables in blood.

The levels of serum insulin, free fatty acids, and triglycerides in DIO mice treated with the plasmid-polyplexes as described in Example 7 were measured using a Mouse Insulin ELISA Kit (Crystal Chem), an FFA test kit (Roche), and TG assay solutions (Wako Diagnostics, Richmond, Va., USA), respectively. For blood glucose measurements, about five microliters of blood drawn from the tail vein of 6 hour-fasted DIO mice was placed onto a glucose test strip (American Diabetes Wholesale) and glucose levels were measured using a blood glucose meter (Bayer Contour). Before polyplex treatments, the initial blood glucose level of all mice was between 170-220 mg/dL.

Figure 15B:
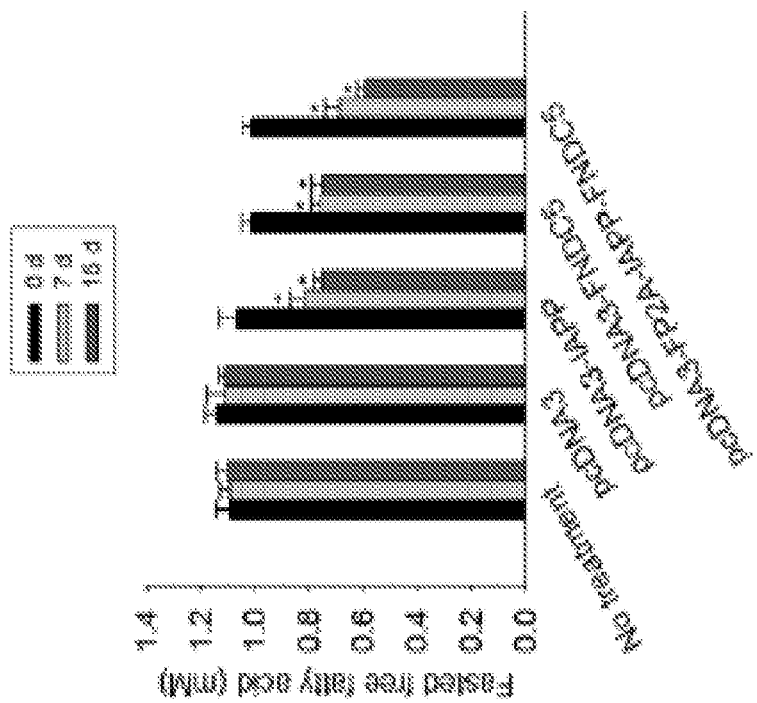
FIG. 15 includes graphs illustrating the effect of lPEI-pDNA polyplex injections on blood triglyceride levels (15A), free fatty acid levels (15B), and insulin levels (15C) in DIO mice after 6 hours of fasting at pre-treatment (0 days), post-1st treatment (7 days), and post-2nd treatment (15 days). Error bars in the graph represent SEM, n 5 per group. *$P<0.05$ vs. 0 d.
FIG. 15D is a graph illustrating blood glucose levels measured at each indicated time point. Results are presented as means±SEM, n ¼ 6 per group. *$P<0.05$ vs. No treatment, #$P<0.05$ vs. pcDNA3, ^$P<0.05$ vs. pcDNA3-IAPP, +$P<0.05$ vs. pcDNA3-FNDC5.
Figure 15D:
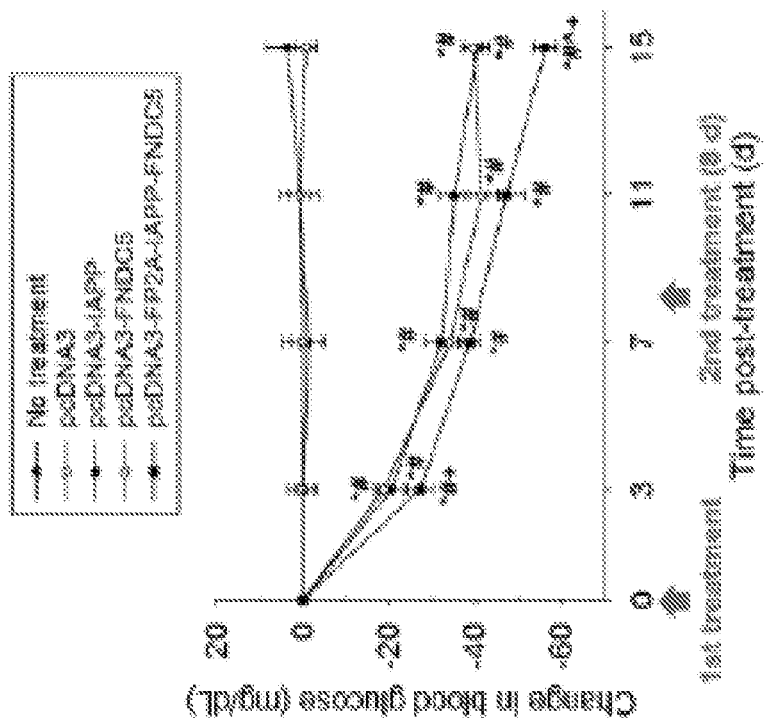

Administration of lPEI-pcDNA3-FP2A-IAPP-FNDC5 resulted in a significant decrease in circulating levels of triglyceride (TG), free fatty acid (FFA), insulin, and glucose (FIG. 15). Consistent with the decrease in total body adiposity induced by certain polyplexes described in Example 8 (FIG. 14A), the levels of both TG and FFA were significantly decreased in DIO mice treated with lPEI-pcDNA3-IAPP, lPEI-pcDNA3-FNDC5, and lPEI-pcDNA3-FP2A-IAPP-FNDC5 after twice weekly treatments.

The results of this example demonstrate that in vivo delivery of the lPEI-pcDNA3-FP2A-IAPP-FNDC5 polyplex decreased serum levels of glucose, insulin, free fatty acids, and triglycerides.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A plasmid comprising two or more of:
   a) a nucleic acid sequence encoding islet amyloid polypeptide (IAPP);
   b) a nucleic acid sequence encoding leptin (LEP); and
   c) a nucleic acid sequence encoding fibronectin type III domain containing 5 (FNDC5);
   wherein the plasmid comprises the nucleic acid sequence of SEQ ID NO: 10 or SEQ ID NO: 11.

2. The plasmid of claim 1, which comprises a nucleic acid sequence encoding IAPP and a nucleic acid sequence encoding LEP.

3. The plasmid of claim 1, which comprises a nucleic acid sequence encoding IAPP and a nucleic acid sequence encoding FNDC5.

4. The plasmid of claim 1, which comprises a nucleic acid sequence encoding LEP, a nucleic acid sequence encoding FNDC5, and a nucleic acid sequence encoding IAPP.

5. The plasmid of claim 1, which is conjugated to a non-viral carrier.

6. The plasmid of claim 5, wherein the non-viral carrier is polyethylenimine, linear polyethylenimine (PEI), reducible polyethyleneimine, poly(l lysine), poly[(2 dimethylamino) ethyl methacrylate], poly(β amino ester)s, chitosan, polyamidoamine dendrimer, poly[a-(4-aminobutyl)-L-glycolic acid], or a PEG grafted polycation.

7. A composition comprising the plasmid of claim 1 and a pharmaceutically acceptable carrier.

8. An isolated host cell comprising the composition of claim 7.

9. The isolated host cell of claim 8, which is an isolated mammalian cell.

10. The isolated host cell of claim 9, which is an isolated mouse cell.

11. The isolated host cell of claim 9, which is an isolated human cell.

12. A method for increasing metabolic activity in an animal, which method comprises administering to the animal the composition of claim 7, whereby the two or more nucleic acids sequences are expressed in the animal and metabolic activity is increased.

13. The method of claim 12, wherein the composition is administered to the animal orally or by intraperitoneal injection.

14. The method of claim 12, wherein the animal is a mammal.

15. The method of claim 14, wherein the mammal is a mouse.

16. The method of claim 14, wherein the mammal is a human.

* * * * *